US012661395B2

(12) United States Patent
Pearce

(10) Patent No.: US 12,661,395 B2
(45) Date of Patent: Jun. 23, 2026

(54) CANINE PARVOVIRUS

(71) Applicant: Intervet, Inc, Madison, NJ (US)

(72) Inventor: Jacqueline Pearce, Boxmeer (NL)

(73) Assignee: Intervet Inc., Rahway, NJ (US)

( * ) Notice: Subject to any disclaimer, the term of this patent is extended or adjusted under 35 U.S.C. 154(b) by 553 days.

(21) Appl. No.: 18/250,761

(22) PCT Filed: Nov. 3, 2021

(86) PCT No.: PCT/EP2021/080429
§ 371 (c)(1),
(2) Date: Apr. 27, 2023

(87) PCT Pub. No.: WO2022/096472
PCT Pub. Date: May 12, 2022

(65) Prior Publication Data
US 2023/0405110 A1      Dec. 21, 2023

(30) Foreign Application Priority Data
Nov. 4, 2020      (EP) ..................................... 20205745

(51) Int. Cl.
| | |
|---|---|
| *A61K 39/23* | (2006.01) |
| *A61P 31/20* | (2006.01) |
| *C12N 7/08* | (2006.01) |
| *A61K 39/00* | (2006.01) |

(52) U.S. Cl.
CPC .............. *A61K 39/23* (2013.01); *A61P 31/20* (2018.01); *C12N 7/08* (2013.01); *A61K 2039/5254* (2013.01); *A61K 2039/545* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 6,187,759 B1 | 2/2001 | Tarpey et al. | |
| 2013/0195913 A1* | 8/2013 | Spibey | A61K 39/23 435/235.1 |
| 2015/0306209 A1* | 10/2015 | Wasmoen | A61K 39/23 435/320.1 |
| 2023/0405110 A1* | 12/2023 | Pearce | C12N 7/00 |

FOREIGN PATENT DOCUMENTS

| | | |
|---|---|---|
| WO | WO 2012007589 A1 | 1/2012 |
| WO | 2014029702 A1 | 2/2014 |
| WO | WO 2014095956 A1 | 6/2014 |

OTHER PUBLICATIONS

"Pet Vaccination 'Isolation Period' Explained!" by Northshore Pet Resort, posted Apr. 2, 2019.*
"Cell Culture Tips for Cell Lines and Primary Cells Prior to Transfection" by Lonza Cologne GmbH, published 2012; found at https://knowledge.lonza.com/downloadasset.ashx?assetId=29943.*

* cited by examiner

*Primary Examiner* — Shanon A. Foley
(74) *Attorney, Agent, or Firm* — Susanna C. Benn

(57) ABSTRACT

The invention relates to a live attenuated parvovirus for use in the protection of an animal against parvovirus infection. The invention further relates to vaccines comprising the live attenuated parvovirus as well as methods for their production.

18 Claims, 9 Drawing Sheets

Specification includes a Sequence Listing.

Fig. 1

```
541   aaactttga tgcattaact aaaaaatgtc ttttgaagt ccttgtttct aaaaatatag
      tttgaaact acgtaattaa tttttacag aaaaacttca gaaacaaaga tttttatatc
      >.........................Non Structural Gene......................>
       q  t  f   d  a  l   l  k  k   c  l  f   s  v  f   v  s  k   a  i 601   aaccaaatga atgtgtttgg tttattcaac atgaatgggg aaaagatcaa ggctggcatt
      ttggtttact tacacaaacc aaataagttg tacttacccc ttttctagtt ccgaccgtaa
      >.........................Non Structural Gene......................>
       e  p  n   e  c  v   w  f  i   q  h  e   w  g  k   d  q  g   w  h 661   gtcatgtttt acttcatagt aagaacttac aacaagcaac tggtaaatgg ctacgcagac
      cagtacaaaa tgaagtatca ttcttgaatg ttgttcgttg accatttacc gatgcgtctg
      >.........................Non Structural Gene......................>
       c  h  v   l  l  h   s  k  n   l  q  q   a  t  g   k  w  l   r  r 721   aaatgaatat gtattggagt agatggttgg tgactctttg ttggtaaac ttaacaccaa
      tttacttata cataacctca tctaccaacc actgagaaac aagccatttg aattgtggtt
      >.........................Non Structural Gene......................>
       q  m  n   m  y  w   s  r  w   l  v  t   l  c  s   v  a  l   t  p 781   ctgaaaagat taagctcaga gaaattgcag aagatagtga atgggtgact atattaacat
      gacttttcta attcgagtct ctttaacgtc ttctatcact tacccactga tataattgta
      >.........................Non Structural Gene......................>
       t  e  k   i  k  l   r  e  i   a  e  d   s  e  w   v  t  i   l  t 841   acagacataa gcaaacaaaa aaagactatg ttaaaatggt tcattttgga aatatgatag
      tgtctgtatt cgtttgtttt tttctgatac aattttacca agtaaaacct ttatactatc
      >.........................Non Structural Gene......................>
       y  r  h   k  q  t   k  k  d   y  v  k   m  v  h   f  g  n   m  i 901   catattactt tttaacaaag aaaaaaattg tccacatgac aaaagaaagt ggctattttt
      gtataatgaa aaattgtttc ttttttaac aggtgtactg ttttctttca ccgataaaaa
      >.........................Non Structural Gene......................>
       a  y  y   f  l  t   k  k  k   i  v  h   m  t  k   e  s  g   y  f 961   caagtactga ttctggttgg aaatttaact ttatgaagta tcaagacaga caaattgtca
      attcatgact aagaccaacc tttaaattga aatacttcat agttctgtct gtttaacagt
      >.........................Non Structural Gene......................>
       l  s  t   d  s  g   w  k  f   n  f  m   k  y  q   d  r  q   i  v 1021  gcacacttta cactgaacaa atgaaaccag aaaccgttga aaccacagtg acgacagcac
      cgtgtgaaat gtgacttgtt tactttggtc tttggcaact tggtgtcac tgctgtcgtg
      >.........................Non Structural Gene......................>
       s  t  l   y  t  e   q  m  k   p  e  t   v  e  t   t  v  t   t  a 1081  aggaaacaaa gcgcgggaga attcaaacta aaaggaagt gtcaatcaaa tgtactttgc
      tcctttgttt cgcgccctct taagtttgat tttccttca cagttagttt acatgaaacg
      >.........................Non Structural Gene......................>
       q  e  t   k  r  g   r  i  q   t  k  e   v  s  i   k  c  t   l Xba I
1141  gggacttggt tagtaaaaga gtaacatcac ctgaagactg gatgatgtta caaccagata
      ccctgaacca atcattttct cattgtagtg gacttctgac ctactacaat gttggtctat
      >.........................Non Structural Gene......................>
       r  d  l   v  s  k   r  v  t   s  p  e   d  w  m   m  l  q   p  d
```

Fig. 1

```
1301   gttatattga aatgatggca caaccaggag gtgaaaatct tttaaaaaat acacttgaaa
       caatataact ttactaccgt gttggtcctc cactttagaa aaattttta tgtgaacttt
       >..........................Non Structural Gene......................>
        s   y   i   e   m   m   a   q   p   g   g   e   n   l   l   k   n   t   l   e 1361   tttgtacttt gactttagca agaacaaaaa cagcatttga attaatactt gaaaaagcag
       aaacatgaaa ctgaaatcgt tcttgttttt gtcgtaaact taattatgaa cttttttcgtc
       >..........................Non Structural Gene......................>
        i   c   t   l   t   l   a   r   t   k   t   a   f   e   l   i   l   e   k   a XbaI
                                                   _____
1321   ataatactaa actaactaac tttgatcttg casattctag aacatgtcaa attttagaa
       tattatgatt tgattgattg aaactagaac gtttaagatc ttgtacagtt taaaaatctt
       >..........................Non Structural Gene......................>
        d   n   t   k   l   t   n   f   d   l   a   n   s   r   t   c   q   i   f   r SacI
    _____
1381   tgcacggatg gaattggatt aaagtttgtc acgctatagc atgtgtttta aatagacaag
       acgtgcctac cttaactaa tttcaaacag tgcgatatcg tacacaaaat ttatctgttc
       >..........................Non Structural Gene......................>
        m   h   g   w   n   w   i   k   v   c   h   a   l   a   c   v   l   n   r   q 1441   gtggtaaaag aaatacagtt cttttttcatg gaccagcaag tacaggaaaa tctatcattg
       caccattttc tttatgtcaa gaaaaagtac ctggtcgttc atgtccttt agatagtaac
       >..........................Non Structural Gene......................>
        g   g   k   r   n   t   v   l   f   h   g   p   a   s   t   g   k   a   i   i 1501   ctcaagccat agcacaagct gtgggtaatg ttggtggta caatgcagca aatgtaaatt
       gagttcggta tcgtgttcga cacccattac aaccaacaat attacgtcgt ttacattaa
       >..........................Non Structural Gene......................>
        a   q   a   i   a   q   a   v   g   n   v   g   c   y   n   a   a   n   v   n 1561   ttccatttaa tgactgtacc aataaaaatt caattggat tgaagaagct ggtaactttg
       aaggtaaatt actgacatgg ttatttttaa attaaccta acttcttcga ccattgaaac
       >..........................Non Structural Gene......................>
        f   p   f   n   d   c   t   n   k   n   l   i   v   i   e   e   a   g   n   f BstI
                                                                _____
1631   gtcaacaagt taatcaattt aaagcaattt gttctggaca aacaattaga attgatcaaa
       cagttgttca attagttaaa tttcgttaaa caagacctgt ttgttaatct taactagttt
       >..........................Non Structural Gene......................>
        g   q   q   v   n   q   f   k   a   i   c   s   g   q   t   i   r   i   d   q 1681   aaggtaaagg aagtaagcaa attgaaccaa ctccagtaat tatgacaact aatgaaaata
       ttccatttcc ttcattcgtt taacttggtt gaggtcatta atactgttga ttactttat
       >..........................Non Structural Gene......................>
        k   g   k   g   s   k   q   i   e   p   t   p   v   i   m   t   t   n   e   n 1741   taacaattgt gaggattgga tgtgaagaa gacctgaaca tacacaacca ataagagaca
       attgttaaca ctcctaacct acacttcttt ctggactgt atgtgttggt tattctctgt
       >..........................Non Structural Gene......................>
        i   t   i   v   r   i   g   c   e   e   r   p   e   h   t   q   p   i   r   d
```

Fig. 1

```
1801  gaatgttgaa cattaagtta gtatgtaagc ttccaggaga cttggtttg gttgataaag
      cttacaactt gtaattcaat catacattcg aaggtcctct gaaaccaaac caactatttc
      >.................Non Structural Gene...................>
        r  m  l  n  i  k  l  v  c  k  l  p  g  d  f  g  l  v  d  k 1861  aagaatggcc tttaatatgt gcatggttag ttaaacatgg ttatgaatca accatggcta
      ttcttaccgg aaattataca cgtaccaatc aattgtacc aatacttagt tggtaccgat
      >.................Non Structural Gene...................>
        e  e  w  p  l  i  c  a  w  l  v  k  h  g  y  e  s  t  m  a 1921  actatacaca tcattgggga aaagtaccag aatgggatga aaactgggcg gagcctaaaa
      tgatatgtgt agtaacccct tttcatggtc ttaccctact tttgacccgc ctcggatttt
      >.................Non Structural Gene...................>
        n  y  t  h  h  w  g  k  v  p  e  w  d  e  n  w  a  e  p  k SacI
1981  tacaagaagg tataaattca ccaggttgca aagacttaga gacacaagcg gcaagcaatc
      atgttcttcc atatttaagt ggtccaacgt ttctgaatct ctgtgttcgc cgttcgttag
      >.................Non Structural Gene...................>
        i  q  e  g  i  n  s  p  g  c  k  d  l  e  t  q  a  a  s  n SacII
2041  ctcagagtca agaccaagtt cacgtacgta tgactccgga cgtagtggac cttgcactgg
      gagtctcagt tctggttcaa gtgcatgcat actgaggcct gcatcacctg gaacgtgacc
                           Hotspot
      >.................Non Structural Gene...................>
        p  q  s  q  d  q  v  h  v  r  m  t  p  d  v  v  d  l  a  l BstXI
2101  aaccgtggag tactccagat acgcctattg cagaaactgc aaatcaacaa tcaaaccaac
      ttggcacctc atgaggtcta tgcggataac gtcttgacg tttagttgtt agtttggttg
      >.................Non Structural Gene...................>
        e  p  w  s  t  p  d  t  p  i  a  e  t  a  n  q  q  s  n  q 2161  ttggcgttac tcacaaagac gtgcaagcga gtccgacgtg gtccgaaata gaggcagacc
      aaccgcaatg agtgtttctg cacgttcgct caggctgcac caggctttat ctccgtctgg
      >.................Non Structural Gene...................>
        l  g  v  t  h  k  d  v  q  a  s  p  t  w  s  e  i  e  a  d BamHI
2221  tgagagccat cttacttct gaacaattgg aagaagatt tcgagacgac ttggattaag
      actctcggta gaaatgaaga cttgttaacc ttcttctaaa agctctgctg aacctaattc
      >.................Non Structural Gene....................>>
        l  r  a  i  f  t  s  e  q  l  e  d  f  r  d  d  l  d  -
```
                    (SEQ ID NO: 7; nucleotide sequece of non-structural gene)
                    (SEQ ID NO: 8; amino acid sequece of non-structural gene)
```
2261  gtacgatggc acctccggca aagagagcca ggagaggtaa gggtgtgtta gtaaagtggg
      catgctaccg tggaggccgt ttctctcggt cctctccatt cccacacaat catttcaccc 2341  gggagaggaa agatttaata acttaactaa gtatgtgttt ttttatagga cttgtgcct(SEQ ID NO: 9)
      ccctctcctt tctaaattat tgaattgatt catacacaaa aaaatatcct gaacacggag
                                      >>>........Capsid VP1/2........>
                                          m  c  f  f  i  g  l  v  p
```
                                                                    (SEQ ID NO: 10)

Fig. 1

```
2401  caggttataa atatcttggg cctgggaaca gtcttgacca aggagaacca actaaccctt
      gtccaatatt tatagaaccc ggacccttgt cagaactggt tcctcttggt tgattgggaa
                                 CPV 630a
      >...........................Capsid VP1/2.........................>
       p   g   y   k   y   l   g   p   g   n   s   l   d   q   g   e   p   t   n   p 2461  ctgacgccgc tgcaaaagaa cacgacgaag cttacgctgc ttatcttcgc tctggtaaaa
      gactgcggcg acgttttctt gtgctgcttc gaatgcgacg aatagaagcg agaccatttt
                                 CPV 630a
      >...........................Capsid VP1/2.........................>
       s   d   a   a   t   e   b   d   a   y   a   a   y   l   r   a   g   k 2531  acccatactt atatttctcg ccagcagatc aacgctttat agatcaaact aaggacgcta
      tgggtatgaa tataaagagc ggtcgtctag ttgcgaaata tctagtttga ttcctgcgat
      >...........................Capsid VP1/2.........................>
       n   p   y   l   y   f   a   p   a   d   q   r   f   i   d   q   t   k   d   a 2581  aagattgggg ggggaaaata ggacattatt ttttagagc taaaaaggca attgctccag
      ttctaacccc ccccttttat cctgtaataa aaaaatctcg attttttccgt taacgaggtc
      >...........................Capsid VP1/2.........................>
       k   d   w   g   g   k   i   g   h   y   f   f   r   a   k   k   a   i   a   p 2641  tattaactga tacaccagat catccatcaa catcaagacc aacaaaacca actaaaagaa
      ataattgact atgtggtcta gtaggtagtt gtagttctgg ttgttttggt tgattttctt
      >...........................Capsid VP1/2.........................>
       v   l   t   d   t   p   d   h   p   s   t   s   r   p   t   k   p   t   k   r BglI
                                                          ‾‾‾‾‾‾
2701  gtaaaccacc acctcatatt ttcattaatc ttgcaaaaaa aaaaaaagcc ggtgcaggac
      catttggtgg tggagtataa aagtaattag aacgtttttt tttttttcgg ccacgtcctg
      >...........................Capsid VP1/2.........................>
       s   k   p   p   p   h   i   f   i   n   l   a   k   k   k   a   g   a   g BstXI
                                                         ‾‾‾‾‾‾‾‾
                                                           XcmI
                                                         ‾‾‾‾‾‾‾‾
2761  aagtaaaaag agacaatctt gcaccaatga gtgatggagc agttcaacca gacggtggtc
      ttcattttc tctgttagaa cgtggttact cactacctcg tcaagttggt ctgccaccag
      >...........................Capsid VP1/2.........................>
       q   v   k   r   d   n   l   a   p   m   s   d   g   a   v   q   p   d   g   g SacII
         ‾‾‾‾‾‾
2821  aacctgctgt cagaaatgaa agagcaacag gatctgggaa cgggtctgga ggcggggtg
      ttggacgaca gtctttactt tctcgttgtc ctagaccctt gcccagacct ccgccccac
      >...........................Capsid VP1/2.........................>
       q   p   a   v   r   n   e   r   a   t   g   s   g   n   g   s   g   g   g 2881  gtggtggttc tggggtgtg gggatttcta cgggtacttt caataatcag acggaattta
      caccaccaag accccacac ccctaaagat gcccatgaaa gttattagtc tgccttaaat
      >...........................Capsid VP1/2.........................>
       g   g   g   s   g   v   g   i   s   t   g   t   f   n   n   q   t   e   f SacII
                                                          ‾‾‾‾‾‾‾‾
2941  aattttttgga aaacggatgg gtggaaatca cagcaaactc aagcagactt gtacatttaa
      ttaaaaacct tttgcctacc cacctttagt gtcgtttgag ttcgtctgaa catgtaaatt
      >...........................Capsid VP1/2.........................>
       k   f   l   e   n   g   w   v   e   i   t   a   n   s   s   r   l   v   h   l
```

Fig. 1

```
3001   atatgccaga aagtgaaaat tatagaagag tggttgtaaa taatttggat aaaactgcag
       tatacggtct ttcactttta atatcttctc accaacattt attaaaccta ttttgacgtc
                                                        AA97
       >..........................Capsid VP1/2.........................>
         n   m   p   e   s   e   n   y   r   r   v   v   v   n   n   l   d   k   t   a NgoI
3061   ttaacggaaa catggcttta gatgatactc atgcacaaat tgtaacacct tggtcattgg
       aattgccttt gtaccgaaat ctactatgag tacgtgttta acattgtgga accagtaacc
                                      AA101
       >..........................Capsid VP1/2.........................>
         v   n   g   n   a   l   d   d   t   h   a   q   i   v   t   p   w   s   l 3121   ttgatgcaaa tgcttgggga gtttggttta atccaggaga ttggcaacta attgttaata
       aactacgttt acgaacccct caaaccaaat taggtcctct aaccgttgat taacaattat
       >..........................Capsid VP1/2.........................>
         v   d   a   n   a   w   g   v   w   f   n   p   g   d   w   q   l   i   v   n 3181   ctatgagtga gttgcattta gttagttttg aacaagaaat ttttaatgtt gttttaaaga
       gatactcact caacgtaaat caatcaaaac ttgttcttta aaaattacaa caaaatttct
       >..........................Capsid VP1/2.........................>
         t   m   s   e   l   h   l   v   s   f   e   q   e   i   f   n   v   v   l   k 3241   ctgtttcaga atctgctact cagccaccaa ctaaagttta taataatgat ttaactgcat
       gacaaagtct tagacgatga gtcggtggtt gatttcaaat attattacta aattgacgta
       >..........................Capsid VP1/2.........................>
         t   v   s   e   s   a   t   q   p   p   t   k   v   y   n   n   d   l   t   a BglII
3301   cattgatggt tgcattagat agtaataata ctatgccatt tactccagca gctatgagat
       gtaactacca acgtaatcta tcattattat gatacggtaa atgaggtcgt cgatactcta
       >..........................Capsid VP1/2.........................>
         s   l   m   v   a   l   d   s   n   n   t   m   p   f   t   p   a   a   m   r 3361   ctgagacatt gggtttttat ccatggaaac caaccatacc aactccatgg agatattatt
       gactctgtaa cccaaaaata ggtacctttg gttggtatgg ttgaggtacc tctataataa
       >..........................Capsid VP1/2.........................>
         s   e   t   l   g   f   y   p   w   k   p   t   i   p   t   p   w   r   y   y SacI
3421   ttcaatggga tagaacatta gtaccatctc atactggaac tagtggcaca ccaacaaata
       aagttaccct atcttgtaat catggtagag tatgaccttg atcaccgtgt ggttgtttat
          AA219 Isoleucine to Valine Change
       >..........................Capsid VP1/2.........................>
         f   q   w   d   r   t   l   v   p   s   h   t   g   t   s   g   t   p   t   n 3481   tataccatgg tacagatcca gatgatgttc aattttatac tattgaaaat tctgtgccag
       atatggtacc atgtctaggt ctactacaag ttaaaatatg ataacttta agacacggtc
       >..........................Capsid VP1/2.........................>
         i   y   h   g   t   d   p   d   d   v   q   f   y   t   i   e   n   s   v   p 3541   tacacttact aagaacaggt gatgaatttg ctacaggaac atttttttt gattgtaaac
       atgtgaatga ttcttgtcca ctacttaaac gatgtccttg taaaaaaaa ctaacatttg
       >..........................Capsid VP1/2.........................>
         v   h   l   l   r   t   g   d   e   f   a   t   g   t   f   f   d   c   k
```

Fig. 1

```
4201   aagaatttga tactgactta aaaccaagac ttcatgtaaa tgcaccattt gttgtcaaa
       ttcttaaact atgactgaat tttggttctg aagtacattt acgtggtaaa caaacagttt
       >..........................Capsid VP1/2..........................>
        k   e   f   d   t   d   l   k   p   r   l   h   v   n   a   p   f   v   c   q
```

```
4261   ataattgtcc tggtcaatta tttgtaaaag ttgcgcctaa tttaacaaat gaatatgatc
       tattaacagg accagttaat aaacattttc aacgcggatt aaattgttta cttatactag
       >..........................Capsid VP1/2..........................>
        n   n   c   p   g   q   l   f   v   k   v   a   p   n   l   t   n   e   y   d
```

```
4321   ctgatgcatc tgctaatatg tcaagaattg taacttactc agatttttgg tggaaaggta
       gactacgtag acgattatac agttcttaac attgaatgag tctaaaaacc acctttccat
       >..........................Capsid VP1/2..........................>
        p   d   a   s   a   n   m   s   r   i   v   t   y   s   d   f   w   w   k   g
```

```
4381   aattagtatt taaagctaaa ctaagagcct ctcatacttg gaatccaatt caacaaatga
       ttaatcataa atttcgattt gattctcgga gagtatgaac cttaggttaa gttgtttact
       >..........................Capsid VP1/2..........................>
        k   l   v   f   k   a   k   l   r   a   s   h   t   w   n   p   i   q   q   m
```

```
4441   gtattaatgt agataaccaa tttaactatg taccaagtaa tattggaggt atgaaaattg
       cataattaca tctattggtt aaattgatac atggttcatt ataacctcca tactttttaac
       >..........................Capsid VP1/2..........................>
        s   i   n   v   d   n   q   f   n   y   v   p   s   n   i   g   g   m   k   i
```

```
4501   tatatgaaaa atctcaacta gcacctagaa aattatatta acatacttac tatgtttttta
       atatactttt tagagttgat cgtggatctt ttaatataat tgtatgaatg atacaaaaat
       >..................Capsid VP1/2...................>>
        v   y   e   k   s   q   l   a   p   r   k   l   y   .
```

(SEQ ID NO: 10; amino acid sequence) >>.Right Hand ITR..>
(SEQ ID NO: 9; nucleic acid seq of caspid VP1/2)

```
4561   tgtttattac atattatttt aagattaatt aaattacagc atagaaatat tgtacttgta
       acaaataatg tataataaaa ttctaattaa tttaatgtcg tatctttata acatgaacat
       >.....................Right Hand ITR........................>
```

```
4621   tttgatatag gatttagaag gttgttata tggtatacaa taactgtaag aaatagaaga
       aaactatatc ctaaatcttc caaacaatat accatatgtt attgacattc tttatcttct
       >.....................Right Hand ITR........................>
```

```
4681   acattagat catagttagt agttgttttt ataaaatgta ttgtaaacta ttaatgtatg
       tgtaaatcta gtatcaatca tcaaacaaaa tatttacat aacatttgat aattacatac
       >.....................Right Hand ITR........................>
```

```
4741   ttgttatggt gtgggtggtt ggttggtttg ccttagaat atgttaagga ccaaaaaaaa
       aacaatacca cacccaccaa ccaaccaaac gggaatctta tacaattcct ggtttttttt
       >.....................Right Hand ITR........................>
```

Fig. 1

```
4801  tcaataaaag acattaaaaa ctaaatggcc tcgtatactg tctataaggt gaactaacct
      agttattttc tgtaaatttt gattaccgg agcatatgac agatattcca cttgattgga
      >.......................Right Hand ITR.........................>

(SEQ ID NO: 11)
4861  taccataagt atcaatctgt ctttaagggg ggggtgggtg ggannnnnnn nnnnnnnnnn
      atggtattca tagttagaca gaaattcccc ccccacccac cctnnnnnnn nnnnnnnnn
      >.......................Right Hand ITR.........................>>
```

CANINE PARVOVIRUS

CROSS-REFERENCE TO RELATED APPLICATIONS

This application is a National Stage application of International Patent Application No. PCT/EP2021/080429, filed Nov. 3, 2021, which claims priority to European Patent Application No. 20205745.1, filed Nov. 4, 2020.

SEQUENCE LISTING

The instant application contains a Sequence Listing which has been submitted electronically in ASCII format and is hereby incorporated by reference in its entirety. Said ASCII copy, created on May 24, 2023, is named 25123-US-PCT_SL.txt and is 31,426 bytes in size.

BACKGROUND OF THE INVENTION

Parvovirus belongs to the family of single stranded DNA viruses. Parvoviruses can cause disease in some animals like cats, dogs, and pigs. Because the viruses require actively dividing cells in order to replicate, the type of tissue infected varies with the age of the animal. The gastrointestinal tract and lymphatic system can be affected at any age, leading to vomiting, diarrhea, and immunosuppression, but cerebellar hypoplasia is only seen in cats that were infected in the womb or at less than two weeks of age, and disease of the myocardium is seen in puppies infected between the ages of three and eight weeks.

Canine parvovirus is a particularly deadly disease among young puppies, about 80% fatal, causing gastrointestinal tract damage and dehydration as well as a cardiac syndrome in very young pups. It is spread by contact with an infected dog's feces. Symptoms include lethargy, severe diarrhea, fever, vomiting, loss of appetite, and dehydration. Porcine parvovirus causes a reproductive disease in swine known as SMEDI, which stands for stillbirth, mummification, embryonic death, and infertility. Feline panleukopenia is common in kittens and causes fever, low white blood cell count, diarrhea, and death. Infection of the cat fetus and kittens less than two weeks old causes cerebellar hypoplasia. Mink enteritis virus is similar in effect to feline panleukopenia, except that it does not cause cerebellar hypoplasia. A different parvovirus causes Aleutian Disease in minks and other mustelids, characterized by lymphadenopathy, splenomegaly, glomerulonephritis, anemia, and death. Dogs, cats, and swine can be vaccinated against parvovirus.

At the DNA level, canine and feline parvoviruses are known to have a highly homologous genome. Canine parvovirus (CPV2) is a virus which is responsible for an acute and sometimes fatal enteritis in dogs. The virus, which first appeared around 1977, probably arose from a very closely related virus in cats, feline panleukopaenia virus (FPLV) through a small number of mutations in the single capsid protein; a species jump which may have involved intermediate passage in other carnivores such as mink or raccoons.

The first CPV type 2 variant, termed CPV2a, appeared as early as 1979, and was quickly followed by the appearance of a second variant, termed CPV2b, in 1984. The original type 2 virus has now disappeared from the field having been replaced by the 2a and 2b variants, although the relative proportions of these two types varies from country to country. The amino acid changes in the capsid protein (VP2), which characterize the shift from 2 to 2a and to 2b, are very limited. Substitutions at positions 87 (Met to Leu), 300 (Ala to Gly), 305 (Asp to Tyr) and 555 (Val to Ile) occurred in the evolution of 2 to 2a and 426 (Asn to Asp) and 555 (Ile to Val) in the emergence of 2b from 2a. It appeared that a single amino acid change at amine acid position 426 can differentiate the CPV2a and CPV2b VP2 sequences. Around the year 2000, another substitution at the same amino acid position arose, changing the Asp426 to Glu. The resulting variant is referred to as CPV-2c. The relatively rapid evolution of the original canine parvovirus type 2 virus resulted in the loss and then re-gaining of the feline host range in later CPV2a, 2b and 2c variants. This regained ability to replicate in cats may well account for the replacement of the original type 2 virus with the 2a, 2b and 2c variants.

In the late 1970s and early 1980s both live and inactivated feline parvovirus (FPV) vaccines were used to protect dogs against CPV disease due to the shared antigens which stimulated cross-protection, however the levels of protection they afforded was poor and duration of immunity was short. These vaccines were replaced by live attenuated CPV vaccines, which provided excellent protection and longer duration of immunity.

Currently, live attenuated vaccine strains are derived from either CPV2b isolates or the original type 2 virus. Since the type 2 virus has been entirely replaced in the field by 2a, 2b and now 2c viruses, there has been concern over the level of protection afforded by attenuated type 2 vaccines. It has previously been demonstrated that a live attenuated CPV2 vaccine is able to protect dogs against 2a and 2b field challenges and that a live attenuated type 2 vaccine (Nobivac-Intervet) was able to protect dogs from challenge with the most recent CPV variant, CPV2c (Spibey et al., Vet. Microbiol 128, 48-55, 2008).

A live attenuated CPV 2c vaccine strain was described in WO 2012/007589, which is hereby incorporated by reference in its entirety, and disclosing a live attenuated parvovirus comprising a capsid gene coding for an amino acid other than Isoleucine at amino acid position 219 of the VP2 capsid protein and/or an amino acid other than Glutamine at amino acid position 386 of the VP2 capsid protein.

Pups born to immune mothers are passively protected during their early life by maternally derived antibody (MDA) acquired perinatally from their dams. It has been calculated that the pup receives approximately 90% of its MDA via the colostrum, whereas transplacental transfer accounts for only 10% of total passive antibody. Soon after birth the average pup will have a serum antibody level equal to 50% that of its dam. However, this MDA proceeds to decline exponentially with a half-life of approximately 10 days. Considerable within-litter variation in MDA levels can sometimes occur, particularly when a litter size is above average.

It has been observed that vaccine failures caused by interference with residual MDA frequently occur. In an attempt to cover those pups with high levels of MDA, data sheets were altered to include later vaccinations, and it is currently recommended that 3-4 vaccinations should be given spanning 6-16 weeks of age. WSAVA Canine Vaccination Guidelines recommend vaccination at 6-8 weeks of age followed by further vaccinations every 2-4 weeks until 16 weeks of age or older. However, multiple vaccination schedules are costly, and puppy owners are faced with the problem of confining the new pet until an advanced age, with resultant difficulties in house-training and socializing. The alternative of serological testing to predict and/or confirm vaccination response also means extra visits and expense and is not always practical.

Furthermore, the decline of maternal immunity in a pup and the risk of vaccine failure in the presence of residual MDA leads to a period of time in which the MDA level has declined to a level that no longer provides protection against virulent challenge but in which vaccination in the face of residual MDA levels is ineffective. This leaves a period of several weeks, where the young puppy is susceptible to infection, but still refractory to vaccination. This period has been termed the "Immunity Gap", or the "Window of Susceptibility".

Until now, no vaccine has proven to be of a high enough efficacy in the face of MDA to close this immunity gap and guarantee active protection without multiple vaccinations. A pup's primary vaccination course cannot therefore usually be completed before 16 weeks of age.

Therefore, a need exists in the art to provide a vaccine which can overcome the problem in the art of vaccine failure when the pup is vaccinated in the presence of MDA. In addition, it is desirable to provide a vaccine that can be given to the pup at an early age without the risk of vaccine failure. Further, there exists a need in the field for vaccines that provides immunity against parvovirus infection even after a single vaccination.

SUMMARY OF THE INVENTION

In the present invention it has surprisingly been found that the live attenuated parvovirus (PV) as defined herein can overcome the problems of the prior art. In particular, the present invention provides a live attenuated PV which provides immunity against parvovirus infection even after a single vaccination. Further, it has surprisingly been found that vaccination with the live attenuated PV as defined herein provides immunity against PV infection that is independent of the animal's level of MDA, i.e. immunity against PV infection can be achieved even in the presence of high MDA levels, making serological testing to predict and/or confirm vaccination response unnecessary.

Hence, there is provided a live attenuated PV for use in the protection of an animal against PV infection, the live attenuated PV comprising a capsid gene coding for an amino acid other than Isoleucine at amino acid position 219 of the VP2 capsid protein and/or an amino acid other than Glutamine at amino acid position 386 of the VP2 capsid protein, wherein the live attenuated PV is administered to the animal as a single dose and this single dose is administered during weeks 2-10, or 2-20 of age of the animal.

There is further provided a live attenuated PV for use in the protection of an animal against PV infection, the live attenuated PV comprising a capsid gene coding for an amino acid other than Isoleucine at amino acid position 219 of the VP2 capsid protein and/or an amino acid other than Glutamine at amino acid position 386 of the VP2 capsid protein, wherein administration is performed independent of the animal's pre-vaccination haemagglutinin inhibition (HAI) titre of maternally derived antibody (MDA) measured at time of administration of the live attenuated PV.

There is further provided a live attenuated PV for use in the protection of an animal against PV infection, the live attenuated PV comprising a capsid gene coding for an amino acid other than Isoleucine at amino acid position 219 of the VP2 capsid protein and/or an amino acid other than Glutamine at amino acid position 386 of the VP2 capsid protein, wherein the animal's pre-vaccination HAI titre of maternally derived antibody (MDA) measured at time of administration of the live attenuated PV is higher than 128, or higher than 288.

There is further provided a live attenuated PV for use in the protection of an animal against PV infection, the live attenuated PV comprising a capsid gene coding for an amino acid other than Isoleucine at amino acid position 219 of the VP2 capsid protein and/or an amino acid other than Glutamine at amino acid position 386 of the VP2 capsid protein, wherein the onset of immunity is achieved at day five or earlier, preferably at day four or earlier, most preferably at day three or earlier, following administration of the live attenuated PV.

DEFINITION OF TERMS

Figure 1:
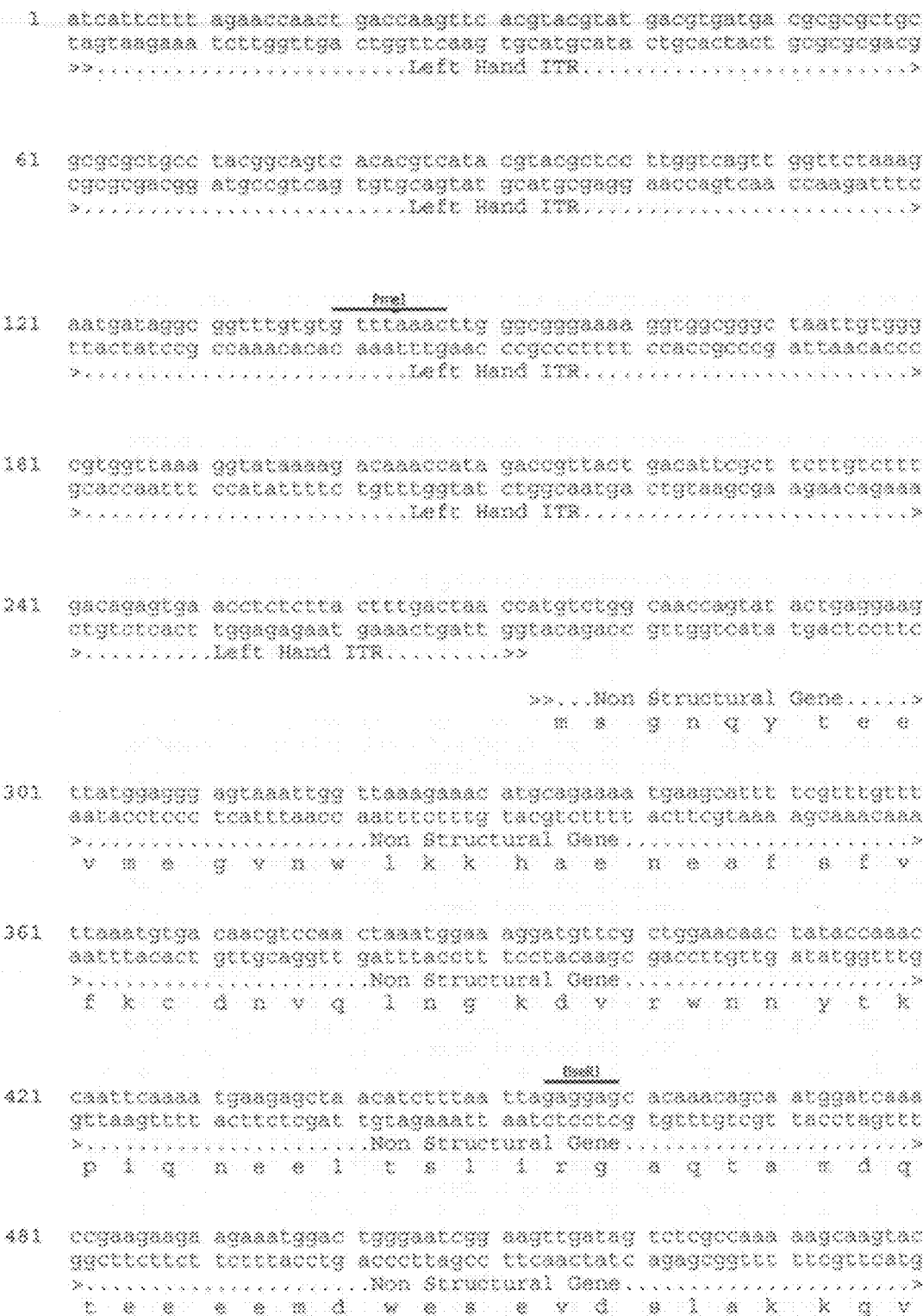
FIG. 1 shows the nucleotide sequence of CPV 630a (SEQ ID NO: 11), which includes the nucleotide sequence of the non-capsid gene (nonstructural gene) (SEQ ID NO: 7) and the amino acid sequences of the non-capsid protein (SEQ ID NO: 8) as well as nucleotide sequence of the capsid gene (Capsid VP1/2) (SEQ ID NO: 9) and the amino acid sequence of capsid protein (SEQ ID NO: 10). The attenuating sequence in the nonstructural gene at nucleotide 2062-2070 is also indicated ("Hotspot") (see also SEQ ID NO: 1).
Figure 1:
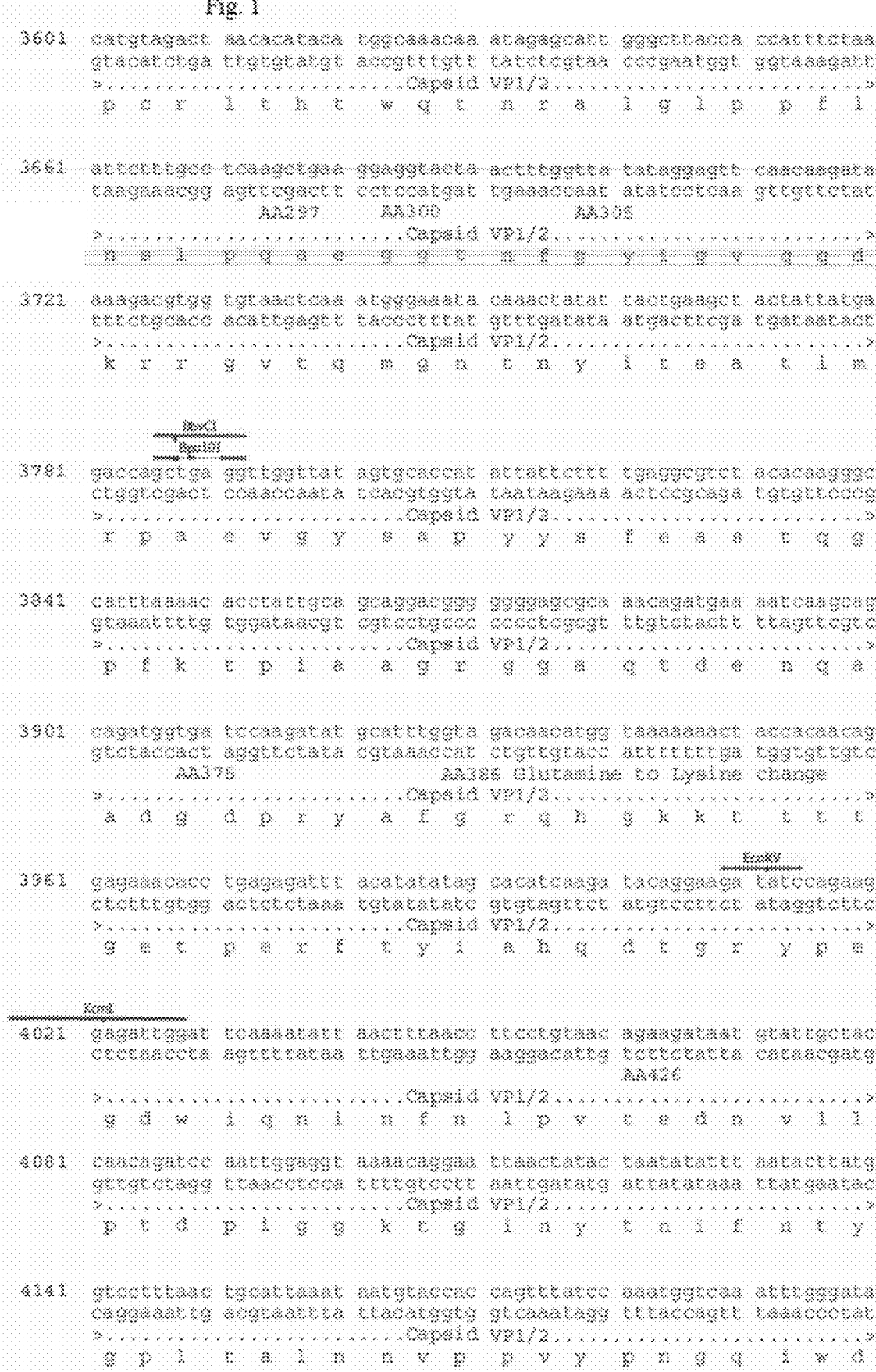

In order to fully appreciate the invention, the following definitions are provided.

The virus according to the invention is a "live attenuated virus". A live attenuated virus is a virus that has a decreased level of virulence when compared to virus isolated from the field. The process of decreasing the virulence of a virus whilst keeping it viable (alive) is known as attenuation. A live attenuated virus is able to replicate to a limited degree within the animal, so inducing strong and long-lived immunity, but without causing the typical clinical signs of disease.

The virus and vaccine according to the invention provide "protection", or are "protecting", "against infection or disease" by preventing disease in a vaccinated target animal. For example, by reducing the number or the duration of the viral replication in the target animal, or reducing the intensity, or the severity of the infection. Also, or consequentially, the method of vaccination provides protection when there is a reduction or amelioration of the (clinical) signs of disease that may be caused by such infection or replication, or by the target animal's response to that infection or replication. As used herein, the terms "protecting", or "providing protection to", do not require complete protection from any indication of infection. For example, "for use in the protection" can mean that the provided protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection. Hence, the term "protection" encompasses a prophylactic treatment against infection with the virus or against a disorder arising from the infection.

The "level of protection" can be determined by measuring the rate of viral replication of a challenge virus in the vaccinated animal. For example, the rate of viral replication can be determined by the level of virus shedding, which refers to the expulsion and release of virus progeny following successful reproduction during a host-cell infection. Therefore, by determining the amount of virus found e.g. in faeces of the animal, the level of protection can be determined by methods known to the skilled person.

The level of protection achieved by vaccination with the live attenuated parvovirus of the present invention is typically higher than 10%, preferably higher than 20% or may be higher than 30%, 40%, 50%, 60%, 70%, 80% and is more preferably 90% or higher. For example, this means that a level of protection of 50% means that for example there is a 50% reduction or amelioration of the (clinical) symptoms of disease when compared to infected but not vaccinated animals. This means for example 50% less viral replication, and/or that the clinical signs have reduced by 50%. Clinical signs may be any of hemorrhagic diarrhea, reduced appetite, weight loss, abdominal pain, dehydration. 50% reduction then means that when compared to non-vaccinated animals, the vaccinated animals have 50% less hemorrhagic diarrhea, for example only for 1 day whereas the non-vaccinated animals have hemorrhagic diarrhea for 2 days.

In the most preferred embodiment, the level of protection achieved by vaccination with the live attenuated parvovirus of the present invention is 100%. For example, this means that after infection no viral replication can be detected in the animal and there are no clinical signs of disease.

Further, the virus and vaccine according to the invention can provide sterilising immunity against shedding. Sterilising immunity is an immune status which prevents effective virus infection of the host following exposure to the virulent pathogen. An animal can be described as having sterilising immunity if it does not develop clinical signs and does not excrete the virulent pathogen following infection. The virus and vaccine according to the invention can thus provide complete protection against disease and can prevent virus shedding after infection.

A preferred form of the live attenuated parvovirus of the present invention and/or embodiments thereof, relates to a live attenuated parvovirus wherein that parvovirus is a recombinant parvovirus that may contain genomic segments from different parvovirus combined. For example, the live attenuated parvovirus of the present invention and/or embodiments thereof may have the capsid gene from a first parvovirus and the structural gene from a second parvovirus. In a non-limiting example, the live attenuated parvovirus of the present invention and/or embodiments thereof may have the capsid gene from parvovirus type 2c and the structural gene from parvovirus type 2. Also, the live attenuated parvovirus of the present invention and/or embodiments thereof may have a part of the capsid gene from a first parvovirus and the rest of the genome from a second parvovirus. For example, a part of the capsid is type 2c whereas the rest of the capsid is 2b, and the structural part is type 2.

A preferred form of the live attenuated parvovirus of the present invention and/or embodiments thereof relates to a live attenuated parvovirus wherein the live attenuated parvovirus carries an attenuating mutation. In a suitable form, the DNA fragment of a part of the non-capsid region of said parvovirus is replaced by a homologous DNA fragment of a part of the non-capsid region derived from a second parvovirus carrying the attenuating mutation. A "homologous DNA" fragment from a second parvovirus is a DNA fragment that has the same function as the DNA fragment of the parvovirus according to the invention but differs from that DNA fragment in that it carries a mutation that leads to attenuated behavior of the virus.

A vaccine's "efficacy" is a measure of how well it protects an animal against disease. This can be determined e.g. by monitoring the active immunological response following vaccination, or by challenge infections with the wild type pathogen. Parameters measured are e.g. the target animal's signs of disease, clinical scores, various blood parameters, or re-isolation of the viral pathogen. These are compared to the response seen in mock-vaccinated or non-vaccinated target animals.

For the vaccines according to the invention and any embodiment thereof the dose or amount of the immunologically active component can be determined in well-known ways, for example: the live attenuated virus can be titrated, e.g. in animals, in fertilized eggs, or on suitable host cells in culture. The result is then expressed e.g. as plaque forming units (pfu), $TCID_{50}$ or $EID_{50}$ per milliliter of the vaccine. Alternatively, the antigen can be quantified by a serologic- or bio-chemical test such as an ELISA or an AlphaLisa™, and expressed in relative units, compared to an appropriate reference standard. All these are well known in the art.

The term "active immunity" as defined herein means a protection to parvovirus infection through the creation of antibodies by the animal's immune system. The "Onset of immunity" is defined herein as the timepoint after vaccination, usually described in days, when the animal is protected against parvovirus infection.

"Non-interference" or "does not interfere" with the efficacy of the treatment in the context of the present invention means that the presence of maternally derived antibodies (MDA) does not inhibit the active production of antibodies in response to the vaccination with the live attenuated parvovirus of the present invention. Hence, an effective immune response following vaccination can be achieved even in the presence of MDA.

The term "immunogenically effective amount" as used herein relates to the amount of virus or vaccine that is necessary to induce an active immune response in the animals to the extent that it protects against infection with a parvovirus.

The determination of whether a treatment is "immunologically effective", can be achieved, for instance, by administering an experimental challenge infection to vaccinated animals and next determining a target animal's clinical signs of disease, serological parameters or by measuring re-isolation of the pathogen, followed by comparison of these findings with those observed in challenged non-vaccinated or field-infected non-vaccinated animals.

As used herein, a "vaccine" is a composition that is suitable for application to an animal, e.g., dog, comprising an immunologically active component, such as one or more antigens, and a pharmaceutically acceptable carrier, such as a liquid containing water, which upon administration to the animal induces an immune response strong enough to minimally aid in the protection from a disease arising from an infection with a micro-organism, i.e., strong enough for aiding in the prevention of the disease, and/or preventing, ameliorating or curing the disease. The carrier can be a liquid or a (particulate) solid. The "immunologically active component" for the invention in the respective vaccines, is the virus in live attenuated form. The vaccines stimulate the immune system of the target animal and induce an immunological response. The response may originate from the target animal's innate- and/or from the acquired immune system and may be of the cellular- and/or of the humoral type.

As used herein, a "multivalent vaccine" or "combination vaccine" is a vaccine that comprises two or more different antigens. In a particular embodiment of this type, the multivalent vaccine stimulates the immune system of the recipient against two or more different pathogens.

As used herein, the term "pharmaceutically acceptable" is used adjectivally to mean that the modified noun is appropriate for use in a pharmaceutical product. When it is used, for example, to describe an excipient in a pharmaceutical vaccine, such as a "pharmaceutically acceptable carrier" it characterizes the excipient as being compatible with the other ingredients of the composition and not disadvantageously deleterious to the intended recipient animal, e.g., dog.

The "administration" of the vaccines according to the invention to a target animal can be performed using any feasible method and route. Typically, the optimal way of administration will be determined by the type of the vaccine applied, and the characteristics of the target animal and the viral disease that it is intended to protect against. For example: because the vaccine comprising a live attenuated virus comprises a replicative antigen, it can be administered using a method of mass application such as via a drinking water- or spray application. Alternatively, for both the vaccine comprising the live attenuated form of a virus, and the vaccine comprising the virus several routes of parenteral, mucosal, topical, or enteral administration are feasible. All this is well known in the art, see e.g. "*Veterinary vaccinology*" (P. Pastoret et al. ed., 1997, Elsevier, Amsterdam, ISBN 0444819681). "Parenteral administration" includes subcutaneous injections, submucosal injections, intravenous injections, intramuscular injections, intradermal injections, and infusion.

Identity, as used herein, nucleotide and amino acid sequence percent identity can be determined using known algorithms to determine sequence identity, such as C, MacVector (MacVector, Inc. Cary, NC 27519), Vector NTI (Informax, Inc. MD), Oxford Molecular Group PLC (1996) and the Clustal W algorithm with the alignment default parameters, and default parameters for identity. These commercially available programs can also be used to determine sequence similarity and identity using the same or analogous default parameters. Alternatively, an Advanced Blast search under the default filter conditions can be used, e.g., using the GCG (Genetics Computer Group, Program Manual for the GCG Package, Version 7, Madison, Wisconsin) pileup program using the default parameters. Other widely used free programs like BLAST (Altschul et al. *Nucleic Acids Res.* 1997 Sep. 1; 25(17):3389-402), FASTA (Pearson W R, Lipman D J *Proc Natl Acad Sci USA*. 1988 April; 85(8): 2444-8) can be used to determine percentage identity.

DETAILED DESCRIPTION OF THE INVENTION

Live Attenuated Parvovirus

The live attenuated parvovirus (PV) of the present invention may be a live attenuated PV as described in WO 2012/007589, which is incorporated herein by reference in its entirety.

In this respect, one embodiment of the present invention and/or any embodiments thereof relates to live attenuated PV that comprise an amino acid other than Isoleucine at amino acid position 219 of the VP2 capsid protein and/or an amino acid other than a Glutamine at amino acid position 386 of the VP2 capsid protein.

It was surprisingly found that these two sites, at amino acid position 219 and 386 of the VP2 capsid protein, play an important role in the attenuation of the virus. Until now it was assumed that mainly amino acids outside the capsid region are involved in the virulence/attenuation of the virus.

The location of the Isoleucine at amino acid position 219 of the VP2 capsid protein and a Glutamine at amino acid position 386 of the VP2 capsid protein is identical in both canine and feline parvoviruses, regardless of the biotype. This means that the invention can at least universally be applied to feline parvoviruses and canine parvoviruses. The invention can also be applied to e.g. Porcine parvoviruses that have an Isoleucine at amino acid position 219 of the VP2 capsid protein and/or a Glutamine at amino acid position 386 of the VP2 capsid protein.

In a parvoviruses, the viral DNA encodes two open reading frames (ORF). The ORF1 encodes nonstructural proteins (NS), and the ORF2 encodes two or three viral particle (VP) proteins which assemble the viral capsid. VP1 is the full translation of the structural gene, and VP2 lacks about ~140 amino acids at the N-terminal, See FIG. 1, and SEQ ID NO: 10 (VP1) and SEQ ID NO: 12 (VP2). VP1 thus contains the full length of VP2. The numbering of amino acid changes 219 and 386 are based on the amino acid numbering of VP2 (SEQ ID NO: 12). As VP1 has 138 additional amino acids at its N-terminal end, the position in VP1 is thus 138 amino acids more. For example amino acid 219 in VP2 is amino acid 357 in VP1.

Thus, a first embodiment of the present invention and/or any embodiments thereof relates to a live attenuated PV, that comprises a capsid gene coding for an amino acid other than Isoleucine at amino acid position 219 of the VP2 capsid protein and/or an amino acid other than Glutamine at amino acid position 386 of the VP2 capsid protein.

Merely to indicate the location of the Isoleucine at amino acid position 219 and the Glutamine at amino acid position 386, the two amino acids are shown below (in bold characters) in an example of the sequential context found in most CPV and FPV strains.

```
                                  (SEQ ID NO: 3)
    YFQWDRTLIPSHTGTSG (I; Isoleucine 219 = bold)

(SEQ ID NO: 4)
    YAFGRQHGQKTTTTGET (Q; Glutamine 386 = bold)
```

Depending upon the strain that is used as the starting material for the substitution of one or both amino acids according to the invention, it may be that a single substitution of the amino acid at position 219 or 386 is not sufficient to e.g. make the virus safe in very young animals. If a further attenuation is required, the substitution of both the amino acid at position 219 and 386 is preferred.

Therefore, a preferred form of this embodiment or any other embodiment of the present invention relates to a live attenuated PV according to the invention that comprises a capsid gene coding for an amino acid other than Isoleucine at amino acid position 219 of the VP2 capsid protein and an amino acid other than Glutamine at amino acid position 386 of the VP2 capsid protein.

A more preferred form of this embodiment or any other embodiment of the present invention relates to a live attenuated PV, that comprises a capsid gene coding for a Valine at amino acid position 219 of the VP2 capsid protein and/or a Lysine at amino acid position 386 of the VP2 capsid protein.

An even more preferred form of this embodiment or any other embodiment of the present invention relates to a live attenuated PV, that comprises a capsid gene coding for a Valine at amino acid position 219 of the VP2 capsid protein and a Lysine at amino acid position 386 of the VP2 capsid protein. Merely to indicate the location of the Valine at amino acid position 219 and the Lysine at amino acid position 386, the two amino acids are shown below (in bold characters) in an example of the sequential context found in most CPV and FPV strains.

```
                                       (SEQ ID NO: 5)
          YFQWDRTLVPSHTGTSG (SEQ ID NO: 6)
          YAFGRQHGKKTTTTGET
```

If a still further attenuation is preferred, it might be attractive to use a PV that already has another attenuating mutation as the starting material for the introduction of an amino acid substitution according to the invention.

Preferably, such an attenuating mutation is located outside the capsid region. This would allow for the replacement of a DNA fragment of a part of the non-capsid region of a virus according to the invention with a homologous non-capsid region of a parvovirus strain that carries an attenuation in that region. Parvoviruses carrying an attenuation in a part of the non-capsid region are e.g. the commercially available canine parvovirus vaccine strain 154 that is present in vaccines such as e.g. Nobivac Parvo C (MSD Animal Health).

The advantage of such an approach is, that such viruses would have an even higher attenuation level. Thus, a still even more preferred form of this embodiment relates to a live attenuated PV according to the invention wherein that PV is a recombinant PV carrying an attenuating mutation in the non-capsid region.

In consequence, it is preferred that the PV of the present invention carries a mutation in the non-capsid region that leads to attenuated behavior of the virus.

A preferred form of the invention and its embodiments relates to a live attenuated PV wherein the parvovirus carries an attenuating mutation in the non-capsid region, in the region from position 2062 to 2070. In a preferred embodiment of the invention and embodiments thereof, the DNA sequence carrying the attenuation mutation has the sequence corresponding to that of SEQ ID NO 1 of: ACG TAC GTA from position 2062 to 2070. The DNA sequence in the region from position 2062 to 2070 in the wild-type parvovirus is that of SEQ ID NO 2 of: TAA CTC CTC.

The attenuation mutation can be introduced by methods well known to the skilled person, for example by exchanging a DNA fragment of a wild-type virus with a homologous DNA fragment carrying the attenuation mutation. For example, a DNA fragment of a part of the non-capsid region of the parvovirus of the present invention can be replaced by a homologous DNA fragment of a part of the non-capsid region derived from a second parvovirus, wherein the homologous DNA fragment of said second parvovirus carries an attenuating mutation. Exchanging of DNA can be done using recombinant DNA techniques well-known in the art, such as site-directed mutagenesis, exchange of restriction fragments and the like. Such nucleotide changes can, for example, be introduced by chemical synthesis or PCR followed by recombination of the newly synthesized fragment with viral DNA.

It will be understood that the live attenuated PV according to the invention and/or any embodiment thereof, regardless of the additional presence of any further attenuation, such as e.g. an attenuated non-capsid region, can be obtained from all parvoviruses in which the Isoleucine/X1 and/or the Glutamine/X2 transition according to the invention in the capsid protein can be made, and thus at least from all now sequenced members of CPV and FPV. X1 and X2 are amino acids other than Isoleucine and Glutamine respectively.

It will also be understood that hybrid viruses comprising an FPV-capsid and a CPV-non-capsid backbone as well as hybrid viruses comprising a CPV-capsid and an FPV-non-capsid backbone are included in the invention and any embodiment thereof.

For example a live attenuated PV according to the invention and/or any embodiment thereof, comprising a non-capsid gene with a sequence as depicted in SEQ ID NO: 7 or coding for a non-capsid protein as depicted in SEQ ID NO: 8.

```
SEQ ID NO: 7: non-capsid gene
ATGTCTGGCAACCAGTATACTGAGGAAGTTATGGAGGGAGTAAATTGGT

TAAAGAAACATGCAGAAAATGAAGCATTTTCGTTTGTTTTTAAATGTGA

CAACGTCCAACTAAATGGAAAGGATGTTCGCTGGAACAACTATACCAAA

CCAATTCAAAATGAAGAGCTAACATCTTTAATTAGAGGAGCACAAACAG

CAATGGATCAAACCGAAGAAGAAGAAATGGACTGGGAATCGGAAGTTGA

TAGTCTCGCCAAAAAGCAAGTACAAACTTTTGATGCATTAATTAAAAAA

TGTCTTTTTGAAGTCTTTGTTTCTAAAAATATAGAACCAAATGAATGTG

TTTGGTTTATTCAACATGAATGGGGAAAAGATCAAGGCTGGCATTGTCA

TGTTTTACTTCATAGTAAGAACTTACAACAAGCAACTGGTAAATGGCTA

CGCAGACAAATGAATATGTATTGGAGTAGATGGTTGGTGACTCTTTGTT

CGGTAAACTTAACACCAACTGAAAAGATTAAGCTCAGAGAAATTGCAGA

AGATAGTGAATGGGTGACTATATTAACATACAGACATAAGCAAACAAAA

AAAGACTATGTTAAAATGGTTCATTTTGGAAATATGATAGCATATTACT

TTTTAACAAAGAAAAAAATTGTCCACATGACAAAAGAAAGTGGCTATTT

TTTAAGTACTGATTCTGGTTGGAAATTTAACTTTATGAAGTATCAAGAC

AGACAAATTGTCAGCACACTTTACACTGAACAAATGAAACCAGAAACCG

TTGAAACCACAGTGACGACAGCACAGGAAACAAAGCGCGGGAGAATTCA

AACTAAAAAGGAAGTGTCAATCAAATGTACTTTGCGGGACTTGGTTAGT

AAAAGAGTAACATCACCTGAAGACTGGATGATGTTACAACCAGATAGTT

ATATTGAAATGATGGCACAACCAGGAGGTGAAAATCTTTTAAAAAATAC

ACTTGAAATTTGTACTTTGACTTTAGCAAGAACAAAAACAGCATTTGAA

TTAATACTTGAAAAAGCAGATAATACTAAACTAACTAACTTTGATCTTG

CAAATTCTAGAACATGTCAAATTTTTAGAATGCACGGATGGAATTGGAT

TAAAGTTTGTCACGCTATAGCATGTGTTTTAAATAGACAAGGTGGTAAA

AGAAATACAGTTCTTTTTCATGGACCAGCAAGTACAGGAAATCTATCA

TTGCTCAAGCCATAGCACAAGCTGTGGGTAATGTTGGTTGTTATAATGC

AGCAAATGTAAATTTTCCATTTAATGACTGTACCAATAAAAATTTAATT

TGGATTGAAGAAGCTGGTAACTTTGGTCAACAAGTTAATCAATTTAAAG

CAATTTGTTCTGGACAAACAATTAGAATTGATCAAAAAGGTAAAGGAAG

TAAGCAAATTGAACCAACTCCAGTAATTATGACAACTAATGAAAATATA

ACAATTGTGAGGATTGGATGTGAAGAAAGACCTGAACATACACAACCAA

TAAGAGACAGAATGTTGAACATTAAGTTAGTATGTAAGCTTCCAGGAGA
```

-continued

```
CTTTGGTTTGGTTGATAAAGAAGAATGGCCTTTAATATGTGCATGGTTA

GTTAAACATGGTTATGAATCAACCATGGCTAACTATACACATCATTGGG

GAAAAGTACCAGAATGGGATGAAAACTGGGCGGAGCCTAAAATACAAGA

AGGTATAAATTCACCAGGTTGCAAAGACTTAGAGACACAAGCGGCAAGC

AATCCTCAGAGTCAAGACCAAGTTCACGTACGTATGACTCCGGACGTAG

TGGACCTTGCACTGGAACCGTGGAGTACTCCAGATACGCCTATTGCAGA

AACTGCAAATCAACAATCAAACCAACTTGGCGTTACTCACAAAGACGTG

CAAGCGAGTCCGACGTGGTCCGAAATAGAGGCAGACCTGAGAGCCATCT

TTACTTCTGAACAATTGGAAGAAGATTTTCGAGACGACTTGGATTAA
``` nonstructural protein

SEQ ID NO: 8

```
MSGNQYTEEVMEGVNWLKKHAENEAFSFVFKCDNVQLNGKDVRWNNYTK

PIQNEELTSLIRGAQTAMDQTEEEEMDWESEVDSLAKKQVQTFDALIKK

CLFEVFVSKNIEPNECVWFIQHEWGKDQGWHCHVLLHSKNLQQATGKWL

RRQMNMYWSRWLVTLCSVNLTPTEKIKLREIAEDSEWVTILTYRHKQTK

KDYVKMVHFGNMIAYYFLTKKKIVHMTKESGYFLSTDSGWKFNFMKYQD

RQIVSTLYTEQMKPETVETTVTTAQETKRGRIQTKKEVSIKCTLRDLVS

KRVTSPEDWMMLQPDSYIEMMAQPGGENLLKNTLEICTLTLARTKTAFE

LILEKADNTKLTNFDLANSRTCQIFRMHGWNWIKVCHAIACVLNRQGGK

RNTVLFHGPASTGKSIIAQAIAQAVGNVGCYNAANVNFPFNDCTNKNLI

WIEEAGNFGQQVNQFKAICSGQTIRIDQKGKGSKQIEPTPVIMTTNENI

TIVRIGCEERPEHTQPIRDRMLNIKLVCKLPGDFGLVDKEEWPLICAWL

VKHGYESTMANYTHHWGKVPEWDENWAEPKIQEGINSPGCKDLETQAAS

NPQSQDQVHVRMTPDVVDLALEPWSTPDTPIAETANQQSNQLGVTHKDV

QASPTWSEIEADLRAIFTSEQLEEDFRDDLD
```

Especially, when a vaccine specifically aims at the protection of dogs and cats against CPV and FPV respectively, the capsid gene of the virus according to the invention preferably encodes a capsid protein of CPV biotype 2a, 2b, 2c, or a genetic variant thereof, preferably of CPV biotype 2a, 2b or 2c, a genetic variant thereof, or a capsid protein of feline parvovirus. Further preferably, the capsid gene of the virus according to the invention encodes a capsid protein of CPV biotype 2c, or a genetic variant thereof. The genetic variant may be any variant originating from one of the CPV biotypes 2a, 2b or 2c, or any other CPV biotype known in the art, but carrying one or more mutations in the DNA encoding the capsid protein and resulting in one or more changes in the amino acid sequence. Attenuated PV of the present invention and embodiments thereof having a CPV biotype 2c background of the capsid gene, in addition to the amino acid position 219 and 386 of the capsid gene described above, is shown to provide an early onset of immunity, which can be achieved already at day five, at day four or even at day three, as surprisingly observed in the present invention. Thus, in a further preferred embodiment, the attenuated PV of the present invention and embodiments thereof comprises an amino acid other than Isoleucine at amino acid position 219 of the VP2 capsid protein and/or an amino acid other than a Glutamine at amino acid position 386 of the VP2 capsid protein, and the capsid gene of the virus encodes a capsid protein of CPV biotype 2c, or a genetic variant thereof.

As mentioned above, the non-capsid part of the parvovirus can either be of CPV or FPV origin. Therefore, an even further preferred form of this embodiment relates to live attenuated CPV according to the invention and/or any embodiment thereof, wherein the parvovirus encodes a capsid protein of CPV biotype 2a, 2b, 2c, or a genetic variant thereof, preferably CPV biotype 2a, 2b or 2c, most preferably of CPV biotype 2c, or a capsid protein of feline parvovirus.

Preferably, the live attenuated parvovirus according to the invention and/or any embodiment thereof, comprises a capsid gene coding at least one of the following amino acids: A Leucine at position 87, a Glycine at position 300, a Tyrosine at position 305, Aspartic acid or Glutamic acid at position 426 and Isoleucine or Valine at position 555 of the VP2 capsid protein. Preferably, the live attenuated parvovirus according to the invention and/or any embodiment thereof, comprises a capsid gene coding at least two, three, four or five of the following amino acids: A Leucine at position 87 a Glycine at position 300, a Tyrosine at position 305, Aspartic acid or Glutamic acid at position 426 and Isoleucine or Valine at position 555 of the VP2 capsid protein.

Preferably, the live attenuated parvovirus according to the invention and/or any embodiment thereof, comprises a capsid gene coding at least one of the following amino acids: A Leucine at position 87, a Glycine at position 300, a Tyrosine at position 305, a Glutamic acid at position 426 and a Valine at position 555 of the VP2 capsid protein. Preferably, the live attenuated parvovirus according to the invention and/or any embodiment thereof, comprises a capsid gene coding at least two, three, four or five of the following amino acids: A Leucine at position 87, a Glycine at position 300, a Tyrosine at position 305, aGlutamic acid at position 426 and Valine at position 555 of the VP2 capsid protein.

A preferred form of the parvovirus of the invention and/or any embodiment thereof relates to a live attenuated parvovirus according to the invention that comprises a capsid gene coding for an amino acid other than Isoleucine at amino acid position 219 of the VP2 capsid protein and an amino acid other than Glutamine at amino acid position 386 of the VP2 capsid protein and attenuating mutation in the non-capsid region, in the region from position 2062 to 2070.

A preferred form of the parvovirus of the invention and/or any embodiment thereof relates to a live attenuated parvovirus according to the invention that comprises a capsid gene coding for a Valine at amino acid position 219 of the VP2 capsid protein and a Lysine at amino acid position 386 of the VP2 capsid protein and attenuation mutation has the sequence corresponding to that of SEQ ID NO 1 of: ACG TAC GTA in the non-capsid region from position 2062 to 2070.

A preferred form of the parvovirus of the invention and/or any embodiment thereof relates to a live attenuated parvovirus according to the invention that comprises a capsid gene coding for an amino acid other than Isoleucine at amino acid position 219 of the VP2 capsid protein and an amino acid other than Glutamine at amino acid position 386 of the VP2 capsid protein and attenuating mutation in the non-capsid region, in the region from position 2062 to 2070 and wherein the parvovirus encodes a capsid protein of CPV biotype 2c.

A preferred form of the parvovirus of the invention and/or any embodiment thereof relates to a live attenuated parvovirus according to the invention that comprises a capsid gene coding for a Valine at amino acid position 219 of the VP2 capsid protein and a Lysine at amino acid position 386 of the VP2 capsid protein and attenuation mutation has the sequence corresponding to that of SEQ ID NO 1 of: ACG TAC GTA in the non-capsid region from position 2062 to 2070, and wherein the parvovirus encodes a capsid protein of CPV biotype 2c.

A preferred form of the parvovirus of the invention and/or any embodiment thereof relates to a live attenuated parvovirus according to the invention that comprises a capsid gene coding for an amino acid other than Isoleucine at amino acid position 219 of the VP2 capsid protein and an amino acid other than Glutamine at amino acid position 386 of the VP2 capsid protein and coding at least two, three, four or five of the following amino acids: a Leucine at position 87 a Glycine at position 300, a Tyrosine at position 305, Glutamic acid at position 426 and Valine at position 555 of the VP2 capsid protein and attenuating mutation in the non-capsid region from position 2062 to 2070.

A preferred form of the parvovirus of the invention and/or any embodiment thereof relates to a live attenuated parvovirus according to the invention that comprises a capsid gene coding for a Valine at amino acid position 219 of the VP2 capsid protein and a Lysine at amino acid position 386 of the VP2 capsid protein and coding at least two, three, four or five of the following amino acids: a Leucine at position 87 a Glycine at position 300, a Tyrosine at position 305, Glutamic acid at position 426 and Valine at position 555 of the VP2 capsid protein, and attenuation mutation has the sequence corresponding to that of SEQ ID NO 1 of: ACG TAC GTA in the non-capsid region from position 2062 to 2070.

For example a live attenuated PV according to the invention and/or any embodiment thereof, comprising a capsid gene with a sequence as depicted in SEQ ID NO: 9 or coding for a capsid protein as depicted in SEQ ID NO: 10 (VP1/2) and SEQ ID NO: 12 (VP2).

```
SEQ ID NO: 9: Capsid gene
ATGTGTTTTTTTATAGGACTTGTGCCTCCAGGTTATAAATATCTTGGGC

CTGGGAACAGTCTTGACCAAGGAGAACCAACTAACCCTTCTGACGCCGC

TGCAAAAGAACACGACGAAGCTTACGCTGCTTATCTTCGCTCTGGTAAA

AACCCATACTTATATTTCTCGCCAGCAGATCAACGCTTTATAGATCAAA

CTAAGGACGCTAAAGATTGGGGGGGGAAAATAGGACATTATTTTTTTAG

AGCTAAAAAGGCAATTGCTCCAGTATTAACTGATACACCAGATCATCCA

TCAACATCAAGACCAACAAAACCAACTAAAAGAAGTAAACCACCACCTC

ATATTTTCATTAATCTTGCAAAAAAAAAAAAAAGCCGGTGCAGGACAAGT

AAAAAGAGACAATCTTGCACCAATGAGTGATGGAGCAGTTCAACCAGAC

GGTGGTCAACCTGCTGTCAGAAATGAAAGAGCAACAGGATCTGGGAACG

GGTCTGGAGGCGGGGGTGGTGGTGGTTCTGGGGGTGTGGGGATTTCTAC

GGGTACTTTCAATAATCAGACGGAATTTAAATTTTTGGAAAACGGATGG

GTGGAAATCACAGCAAACTCAAGCAGACTTGTACATTTAAATATGCCAG

AAAGTGAAAATTATAGAAGAGTGGTTGTAAATAATTTGGATAAAACTGC

AGTTAACGGAAACATGGCTTTAGATGATACTCATGCACAAATTGTAACA

CCTTGGTCATTGGTTGATGCAAATGCTTGGGGAGTTTGGTTTAATCCAG

GAGATTGGCAACTAATTGTTAATACTATGAGTGAGTTGCATTTAGTTAG

TTTTGAACAAGAAATTTTTAATGTTGTTTTAAAGACTGTTTCAGAATCT
```

```
GCTACTCAGCCACCAACTAAAGTTTATAATAATGATTTAACTGCATCAT

TGATGGTTGCATTAGATAGTAATAATACTATGCCATTTACTCCAGCAGC

TATGAGATCTGAGACATTGGGTTTTTATCCATGGAAACCAACCATACCA

ACTCCATGGAGATATTATTTTCAATGGGATAGAACATTAGTACCATCTC

ATACTGGAACTAGTGGCACACCAACAAATATATACCATGGTACAGATCC

AGATGATGTTCAATTTTATACTATTGAAAATTCTGTGCCAGTACACTTA

CTAAGAACAGGTGATGAATTTGCTACAGGAACATTTTTTTTTGATTGTA

AACCATGTAGACTAACACATCACATGGCAAACAAATAGAGCATTGGGCTT

ACCACCATTTCTAAATTCTTTGCCTCAAGCTGAAGGAGGTACTAACTTT

GGTTATATAGGAGTTCAACAAGATAAAAGACGTGGTGTAACTCAAATGG

GAAATACAAACTATATTACTGAAGCTACTATTATGAGACCAGCTGAGGT

TGGTTATAGTGCACCATATTATTCTTTTGAGGCGTCTACACAAGGGCCA

TTTAAAACACCTATTGCAGCAGGACGGGGGGGGAGCGCAAACAGATGAAA

ATCAAGCAGCAGATGGTGATCCAAGATATGCATTTGGTAGACAACATGG

TAAAAAAACTACCACAACAGGAGAAACACCTGAGAGATTTACATATATA

GCACATCAAGATACAGGAAGATATCCAGAAGGAGATTGGATTCAAAATA

TTAACTTTAACCTTCCTGTAACAGAAGATAATGTATTGCTACCAACAGA

TCCAATTGGAGGTAAAACAGGAATTAACTATACTAATATATTTAATACT

TATGGTCCTTTAACTGCATTAAATAATGTACCACCAGTTTATCCAAATG

GTCAAATTTGGGATAAAGAATTTGATACTGACTTAAAACCAAGACTTCA

TGTAAATGCACCATTTGTTTGTCAAAATAATTGTCCTGGTCAATTATTT

GTAAAAGTTGCGCCTAATTTAACAAATGAATATGATCCTGATGCATCTG

CTAATATGTCAAGAATTGTAACTTACTCAGATTTTTGGTGGAAAGGTAA

ATTAGTATTTAAAGCTAAACTAAGAGCCTCTCATACTTGGAATCCAATT

CAACAAATGAGTATTAATGTAGATAACCAATTTAACTATGTACCAAGTA

ATATTGGAGGTATGAAAATTGTATATGAAAAATCTCAACTAGCACCTAG

AAAATTATATTAA
```

SEQ ID NO: 10: Capsid VP1/2 protein

```
MCFFIGLVPPGYKYLGPGNSLDQGEPTNPSDAAAKEHDEAYAAYLRSGK

NPYLYFSPADQRFIDQTKDAKDWGGKIGHYFFRAKKAIAPVLTDTPDHP

STSRPTKPTKRSKPPPHIFINLAKKKKAGAGQVKRDNLAPMSDGAVQPD

GGQPAVRNERATGSGNGSGGGGGGGSGGVGISTGTFNNQTEFKFLENGW

VEITANSSRLVHLNMPESENYRRVVVNNLDKTAVNGNMALDDTHAQIVT

PWSLVDANAWGVWFNPGDWQLIVNTMSELHLVSFEQEIFNVVLKTVSES

ATQPPTKVYNNDLTASLMVALDSNNTMPFTPAAMRSETLGFYPWKPTIP

TPWRYYFQWDRTLVPSHTGTSGTPTNIYHGTDPDDVQFYTIENSVPVHL

LRTGDEFATGTFFFDCKPCRLTHTWQTNRALGLPPFLNSLPQAEGGTNF

GYIGVQQDKRRGVTQMGNTNYITEATIMRPAEVGYSAPYYSFEASTQGP

FKTPIAAGRGGAQTDENQAADGDPRYAFGRQHGKKTTTTGETPERFTYI

AHQDTGRYPEGDWIQNINFNLPVTEDNVLLPTDPIGGKTGINYTNIFNT

YGPLTALNNVPPVYPNGQIWDKEFDTDLKPRLHVNAPFVCQNNCPGQLF
```

-continued

```
VKVAPNLTNEYDPDASANMSRIVTYSDFWWKGKLVFKAKLRASHTWNPI

QQMSINVDNQFNYVPSNIGGMKIVYEKSQLAPRKLY

Capsid VP2
                                      SEQ ID NO: 12
MSDGAVQPDGGQPAVRNERATGSGNGSGGGGGGGSGGVGISTGTFNNQT

EFKFLENGWVEITANSSRLVHLNMPESENYRRVVVNNLDKTAVNGNMAL

DDTHAQIVTPWSLVDANAWGVWFNPGDWQLIVNTMSELHLVSFEQEIFN

VVLKTVSESATQPPTKVYNNDLTASLMVALDSNNTMPFTPAAMRSETLG

FYPWKPTIPTPWRYYFQWDRTLVPSHTGTSGTPTNIYHGTDPDDVQFYT

IENSVPVHLLRTGDEFATGTFFFDCKPCRLTHTWQTNRALGLPPFLNSL

PQAEGGTNFGYIGVQQDKRRGVTQMGNTNYITEATIMRPAEVGYSAPYY

SFEASTQGPFKTPIAAGRGGAQTDENQAADGDPRYAFGRQHGKKTTTTG

ETPERFTYIAHQDTGRYPEGDWIQNINFNLPVTEDNVLLPTDPIGGKTG

INYTNIFNTYGPLTALNNVPPVYPNGQIWDKEFDTDLKPRLHVNAPFVC

QNNCPGQLFVKVAPNLTNEYDPDASANMSRIVTYSDFWWKGKLVFKAKL

RASHTWNPIQQMSINVDNQFNYVPSNIGGMKIVYEKSQLAPRKLY
```

A suitable form of the parvovirus according to the invention and/or any embodiment thereof comprises a live attenuated PV, comprising a capsid gene with a sequence that comprises 90%, 92%, 94%, 96%, or 98% sequence identity with the nucleotide sequence of SEQ ID NO: 9

A suitable form of the parvovirus according to the invention and/or any embodiment thereof comprises a live attenuated PV comprising a capsid gene coding for a capsid protein comprising an amino acid sequence that comprises 90%, 92%, 94%, 96%, or 98% sequence identity with the amino acid sequence in SEQ ID NO: 10 (VP1) or in SEQ ID NO: 12 (VP2).

A suitable form of the parvovirus according to the invention and/or any embodiment thereof comprises a live attenuated PV comprising a capsid gene with a sequence that comprises 95%, 97%, or 99% sequence identity with the nucleotide sequence of SEQ ID NO: 9.

A suitable form of the parvovirus according to the invention and/or any embodiment thereof comprises a live attenuated PV comprising a capsid gene coding for a capsid protein comprising an amino acid sequence that comprises 95%, 97%, or 99% sequence identity with the amino acid sequence in SEQ ID NO: 10 (VP1) or in SEQ ID NO: 12 (VP2).

A suitable form of the parvovirus comprises a live attenuated PV according to the invention and/or any embodiment thereof, comprising a capsid gene with a sequence that comprises 90%, 92%, 94%, 96%, or 98% sequence identity with the nucleotide sequence of SEQ ID NO: 9, wherein the capsid gene encodes an amino acid other than Isoleucine at amino acid position 219 of the VP2 capsid protein and an amino acid other than Glutamine at amino acid position 386 of the VP2 capsid protein.

A suitable form of the parvovirus comprises a live attenuated PV according to the invention and/or any embodiment thereof, comprising a capsid gene coding for a capsid protein comprising an amino acid sequence that comprises 90%, 92%, 94%, 96%, or 98% sequence identity with the amino acid sequence in SEQ ID NO: 10 (VP1) or in SEQ ID NO: 12 (VP2), wherein the capsid gene encodes an amino acid other than Isoleucine at amino acid position 219 of the VP2 capsid protein and an amino acid other than Glutamine at amino acid position 386 of the VP2 capsid protein.

A suitable form of the parvovirus comprises a live attenuated PV according to the invention and/or any embodiment thereof, comprising a capsid gene with a sequence that comprises 95%, 97%, or 99% sequence identity with the nucleotide sequence of SEQ ID NO: 9, wherein the capsid gene encodes an amino acid other than Isoleucine at amino acid position 219 of the VP2 capsid protein and an amino acid other than Glutamine at amino acid position 386 of the VP2 capsid protein.

A suitable form of the parvovirus comprises a live attenuated PV according to the invention and/or any embodiment thereof, comprising a capsid gene coding for a capsid protein comprising an amino acid sequence that comprises 95%, 97%, or 99% sequence identity with the amino acid sequence in SEQ ID NO: 10 (VP1) or in SEQ ID NO: 12 (VP2), wherein the capsid gene encodes an amino acid other than Isoleucine at amino acid position 219 of the VP2 capsid protein and an amino acid other than Glutamine at amino acid position 386 of the VP2 capsid protein.

A suitable form of the parvovirus comprises a live attenuated PV according to the invention and/or any embodiment thereof, comprising a capsid gene with a sequence that comprises 90%, 92%, 94%, 96%, or 98% sequence identity with the nucleotide sequence of SEQ ID NO: 9, wherein the capsid gene encodes a Valine at amino acid position 219 of the VP2 capsid protein and Lysine at amino acid position 386 of the VP2 capsid protein.

A suitable form of the parvovirus comprises a live attenuated PV according to the invention and/or any embodiment thereof, comprising a capsid gene coding for a capsid protein comprising an amino acid sequence that comprises 90%, 92%, 94%, 96%, or 98% sequence identity with the amino acid sequence in SEQ ID NO: 10 (VP1) or in SEQ ID NO: 12 (VP2), wherein the capsid gene encodes a Valine at amino acid position 219 of the VP2 capsid protein and a Lysine at amino acid position 386 of the VP2 capsid protein.

A suitable form of the parvovirus comprises a live attenuated PV according to the invention and/or any embodiment thereof, comprising a capsid gene with a sequence that comprises 95%, 97%, or 99% sequence identity with the nucleotide sequence of SEQ ID NO: 9, wherein the capsid gene encodes a Valine at amino acid position 219 of the VP2 capsid protein and a Lysine at amino acid position 386 of the VP2 capsid protein.

A suitable form of the parvovirus comprises a live attenuated PV according to the invention and/or any embodiment thereof, comprising a capsid gene coding for a capsid protein comprising an amino acid sequence that comprises 95%, 97%, or 99% sequence identity with the amino acid sequence in SEQ ID NO: 10 (VP1) or in SEQ ID NO: 12 (VP2), wherein the capsid gene encodes a Valine at amino acid position 219 of the VP2 capsid protein and a Lysine at amino acid position 386 of the VP2 capsid protein.

In a suitable embodiment of the invention and/or any embodiment thereof, the live attenuated PV comprises a capsid gene coding for a capsid protein wherein the capsid gene encodes an amino acid other than Lysine at amino acid position 93 of the VP2 capsid protein and/or an amino acid other than Lysine at amino acid position 219 of the VP2 capsid protein, and/or an amino acid other than Lysine at amino acid position 377 of the VP2 capsid protein, and/or an amino acid other than Serine at amino acid position 300 of the VP2 capsid protein, and/or an amino acid other than Alanine at amino acid position 301 of the VP2 capsid protein.

Another embodiment of the present invention relates to methods for the preparation of an attenuated a parvovirus according to the invention and any embodiments thereof, wherein such methods comprise exchanging a DNA fragment encoding at least part of the parvovirus capsid protein having at amino acid position 219 a codon encoding Isoleucine and/or having at amino acid position 386 a codon encoding Glutamine, by a DNA fragment encoding at least part of the parvovirus capsid protein having at amino acid position 219 a codon encoding an amino acid other than Isoleucine and/or having at amino acid position 386 a codon encoding an amino acid other than Glutamine.

Such exchanging of DNA can be done using recombinant DNA techniques well-known in the art, such as site-directed mutagenesis, exchange of restriction fragments and the like. There are several ways of making the 219 Isoleucine an X1 or 386 Glutamine an X2 substitution. Such changes could be introduced by chemical synthesis or PCR followed by recombination of the newly synthesized fragment with viral DNA.

A suitable method for producing the parvovirus of the present invention and/or embodiments thereof is preparing genetic material from a live attenuated parvovirus as defined herein, such as a plasmid encoding the genomic sequences for the parvovirus of the present invention and/or embodiments thereof. A suitable method is described in e.g. WO 2012/007589 and WO2011/107534. Plasmid DNA is then transfected into susceptible canine or feline cells such as A72 or CrFK cells in culture.

Transfections are performed using well known transfection techniques, such as Lipofectamine 2000 (Invitrogen). Following transfection, cells are passaged. Monitoring can be achieved by haemagglutination (HA) assay. Following transfection, cells may be passaged 1-20 times. Preferably the cells are passaged 5-15 times, preferably 2-16 times, preferably 1-10 times, preferably 10-20 times, more preferably 2-10 times, more preferably 2-5 times. Suitably the cells are 1, 2, 3, 4, 5, 6, 7, 8, 9, or 10 times passaged. Virus can thereafter be purified by any known method in the art.

Vaccinated Subject

When a vaccine is to be developed for the protection of animals, more specifically pets against parvovirus infection, the preferred parvovirus for use in such a vaccine would be a canine parvovirus (CPV) or a feline parvovirus (FPV). Thus, an even more preferred form of this embodiment relates to live attenuated parvovirus as described herein, wherein the parvovirus is a CPV or a FPV. Thus, the live attenuated parvovirus is administered in the present invention to an animal, which is preferably a pet, further preferably cat or dog, more preferably dog. Since in the present invention the single vaccination is performed during weeks 2-10, or 2-20 of age of the animal, the dog is also referred to herein as pup or puppy.

In another embodiment, the animal is housed as a single vaccinated animal. The animal is either housed as a single animal or within a group of non-vaccinated animals. The group of animals can be a litter, in which only one animal is vaccinated with the parvovirus of the present invention. The group of animals, such as the litter, typically also includes the mother animal. The size of the litter depends on the animal, such as the dog breed, and is typically between 2 and 10 animals, but may also be a group of 3, 4, 5, 6, 7, 8 or 9 animals. Typically, a pup will not leave the litter until 6-8 weeks of age and is vaccinated between four and eight weeks of age before leaving the litter. Hence, in a further embodiment, the present invention relates to a parvovirus as defined herein which is administered to an animal, such as a pup, which is housed within a group of animals, preferably a litter, and is vaccinated before leaving this group of animals. In this embodiment, vaccination is typically performed once during weeks 4-8 of the animal. Typical situation in the field is wherein the animal is vaccinated at age of 6-12 weeks and the animal just left or is leaving the litter. Another typical situation is that the animal is vaccinated at 2-10, or 2-20 weeks of age and will stay in the litter for at least 1 week, or even 2-4 weeks.

In another embodiment, the animal is housed in a group of two animals, such as two dogs, of which only one animal is vaccinated with the parvovirus of the present invention (also referred herein as "pair-housed" animal).

Protection Against Parvovirus Infection

The live attenuated PV as described herein is used in the protection of an animal against PV infection, wherein the PV is administered to the animal as a single dose and administered during weeks 2-20, or 2-12, especially as a single dose during weeks 2-10 of age of the animal. It has surprisingly been found in the present invention that with the live attenuated PV as described herein a single vaccination administered during weeks 2-20, or 2-12, such as during weeks 2-10 of age can provide an effective immune response for providing immunity against parvovirus infection. In addition, it has surprisingly found in the present invention that the live attenuated PV as described herein does not interfere with MDA. Thus, a single vaccination administered during weeks 2-20, 2-12, such as weeks 2-10, of age can provide an effective immune response for providing immunity against parvovirus infection irrespective of the animal's MDA level. Hence, an effective immune response can be achieved even in the presence of high levels of MDA, thus eliminating the need for multiple vaccinations. In addition, it has surprisingly been found that a single vaccination administered in weeks 2-20, or 2-12 of the age of the animal, preferably administered in 2-10 weeks, preferably administered in week 4-8 of age, or 6-8 weeks of age of the animal can provide sterilizing immunity already five days or four days, and even three days, following administration of the live attenuated PV and typically achieves an effective and long-term protection against PV infection.

Therefore, in a first aspect, the present invention provides a live attenuated parvovirus comprising a capsid gene, which is preferably of CPV2 biotype 2a, 2b or 2c, or a genetic variant thereof, further preferably CPV biotype 2c, or a genetic variant thereof, and coding for an amino acid other than Isoleucine at amino acid position 219 of the VP2 capsid protein and/or an amino acid other than Glutamine at amino acid position 386 of the VP2 capsid protein, for use in the protection of an animal against parvovirus infection wherein the live attenuated parvovirus is administered to the animal as a single dose and is administered during weeks 2-12, preferably during weeks 2-10, of age of the animal. Suitably, the live attenuated parvovirus of the present invention and/or embodiments thereof is administered to the animal as a single dose and is administered during weeks, 2-12, more suitably administered during weeks 2-10, more suitably administered during weeks 2-8, more suitably administered during weeks 2-6, more suitably administered during weeks 2-4, more suitably administered during weeks 4-10, more suitably administered during weeks 4-8, more suitably administered during weeks 4-6, more suitably administered during weeks 3-11, more suitably administered during weeks 3-9, more suitably administered during weeks 3-7, more suitably administered during weeks 3-5, more suitably administered during weeks 2-11, more suitably administered during weeks 2-9, more suitably administered during weeks 2-7, more suitably administered during weeks 2-5.

Also the present invention provides a live attenuated parvovirus comprising a capsid gene, which is preferably of CPV2 biotype 2a, 2b or 2c, or a genetic variant thereof, further preferably CPV biotype 2c, or a genetic variant thereof, and coding for an amino acid other than Isoleucine at amino acid position 219 of the VP2 capsid protein and/or an amino acid other than Glutamine at amino acid position 386 of the VP2 capsid protein, for use in the protection of an animal against parvovirus infection wherein the live attenuated parvovirus is administered to the animal as a single dose during weeks 2-20, preferably during weeks 2-15, of age of the animal.

"Single dose" means that the live attenuated parvovirus or the vaccine comprising the live attenuated parvovirus is given once, i.e., as a single vaccination. The single dose may be administered during e.g., weeks 2-20, or weeks 2-10 of age of the animal. The single dose may include, as vaccinating agent, only the live attenuated parvovirus of the present invention. In another embodiment, the single dose includes, as vaccinating agent, the live attenuated parvovirus of the present invention in combination with one or more vaccinating agent(s), i.e. the live attenuated parvovirus of the present invention is included in a combination vaccine, such as in combination with a distemper virus, such as a canine distemper virus (CDV), or any other virus or pathogen.

In certain cases, one or more than one additional vaccination can be given during weeks 11-20, e.g. during weeks 13-20, of age of the animal in order to prevent vaccine failures or as a booster vaccination in order to achieve an enhanced immune response and prolonged duration of immunity.

However, since the live attenuated parvovirus as described herein typically achieves an effective and long-term protection against parvovirus infection for at least three months, preferably for at least six months, more preferably for at least 12 months, even more preferably for at least three years, and most preferably lifelong, after a single vaccination which is administered during weeks 2,-20 or 2-12, e.g. during weeks 2-10, of age of the animal, additional vaccination is typically not necessary. Hence, in a preferred embodiment, the live attenuated parvovirus is administered to the animal once, i.e. as a single dose, during weeks 2-20 of age of the animal. In a further preferred embodiment, the live attenuated parvovirus is administered as a single dose to the animal between weeks 4-8 of age of the animal, particularly preferable at the age of weeks 5-6 of the animal, and most preferably at 6 weeks of age of the animal. Hence, the time of administration of the single dose may be at week 2, 3, 4, 5, 6, 7, 8, 9, 10, 11, 12, 13, 14, 15, 16, 17, 18, 19 or 20 of age, and may be chosen, for example, depending on the animal, such as dog breed, or depending on the housing situation of the animal.

It has surprisingly been found in the present invention that a single vaccination with the live attenuated parvovirus effectively stimulates active immunity against parvovirus infection, and thus may achieve production of antibodies providing protection against parvovirus infection.

Typically, the onset of immunity is achieved at day five or earlier, preferably at day four or earlier, and preferably at day three or earlier, following administration of the attenuated PV vaccine described herein. Hence, even single vaccination of the animal with the live attenuated parvovirus as described herein effectively provides protection against parvovirus infection already at an early stage following vaccination.

In the prior art, vaccination against Parvovirus usually required, at least 2 or even 3 doses. See e.g. WO2014/095956 which discloses an attenuated type 2c canine parvovirus. A vaccine with the attenuated type 2c parvovirus is administered to 20 puppies between 6-8 weeks of age, in 2 doses 3 weeks apart.

A further advantage of the live attenuated parvovirus as described herein is that the presence of maternally derived antibodies (MDA) in the animal does typically not interfere with the efficacy of the treatment. Hence, a reliable immune response and protection of the animal against parvovirus infection can be achieved independent from the animal's MDA level. Therefore, vaccination with the live attenuated parvovirus as described herein minimizes the risk of vaccine failure in the presence of residual MDA. Further, since protection against parvovirus infection can be achieved irrespective of the animal's MDA level, it is typically not necessary to determine the animal's MDA level before vaccination, e.g. by determining the animal's hemagglutinin inhibition (HAI) titre of MDA. Therefore, in the present invention, administration of the live attenuated parvovirus can be performed independent from the animal's pre-vaccination HAI titre of MDA measured at time of vaccination.

In particular, it has surprisingly been observed in the present invention that an immune response providing protection against parvovirus infection in the animal can be achieved even if the animal's pre-vaccination HAI titre of MDA measured at time of vaccination is higher than 128 or 288, preferably higher than 576, even more preferably higher than 1152, most preferably higher than 1664, as determined by a method as described in the experimental section. Preferably, the pre-vaccination HAI titre of maternally derived antibody measured at time of vaccination is between 0-2000, preferably between 100 and 1800, preferably between 200 and 1600, preferably between 300 and 1400, preferably between 400 and 1200, preferably between 500 and 1000, preferably between 600 and 900 and preferably between 700 and 800. Therefore, it could surprisingly be shown in the present invention that protection against parvovirus infection can be achieved even in the presence of high levels of MDA, which has not been possible with the vaccines of the prior art.

Levels or titres of MDA can be measured by the Haemagglutination inhibition (HAI) assay. HAI measures the ability of serum CPV antibodies within the sample to inhibit the agglutination of pig red blood cells by CPV. Antibodies to CPV can be determined by HAI assay according to Carmichael, L. E. et al., Am J Vet Res 1980; 41 (5):78-791; Churchill A. E., J Bio Standardization 1982; 10(1):1-8.

An onset of immunity at day five or earlier, such as at day three, is typically achieved in the absence of MDA, which can be considered as an MDA level below a HAI titre of 8, preferably below 16, further preferably below 64, determined at the time of vaccination.

In addition, it could be observed that an immune response providing protection against parvovirus infection in pair-housed animals, of which only one animal is vaccinated (i.e. without shedding and spreading of virus between animals), can be achieved even if the animal's pre-vaccination HAI titre of MDA measured at time of vaccination is higher than 128, or higher than 288 or even higher than 576.

Further, it could be observed that an immune response providing protection against parvovirus infection in group-housed animals, of which more than one animal is vaccinated (i.e. two or more animals, allowing shedding and spreading of the vaccine virus between animals), can be achieved even if the animal's pre-vaccination HAI titre of MDA measured at time of vaccination is higher than 1152 or even higher than 1664.

Hence, vaccination of the animal with the live attenuated parvovirus as described herein effectively provides protection against parvovirus infection already at an early stage following a single vaccination and can even achieve protection against parvovirus infection in the presence of MDA.

In consequence, in a second aspect, the present invention provides a live attenuated parvovirus (PV), comprising a capsid gene, which is preferably of CPV2 biotype 2a, 2b or 2c, or a genetic variant thereof, further preferably CPV biotype 2c, or a genetic variant thereof, and coding for an amino acid other than Isoleucine at amino acid position 219 of the VP2 capsid protein and/or an amino acid other than Glutamine at amino acid position 386 of the VP2 capsid protein, for use in the protection of an animal against parvovirus infection, wherein administration is performed independent from the animal's pre-vaccination HAI titre of MDA measured at time of vaccination.

In a third aspect, the present invention provides a live attenuated parvovirus (PV), comprising a capsid gene, which is preferably of CPV2 biotype 2a, 2b or 2c, or a genetic variant thereof, further preferably CPV biotype 2c, or a genetic variant thereof, and coding for an amino acid other than Isoleucine at amino acid position 219 of the VP2 capsid protein and/or an amino acid other than Glutamine at amino acid position 386 of the VP2 capsid protein, for use in the protection of an animal against parvovirus infection, wherein the animal's pre-vaccination HAI titre of MDA measured at time of vaccination is higher than 128, or higher than 288, preferably higher than 576.

In a particularly preferred embodiment of the present invention and/or embodiments thereof, the live attenuated parvovirus is administered to the animal between weeks 2-7 of age of the animal, preferable at the age of weeks 4-6 of the animal particularly preferable at the age of weeks 5-6 of the animal, and most preferably at the age of 6 weeks, even if the animal's pre-vaccination HAI titre of MDA measured at time of vaccination is higher than 128 or higher than 288, even higher than 576, even higher than 1152.

A further surprising observation in the present invention is that protection against parvovirus infection can be achieved after administration of the live attenuated parvovirus as described herein even in case the animal, preferably the dog, is housed as a single vaccinated animal.

A live attenuated parvovirus administered to an animal for vaccination is typically excreted in the faeces of the animal for up to 8 days after vaccination. Occasionally, this virus can spread to other animals via faecal-oral route but without causing clinical signs of disease. Usually, when a vaccine against parvovirus infection is tested in the art, the animals, such as puppies, are housed in a group of more than two animals, e.g. 5-10 animals, in a single room. In this situation, even if only one animal of the group of animals is vaccinated with a live attenuated parvovirus, the vaccine virus is shed from the vaccinated individual via the faeces to the other co-housed animals. Since dogs have a naturally inquisitive nature, the virus is easily ingested and the other dogs in the room are vaccinated by proxy. If more than one animal in the room was vaccinated, the already vaccinated animals get a booster vaccination by ingesting the virus from the faeces from the other vaccinated individuals. Since the virus is very stable and the dogs are continuously exposed to the vaccine virus excreted in the faeces from their roommates, their immune system receives a sustained boost over multiple days. As the level of MDA drops over time in those dogs for which the initial vaccination did not work, once it reaches a sufficiently low level the vaccine strain picked up from the environment is able to artificially break through any residual MDA and induce active immunity. However, this method of testing vaccine efficacy in a group of animals typically does not represent the situation in the field, in which a new pet, such as a puppy, is normally housed by the pet owner as a single animal, and thus without the possibility of spread of vaccine virus from other recently vaccinated animals.

For example, WO2014/095956 discloses an attenuated type 2c canine parvovirus. A vaccine with the attenuated type 2c parvovirus is administered to 20 puppies between 6-8 weeks of age, in 2 doses 3 weeks apart. In this group all 20 puppies have received the vaccination. The live parvo strain of the vaccine will have been shed in the faeces and ingested by the puppies in the vaccine group.

In the present invention, it has been found that an immune response achieving protection against parvovirus infection can be achieved by administration of the live attenuated parvovirus to the animal, which is housed as a single vaccinated animal, such as dog, during a period of at least two weeks after administration of the live attenuated parvovirus. Thus, protection against parvovirus infection can be achieved even in the absence of other animals, such as other vaccinated animals, which might shed the virus to the animal via their faeces. Hence, in the present invention, a booster vaccination, such as a booster vaccination achieved via contact with the faeces of other animals, is not necessary. This method of housing more accurately reflects the biologically isolated setting that most young pups encounter after they have transitioned from their litter to a permanent home.

The animal is typically housed as a single vaccinated dog, preferably as a single dog, during a period of at least two weeks after administration of the live attenuated parvovirus. Further, preferably, the animal is housed as a single vaccinated dog, preferably as a single dog, during a period of at least three weeks, further preferably of at least four weeks, after administration of the live attenuated parvovirus. In an alternative embodiment, the animal is housed as a vaccinated animal within a group of one, two, three or more other vaccinated animals. The presence of other vaccinated animals allows the virus to shed and spread to the animal e.g. via their faeces to result in booster vaccinations leading to a faster increase in immunity and enhanced protection against PV infection. Thus, in this embodiment a booster vaccination, such as one or more than one additional vaccination during weeks 11-20, e.g. during weeks 13-20, is typically not necessary to achieve protection against PV infection. In consequence, it is a further preferred embodiment that the animal is housed as a vaccinated animal within a group of one, two, three or more other vaccinated animals and the live attenuated PV is administered to the animal once, i.e. as a single dose, during weeks 2-20 of age of the animal.

It was further found that the live attenuated parvovirus of the present invention and embodiments thereof provided protection in animals that are grouped with at least one other vaccinated animal, i.e. allowing shed and spread of the vaccine virus, wherein the MDA level are particularly high, such as HAI titre higher than 576, even higher than 1152, or even higher than 1664.

Thus, in a fourth aspect, the present invention provides a live attenuated parvovirus comprising a capsid gene, which is preferably of CPV2 biotype 2a, 2b or 2c, or a genetic variant thereof, further preferably CPV biotype 2c, or a genetic variant thereof, and coding for an amino acid other than Isoleucine at amino acid position 219 of the VP2 capsid protein and/or an amino acid other than Glutamine at amino acid position 386 of the VP2 capsid protein, for use in the protection of an animal against parvovirus infection, wherein the animal, preferably dog, is housed as a single vaccinated animal during a period of at least two weeks after administration of the live attenuated PV.

It has further surprisingly been observed that vaccination with the live attenuated parvovirus of the present invention achieves a rapid immune response, even in the presence of MDA, and can achieve a protection against parvovirus infection already at day five, preferably at day four, and more preferably at day three, following vaccination. The time at which immunity against infection after vaccination is achieved is also designated herein as "onset of immunity".

Therefore, in a fifth aspect, the present invention provides a live attenuated parvovirus (PV), comprising a capsid gene, which is preferably of CPV2 biotype 2a, 2b or 2c, or a genetic variant thereof, further preferably CPV biotype 2c, or a genetic variant thereof, and coding for an amino acid other than Isoleucine at amino acid position 219 of the VP2 capsid protein and/or an amino acid other than Glutamine at amino acid position 386 of the VP2 capsid protein, for use in the protection of an animal against parvovirus infection, wherein the animal's onset of immunity is achieved at day five, preferably at day four and, preferably, is achieved at day three after administration of the live attenuated PV.

Further, it could be observed that the onset of immunity after vaccination with the PV vaccine of the present invention may depend on the MDA level of the vaccinated animal. Typically, a three-day onset of immunity can be achieved in case the MDA level is below 288 HAI unity, and preferably is below 576 HAI units. A five-day onset of immunity can be achieved in case the MDA level is below 832 HAI units, and preferably is below 1152 HAI units or even below 1664 HAI units.

The present invention further encompasses any combinations of the first, second, third, fourth and/or fifth aspect of the present invention. Hence, in embodiments of the present invention, there is provided a live attenuated parvovirus as described herein, for use in the protection of an animal against parvovirus infection, wherein one or more of the following (1) to (5) applies:

(1) wherein the live attenuated parvovirus is administered to the animal as a single dose and is administered during weeks 2-12, preferably during weeks 2-10 of age of the animal, more preferably during weeks, 4-8 of age of the animal, most preferably during weeks 5-6 of age of the animal, and/or (2) wherein administration is performed independent from the animal's pre-vaccination HAI titre of maternally derived antibody (MDA) measured at time of administration of the live attenuated PV, and/or (3) wherein the animal's pre-vaccination HAI titre of maternally derived antibody (MDA) measured at time of administration of the live attenuated PV is higher than 128, or higher than 288, preferably higher than 576, further preferably higher than 1152, and/or (4) wherein the animal is housed as a single vaccinated animal or as single vaccinated animal in a group of two or more animals that are not vaccinated, and/or (5) wherein the animal's onset of immunity is achieved at day five, preferably at day four and, further preferably, is achieved at day three after administration of the live attenuated PV.

Vaccine for Use in the Protection of an Animal Against Parvovirus Infection

The present invention further provides a vaccine comprising the live attenuated parvovirus as described herein for use in the protection of an animal against parvovirus infection, further comprising a pharmaceutically acceptable carrier.

A suitable amount of parvovirus for use in the vaccine according to the invention would in many cases be within the range of $10^3$-$10^9$ $TCID_{50}$, depending on the level of attenuation and the replication characteristics of the virus. An infectious dose of virus that is below $10^3$ $TCID_{50}$ would in many cases considered to be too low, since it would take too much time for the virus to replicate to a sufficiently high level to trigger the immune system and overcome maternally derived antibody. Amounts that exceed $10^9$ $TCID_{50}$ would be unattractive, if only for commercial reasons. A very suitable dose would be in the range of $10^5$-$10^8$ $TCID_{50}$, even better between $10^5$ to $10^7$ or $10^6$-$10^8$ $TCID_{50}$. A preferred dose of the live attenuated parvovirus is administered to the animal with a dose from $10^{5.1}$-$10^{6.7}$ $TCID_{50}$ or $10^{4.7}$-$10^{6.7}$ $TCID_{50}$.

Pharmaceutically acceptable carriers are well-known in the art. Merely as an example; such a carrier can be as simple as sterile water or a buffer solution such as PBS. The vaccine may comprise a single carrier of a combination of two or more carriers.

Vaccines according to the invention can be administered in several ways. Since the vaccine comprises a live attenuated virus, many ways of administration, such as oral, intranasal, intramuscular, and subcutaneous administration are feasible. A preferred route of administration is the subcutaneous administration and the oral administration.

Animals susceptible to parvovirus infection such as i.a. cats and dogs are frequently vaccinated against several other diseases at the same time. Therefore, it would be practical to combine a vaccine according to the invention with an additional antigen of a virus or micro-organism pathogenic to dogs and cats or genetic information encoding said antigen.

Thus, another embodiment of the invention relates to a combination vaccine comprising a vaccine according to the invention and an additional antigen of a virus or micro-organism pathogenic to animals or genetic information encoding an immunogenic polypeptide of said virus or micro-organism.

The additional antigen of a virus or a micro-organism can be the whole virus or micro-organism (in a live attenuated form or in an inactivated form) or an immunogenic polypeptide or another immunogenic part of that virus or micro-organism such as e.g. a (lipo-)polysaccharide, capable of inducing a protective immune response.

Preferably, the virus or micro-organism pathogenic to animals is selected from the group of *Ehrlichia canis, Babesia gibsoni, vogeli, rossi, Leishmania donovani*-complex, Canine adenovirus type 1, Canine adenovirus type 2, Canine coronavirus, Canine distemper virus, *Leptospira interrogans* serovar canicola, *Leptospira interrogans* serovar icterohaemorrhagiae, *Leptospira interrogans* serovar pomona, *Leptospira interrogans* serovar grippotyphosa, *Leptospira interrogans* serovar bratislava, Canine hepatitis virus, Canine parainfluenza virus, rabies virus, *Hepatozoon canis, Borrelia burgdorferi, Bordetella bronchiseptica*, feline Herpesvirus, feline calicivirus, feline panleukopenia, feline leukemia, *Chlamydophila felis*, and corona virus, such as SARS-CoV-2 (covid-19).

In a preferred embodiment, said virus or micro-organism pathogenic to animals is a live attenuated canine distemper virus, such as a canine distemper virus strain Onderstepoort.

A suitable amount of the live attenuated canine distemper virus is administered to the animal with a dose as described above for the live attenuated canine parvovirus, and preferably is administered to the animal at a dose from $10^{5.1}$-$10^{6.5}$ $TCID_{50}$.

Vaccines comprising live attenuated viruses are usually stored at low temperature or are in a freeze-dried form. Freeze-dried vaccines can be kept under moderate cooling conditions or even at room temperature. Often, the vaccine antigen is mixed with stabilizers, e.g. to protect degradation-prone proteins from being degraded, to enhance the shelf-life of the vaccine, to improve freeze-drying efficiency, or to improve the appearance of the product. Useful stabilizers are i.a. SPGA, carbohydrates e.g. sorbitol, mannitol, trehalose, starch, sucrose, dextran or glucose, proteins such as gelatin, albumin or casein or degradation products thereof, and buffers, such as alkali metal phosphates.

In another aspect, the invention relates to a liquid vaccine composition comprising the live attenuated parvovirus of the present invention and a pharmaceutically acceptable carrier, wherein the carrier is a natural deep-eutectic solvent (NA-DES) having a water activity of less than about 0.8. The NADES carrier is described in WO 2019/122329, which is hereby incorporated by reference in its entirety.

Therefore, preferably, the (combination) vaccine according to the invention is in a freeze-dried form, i.e. is provided as a lyophilizate.

In addition, the vaccine may be suspended in a physiologically acceptable diluent with or without adjuvant. Such buffers can e.g. be sterile water, a buffer, and the like.

It goes without saying, that diluents and compounds for emulsifying or stabilizing viruses are also embodied in the present invention.

A particularly preferred combination of excipients in the vaccine according to the invention is hydrolysed gelatin, casein, sorbitol, and disodium phosphate dihydrate.

The vaccine according to the invention may be provided in the form of a kit comprising the lyophilized vaccine as described above and a solvent. The solvent is not particularly restricted and may be any solvent typically used for administration of a vaccine, such as water for injection or PBS, and may comprise one or more excipients, such as salts and/or buffers. Preferably, the solvent comprises disodium phosphate dihydrate, potassium dihydrogen phosphate and water for injection. Further preferably, the kit comprises the lyophilizate and a solvent, wherein the lyophilizate is reconstituted with the solvent before administration.

Method of Manufacture and Use of the Vaccine of the Invention

Again another embodiment of the invention relates to methods for the manufacture of a (combination) vaccine according to the invention wherein these methods comprise the mixing of a live attenuated parvovirus as described herein and a pharmaceutically acceptable carrier.

Still another embodiment of the invention relates to live attenuated parvovirus as described herein for use as a medicament. More specifically, the present invention relates to live attenuated parvovirus for use in the treatment of parvovirus infection. Again another embodiment of the present invention relates to the use of a live attenuated parvovirus as described herein for the treatment of parvovirus infection.

The method of manufacture of a vaccine as described above may comprise the steps of:

(1) transfection of cells with the genetic material from the live attenuated parvovirus as described herein and culturing of the cells under conditions that allow the production of the live attenuated parvovirus, wherein the method comprises at most two passages of the virus to another cell culture following transfection, (2) isolation of the live attenuated parvovirus from the cell culture, and (3) mixing the live attenuated parvovirus with a pharmaceutically acceptable carrier.

The present invention further relates to a vaccine obtainable by the above-described method of manufacture.

Another embodiment is a method of protecting an animal against parvovirus infection comprising administering a live attenuated parvovirus comprising a capsid gene coding for an amino acid other than Isoleucine at amino acid position 219 of the VP2 capsid protein and/or an amino acid other than Glutamine at amino acid position 386 of the VP2 capsid protein as a single dose to the animal, and administering this single dose during weeks 2-12, preferably during weeks 2-10, of age of the animal.

Another embodiment is a method of protecting an animal against parvovirus infection comprising administering a live attenuated parvovirus comprising a capsid gene coding for an amino acid other than Isoleucine at amino acid position 219 of the VP2 capsid protein and/or an amino acid other than Glutamine at amino acid position 386 of the VP2 capsid protein to the animal, wherein the administration is performed independent from the animal's pre-vaccination HAI titre of maternally derived antibody (MDA) measured at time of vaccination.

Another embodiment is a method of protecting an animal against parvovirus infection comprising administering a live attenuated parvovirus comprising a capsid gene coding for an amino acid other than Isoleucine at amino acid position 219 of the VP2 capsid protein and/or an amino acid other than Glutamine at amino acid position 386 of the VP2 capsid protein to the animal wherein the animal's pre-vaccination HAI titre of maternally derived antibody (MDA) measured at time of vaccination is higher than 128 or higher than 288, preferably higher than 576, further preferably higher than 1152.

Another embodiment is a method of protecting an animal against parvovirus infection comprising administering a live attenuated parvovirus comprising a capsid gene coding for an amino acid other than Isoleucine at amino acid position 219 of the VP2 capsid protein and/or an amino acid other than Glutamine at amino acid position 386 of the VP2 capsid protein to the animal wherein the animal is housed as a single vaccinated animal, or as single vaccinated animal in a group of two or more animals wherein the other animals are not vaccinated.

Another embodiment is a method of protecting an animal against parvovirus infection comprising administering a live attenuated parvovirus comprising a capsid gene coding for an amino acid other than Isoleucine at amino acid position 219 of the VP2 capsid protein and/or an amino acid other than Glutamine at amino acid position 386 of the VP2 capsid protein to the animal wherein the animal's onset of immunity is achieved at day five, preferably at day four and, further preferably, is achieved at day three after vaccination.

EXAMPLES

The present invention can further be described by the following non-limiting Examples.

Vaccine

The live attenuated parvovirus used in the Experiments of the following Examples is parvovirus clone 630att described in Example 1 of WO2012/007589. A vaccine comprising parvovirus clone 630att (abbreviated in the following as "CPV 630a") was prepared by transfection of A72 cells, with an additional two passes in A72 cells, which resulted in generated virus, which was administered to pups. FIG. 1 shows the nucleotide sequence of CPV 630a (SEQ ID NO: 11). The nucleotide sequence of the non-capsid gene (non-structural gene) (SEQ ID NO: 7) and the amino acid sequences of the non-capsid protein (SEQ ID NO: 8) as well as nucleotide sequence of the capsid gene (Capsid VP1/2) (SEQ ID NO: 9) and the amino acid sequence of capsid protein (SEQ ID NO: 10) are also indicated. The attenuating sequence in the nonstructural gene at nucleotide 2062-2070 is also indicated ("Hotspot") (see also SEQ ID NO: 1). In the Capsid, amino acid 87, 110, 297, 300, 305, 375, 426 as well as the mutation of amino acid 219 Isoleucine to valine, and amino acid 386 glutamine to lysine are indicated.

Challenge Material

Canine Parvovirus Challenge Virus (MSD Animal Health, NL)

Virus: Canine Parvovirus type 2c Italian Field Strain

Methods and Procedure:

If not indicated otherwise, the following methods and procedures were used.

Administration

Vaccination was carried out by subcutaneous inoculation into the scruff of the neck in the center of the midline. Subcutaneous injection is the standard route of vaccination in dogs.

Each pup was challenged orally with a CPV-2c Italian field virus. Oral challenge mimics the natural transmission of canine parvovirus and is in line with the route recommended in the European Pharmacopoeia monograph 0964.

Serological Analysis:

Blood samples were separated, and the serum was heat inactivated at 56° C. for thirty to sixty minutes in a water bath prior to testing.

Canine Parvovirus Haemagglutination Inhibition (HAI):

Haemagglutination inhibition (HAI) measures the ability of serum CPV antibodies within the sample to inhibit the agglutination of pig red blood cells by CPV. Antibodies to CPV were determined by HAI assay according to Carmichael, L. E. et al., Am J Vet Res 1980; 41 (5):78-791; Churchill A. E., J Bio Standardization 1982; 10(1):1-8. Briefly, dilutions of sera were incubated with 8 HA units of CPV on a 96 well plate at 37° C. for 1 hour. The plates were incubated at 2-8° C. for 15 to 20 minutes and then 1% pig red blood cells added and incubated at 2-8° C. for approximately 2 hours. The inhibition of Haemagglutination was characterized by tear-dropping of the pig blood cells. The HAI titre of the sample was the reciprocal of the last dilution at which inhibition of agglutination occurred (50% agglutination).

Each serum sample was tested against CPV 2a, CPV 2b and CPV 2c biotypes and expressed against 4 HAI units of antigen.

Canine Parvovirus Serum Neutralisation (SN):

For selected timepoints, antibodies to CPV were also determined by serum neutralisation (SN) against 2a, 2b and 2c biotypes.

The SN assay measures the ability of antibodies within a serum sample to neutralise virus and prevent the infection of cells in culture. Briefly, dilutions of sera were incubated at 37° C. for one hour with 100-300 $TCID_{50}$/ml virus on a 96 well plate. A72 cells were added and incubated for three days. CPV was detected by immunofluorescence with a CPV specific MAb and anti-mouse IgG-FITC. The virus neutralising antibody titre ($SN_{50}$) was calculated as the reciprocal of the highest dilution of the serum that shows neutralisation of the virus.

Virus Isolation:

In order to obtain a semi-quantitative estimate of the amount of virus present in the rectal swabs, isolations were repeated on serial dilutions of the swab transport fluid. In order to differentiate between the shedding of vaccine virus and challenge virus in the vaccinated dogs, the Day +8 rectal swabs were examined by PCR. Swab samples were filtered and analysed with both generic CPV primers and PCR primers specific for the vaccine or equivalent field virus sequence.

Virus Isolation from Rectal Swabs:

Virus isolation by growth in tissue culture was performed for all rectal swab samples. The swab supernatants were plated out in duplicate using 5-fold dilutions and assayed by immunofluorescence on A72 cells with a CPV specific MAb and an anti-mouse-IgG-FITC.

PCR Analysis of Rectal Swab Material Using Differential Primer Sets:

The swab material was removed and filtered. 200 µl of the filtered supernatant was used in the MagNA Pure automated nucleic acid extraction robot from Roche with standard procedures and according to manufacturer's instructions.

Post PCR the reactions were run on an agarose/ethidium bromide gel alongside a DNA marker. Following electrophoresis the gel was visualised on a gel doc imaging instrument. Samples were considered positive if they gave a visible band size of the correct size. The PCR test was considered valid if the relevant positive control also gave a visible band of the correct size and there was no evidence of amplification with the negative control.

Clinical Monitoring:

All dogs were observed daily for clinical signs including rectal temperature and body weight. Clinical signs were recorded daily, and scores assigned to each clinical condition.

Example 1

Objective of the study was to investigate the early onset of immunity in CPV 630a vaccinated pups.

Study Design

Twenty-one SPF Beagle dogs of approximately 10 weeks of age and devoid of maternally derived antibodies were divided into seven groups of three dogs. Each dog in Groups 1, 2, 3, 4, 5 and 6 was vaccinated with the appropriate test article by subcutaneous inoculation.

Group 1: parvovirus 630a at a dose of $10^{5.0}$ $TCID_{50}$
Group 2: parvovirus 630a at a dose of $10^{5.5}$ $TCID_{50}$
Group 3: parvovirus 630a at a dose of $10^{6.0}$ $TCID_{50}$
Group 4: parvovirus 630a at a dose of $10^{5.0}$ $TCID_{50}$
Group 5: parvovirus 630a at a dose of $10^{5.5}$ $TCID_{50}$
Group 6: parvovirus 630a at a dose of $10^{6.0}$ $TCID_{50}$
Group 7: Unvaccinated controls All dogs were challenged with CPV-2c Italian field virus. The vaccinations were staggered so that the challenge fell three days after the vaccination of Groups 1, 2 and 3, and five days after the vaccination of Groups 4, 5 and 6.

Animals were observed for clinical signs and were weighed daily. Rectal swabs were taken to monitor viral excretion and rectal temperatures were taken daily. Blood samples were taken to monitor the serological response to vaccination and/or challenge.

All dogs were bled for serology on days 0, 5, 7, 11/12 and 28. Groups 1, 2, 3 and 7 were additionally bled on day 2. Animals were monitored for local and systemic adverse reactions.

Materials

Vaccine: Live attenuated canine parvovirus 630a

Challenge virus: CPV-2c (Italian Isolate)

Test System

SPF Beagle dogs, ~10 weeks of age (both male and female)

Method of Vaccination

All dogs, except those in Group 7, were vaccinated with the appropriate test material by subcutaneous inoculation.

CPV Challenge

The CPV-2c Italian field virus was orally administered at a dose of $10^{5.5}$ TCID$_{50}$.

Results

Haemagglutiation Inhibition (HAI) response values are shown in Table 1 below. Serum Neutralisation (SN) values are shown in Table 2 below. The results shown are those measured against CPV-2c antigen.

TABLE 1

HAI response values

| | | | 0 Vaccination | +2 Vaccination | +5 Challenge | +7 | +11/+12 | +28 |
|---|---|---|---|---|---|---|---|---|
| 3 day OOI | Group 1 $10^5$ | #1 | — | <8 | 32 | 2048 | 20480 | 10240 |
| | | #2 | — | <8 | <8 | 2048 | 20480 | 10240 |
| | | #3 | — | <8 | 64 | 4096 | 20480 | 20480 |
| | Group 2 $10^{5.5}$ | #4 | — | <8 | 64 | 2048 | 20480 | 10240 |
| | | #5 | — | <8 | 64 | 4096 | 20480 | 10240 |
| | | #6 | — | <8 | <8 | 2048 | 20480 | 10240 |
| | Group 3 $10^6$ | #7 | — | <8 | 32 | 4096 | 20480 | 10240 |
| | | #8 | — | <8 | 64 | 2048 | 20480 | 10240 |
| | | #9 | — | <8 | 64 | 4096 | 20480 | 10240 |
| | Group 4 $10^5$ | #10 | <8 | — | 2048 | 10240 | 10240 | 10240 |
| | | #11 | <8 | — | 4096 | 10240 | 20480 | 10240 |
| | | #12 | <8 | — | 4096 | 5120 | 20480 | 10240 |
| 5 day OOI | Group 5 $10^{5.5}$ | #13 | <8 | — | 2048 | 10240 | 20480 | 20480 |
| | | #14 | <8 | — | 4096 | 10240 | 20480 | 20480 |
| | | #15 | <8 | — | 4096 | 5120 | 20480 | 10240 |
| | Group 6 $10^6$ | #16 | <8 | — | 4096 | 20480 | 20480 | 10240 |
| | | #17 | <8 | — | 8184 | 20480 | 20480 | 10240 |
| | | #18 | <8 | — | 8184 | 20480 | 20480 | 10240 |
| Controls | Group 7 | #19 | <8 | <8 | <8 | NT | 5120 | * |
| | | #20 | 64 | 64 | 64 | NT | 5120 | * |
| | | #21 | <8 | <8 | <8 | NT | 10240 | * |

* Euthanised

TABLE 2

SN response values

| | | | 0/+2 Vaccination | +5 Challenge | +7 | +11/+12 | +28 |
|---|---|---|---|---|---|---|---|
| 3 day OOI | Group 1 $10^5$ | #1 | <14 | <14 | 3200 | 32254 | 40637 |
| | | #2 | <14 | <14 | 3200 | 32254 | 64508 |
| | | #3 | <14 | <20 | 6400 | 32254 | 36204 |
| | Group 2 $10^{5.5}$ | #4 | <14 | <14 | <673 | 14368 | 32254 |
| | | #5 | <14 | <14 | 3592 | 18102 | 36204 |
| | | #6 | <14 | <14 | 2263 | 15020 | 36204 |

30

TABLE 2-continued

SN response values

| | | | 0/+2 Vaccination | +5 Challenge | +7 | +11/+12 | +28 |
|---|---|---|---|---|---|---|---|
| | Group 3 $10^6$ | #7 | <14 | <14 | 2727 | 36204 | 36204 |
| | | #8 | <14 | <14 | 4032 | 25600 | 64508 |
| | | #9 | <14 | <14 | 4525 | 16127 | 36204 |
| 5 day OOI | Group 4 $10^5$ | #10 | <14 | 1600 | 25600 | 12800 | 25600 |
| | | #11 | <14 | 3200 | 40637 | 21816 | 40637 |
| | | #12 | <14 | 2016 | 36204 | 25600 | 25600 |
| | Group 5 $10^{5.5}$ | #13 | <14 | 1600 | 20319 | 18102 | 72408 |
| | | #14 | <14 | 3592 | 36204 | 43632 | 51200 |
| | | #15 | <14 | 2727 | 25600 | 18102 | 36204 |
| | Group 6 $10^6$ | #16 | <14 | 4032 | 25600 | 15020 | 18102 |
| | | #17 | <14 | 4032 | 40637 | 18102 | 32254 |
| | | #18 | <14 | 2540 | 15020 | 10159 | 32254 |
| Controls | Group 7 | #19 | <14 | <14 | — | 2263 | * |
| | | #20 | <14 | <14 | — | 3592 | * |
| | | #21 | <14 | <14 | — | 2540 | * |

* Euthanised on animal welfare grounds due to CPV infection

Clinical Observations

There were no clinical signs of parvovirus infection in any of the vaccinates. Vaccination with the CPV 630a vaccine at a titre of $10^{5.0}$ TCID$_{50}$ was therefore able to provide a 3 day onset of immunity against clinical signs. All non-vaccinated controls dogs were euthanised six days post challenge with acute symptoms of haemorrhagic parvovirus infection.

Viral Shedding

All vaccinates shed infectious vaccine virus over a period of one to four days.

Residual shedding in three vaccinated pups on Day +8 could be seen to overlap with the onset of shedding of field virus in the control dogs. This was shown to be vaccine virus by diagnostic PCR. Vaccination with the CPV 630a vaccine at a titre of $10^5$ TCID$_{50}$ was therefore able to prevent challenge virus shedding and induce sterilising immunity.

All control pups began to shed field virus on Day +8; 3 days post challenge. The titres were maximal on day +10 and remained high until the end of the study.

Serological Responses

The serological data shown in Tables 1 and 2 indicates a temporal, dose dependent response to vaccination that correlated with the clinical onset of immunity.

3 Day OOI

On Day +5; the day of challenge, 2/3 dogs in Groups 1 and 2, and 3/3 dogs in Group 3 had begun to seroconvert in a dose dependent manner. By Day +7, two days post challenge, all pups had strongly seroconverted. Rapid seroconversion protected the pups from clinical disease.

5 Day OOI

All of the pups in Groups 4, 5 and 6 seroconverted by Day +5, the day of challenge. The antibody titres were maximal by Day +12 and remained high until the end of the study.

Controls

All of the pups were seronegative for CPV antibodies at the start of the study, seroconverting by Day +11; 6 days post challenge.

Conclusions

The results of this study surprisingly indicate that vaccination with parvovirus 630a at a titre of $10^{5.0}$ $TCID_{50}$ is able to provide a three day onset of immunity against clinical signs and challenge virus shedding in 10 week SPF pups. It is further surprisingly found that the protected dogs had sterilising immunity even when they didn't have a sufficient antibody response on the day of challenge. This was very surprising as historically a titre of 80 HAI units was universally accepted as being the protective level.

Example 2

The objective of the study was to investigate the efficacy of the live attenuated CPV 630a vaccine in 4-week-old pups. A further objective was to demonstrate a three-day onset of immunity for the CPV 630a vaccinated pups when administered at 4 weeks of age.

Study Design

Two litters of SPF Beagle puppies free of antibodies to canine parvovirus were divided into two groups and treated as detailed below.

7 pups were subcutaneously vaccinated with a single dose of a freeze-dried canine distemper virus/canine parvovirus combination test vaccine (parvovirus 630a) resuspended in Nobivac® Solvent (Vaccinates: Group 1). 5 pups remained as unvaccinated controls (Group 2). Three days after vaccination of Group 1, the pups in both groups were simultaneously challenged with a virulent Italian CPV-2c field strain by oral administration.

Blood samples were taken for CPV serological analysis on study days 0 (day of vaccination), +3 (day of challenge), +6 (three days post challenge), +10 (seven days post challenge) and +17 (day of termination). An additional blood sample was also taken from any dog that was euthanised on welfare grounds prior to the end of the study.

In order to monitor for vaccine virus and/or challenge virus shedding, daily rectal swabs were taken from all dogs throughout the study. Differential PCR analysis of the study day +6 rectal swabs was carried out to discriminate between vaccine and field virus shedding.

All pups were observed daily for clinical signs throughout the study. Clinical observations included daily body weights and rectal temperatures.

Vaccine

CPV630a/CDV Combination Vaccine

Titre CPV: $10^{5.1}$ $TCID_{50}$/dose; 1 dose/vial, Lyophilised

Titre CDV: $10^{5.1}$ $TCID_{50}$/dose; 1 dose/vial, Lyophilised

Solvent (diluent): Nobivac® Solvent (Intervet International/MSD Animal Health, Boxmeer)

Test System

SPF Beagle Dogs, 4 weeks of age (both male and female)

Vaccination

Vaccinates: Group 1

All 7 pups were subcutaneously vaccinated with a single 0.5 ml dose of the freeze-dried canine distemper virus/canine parvovirus combination test vaccine resuspended in Nobivac® Solvent.

The Group 2 pups were not vaccinated.

Challenge

The CPV-2c Italian field virus was orally administered at a dose of $10^{5.4}$ $TCID_{50}$.

Results

The serological response of the pup is detailed in the following Tables 3 and 4. The serological response of the pups to canine parvovirus by haemagglutinin inhibition assay (HAI) is given in the Table 3. The serological response of the pups to canine parvovirus by serum neutralisation assay (SN) is given in the Table 4. The results shown are those measured against CPV-2c antigen.

TABLE 3

HAI response values

| | | | | Study Day | | |
|---|---|---|---|---|---|---|
| | | 0 | | | 10 | |
| Group | Dog ID | Vacci-nation | 3 Challenge | 6 | (Day 8/9 for Group 2) | 17 |
| 1 | #1 | $16^a$ | 288 | 40,960 | >40,960 | 36,864 |
| Vaccinates | #2 | $16^a$ | 144 | 40,960 | >40,960 | >40,960 |
| | #3 | $8^a$ | 224 | 26,624 | 18,432 | 13,312 |
| | #4 | <8 | 288 | 40,960 | >40,960 | 26,624 |
| | #5 | <8 | 144 | 40,960 | >40,960 | 18,432 |
| | #6 | $8^a$ | 288 | 40,960 | >40,960 | 18,432 |
| | #7 | <8 | 288 | >36,864 | >40,960 | 26,624 |
| 2 | #8 | <8 | — | <8 | 9216 | — |
| Controls | #9 | <8 | — | <8 | 9216 | — |
| | #10 | <8 | — | <8 | 4608 | — |
| | #11 | $16^a$ | — | <8 | 9216 | — |
| | #12 | $16^a$ | — | <8 | 4608 | — |

Antibody titres of <8 HAI units are considered to be seronegative, unless serum interference was observed — Not tested $^a$Serum interference was seen in the first one or two wells of the HAI plate. This low level of serum interference is not uncommon when using low pre-dilutions of sera from young pups and the dogs were considered to be negative for canine parvovirus antibodies

TABLE 4

SN response values

| | | | Study Day | |
|---|---|---|---|---|
| Group | Dog ID | 3 Challenge | 6 | 10 (Day 8/9 for Group 2) |
| 1 | #1 | ≤14 | 8300 | 43,632 |
| Vaccinates | #2 | ≤16 | 4525 | 37,807 |
| | #3 | ≤14 | 10,973 | 21,816 |
| | #4 | ≤16 | 15,020 | 41,587 |
| | #5 | ≤14 | 15,020 | 32,254 |
| | #6 | ≤14 | 6400 | 30,444 |
| | #7 | ≤14 | 10,908 | 25,600 |

TABLE 4-continued

| | | SN response values | | |
|---|---|---|---|---|
| | | | Study Day | |
| Group | Dog ID | 3 Challenge | 6 | 10 (Day 8/9 for Group 2) |
| 2 | #8 | — | — | 2691 |
| Controls | #9 | — | — | 2727 |
| | #10 | — | — | 2016 |
| | #11 | — | — | 5198 |
| | #12 | — | — | 1270 |

Antibody titres of $\leq 14$ $SN_{50}$ are considered to be seronegative, higher values indicate that a level of virus neutralisation was evident.
Not tested

Conclusions

In this study, the efficacy of a single low titre inoculation of the CPV 630a vaccine in 4-week-old pups was assessed by experimental canine parvovirus challenge three days after vaccination.

Clinical Parameters of Disease Post Challenge

All vaccinates remained in excellent health throughout the challenge phase. In contrast, each control dog succumbed to classical signs of acute canine parvovirus disease and was euthanised on humane grounds five or six days post infection.

Vaccinates

The vaccinated pups did not develop any clinical signs of canine parvovirus disease or associated pyrexia. All the dogs maintained a largely unbroken increase in weight throughout the study and put on weight as would be predicted for pups of that age.

Controls

Each control pup presented with typical clinical signs of canine parvovirus disease. Despite oral rehydration therapy, the condition of the pups rapidly declined, and they were euthanised on humane grounds 5 or 6 days post infection (study days 8 or 9). A transient pyrexia was seen to coincide with the early stage of disease in three out of the five pups.

Virus Shedding Post Challenge

All dogs were negative for canine parvovirus rectal swab isolation prior to the start of the study. As expected, virus was isolated from the rectal swab material of the vaccinates over a one- to five-day period from 2 to 6 days post vaccination.

Virus was isolated from the rectal swab material of the controls over a three- to four-day period from 3 to 6 days post challenge. All controls were shedding high levels of field virus on day 9, the day of euthanasia.

A second wave of shedding was not observed in the vaccinates after challenge, although the end of the vaccine virus shedding phase overlapped with the beginning of challenge virus shedding in the controls. Differential PCR demonstrated that the virus shed by the vaccinates on the overlapping day 6 (3 days post challenge) was vaccine virus and not challenge virus. This indicates that vaccination 3 days before infection raises sterilising immunity and prevents the shedding of field virus.

Serological Response to Vaccination and Challenge

All pups were seronegative for canine parvovirus prior to vaccination.

On study day 3, the day of challenge, the vaccinates had mounted a modest antibody response against canine parvovirus with a group average of 238 HAI units by 2c biotype. The serological response reached maximal levels by study days 6 to 10 and remained high until the end of the study.

The control pups remained seronegative on study day 6; three days after challenge, after which they mounted a rapid serological response that was clearly detectable in the terminal bleeds five or six days post challenge.

SUMMARY

In conclusion, this study demonstrates that administration of a single vaccination with a minimum titre dose of the CPV 630a vaccine from 4 weeks of age protects against typical signs of canine parvovirus disease and field virus shedding when dogs are infected with field virus three days after vaccination.

Example 3

Objective of the study was to investigate the efficacy of CPV strain 630a vaccine in the presence of maternally derived antibody (MDA) in young pups and to compare the efficacy of the CPV strain 630a vaccine with commercial CPV vaccines.

It is well established that puppies born to vaccinated dams passively acquire maternal antibody against canine parvovirus from the colostrum. As the routine vaccination of dogs against canine parvovirus in the field is now commonplace, the hallmark of an efficacious vaccine is linked to its ability to overcome residual maternal antibody and raise an active immune response. This study was performed to investigate the ability of the CPV 630a strain to overcome maternally derived antibody.

To avoid any additional booster effect due to shed and spread of the vaccine virus, each vaccinated pup was housed as a pair with only one other unvaccinated sentinel pup so that seroconversion could be attributed solely to the efficacy of vaccination. This method of housing reflects the biologically isolated accommodation that most pups encounter after being separated from their litter group and moving to a permanent home.

Study Design

Pups of 5-6 weeks of age were split into pair of pups; each group contained one vaccinated pup and one unvaccinated sentinel pup. Each pair of pups was housed in a separate biocontainment room.

The pups were screened prior to vaccination by HAI and the vaccinates were selected to have a range of low, moderate and high maternal antibody titres that are representative of the equivalent levels found in pups of the same age in the field. The unvaccinated sentinels were selected to have an equal or lower level of antibody than their paired vaccinate.

All vaccinated pups received a single vaccination with one dose of the CPV 630a vaccine or the competitor vaccine. Sentinel pups were not vaccinated.

All pups were bled at regular timepoints for canine parvovirus serology in order to determine the serological status pre- and post-vaccination. As there is a strong correlation between antibody titre and protection from disease, the ability of the CPV 630a vaccine strain to overcome MDA and because seroconversion was used as a marker of efficacy. Daily rectal swabs were also taken to monitor for shed and spread.

All pups were observed daily as part of routine daily husbandry.

Vaccines:

CPV/CDV combination vaccine (Intervet International/MSD Animal Health, Boxmeer); 1 dose/vial, Lyophilised Titre CPV strain 630a: $10^{5.8}$ TCID$_{50}$/dose Titre CDV: $10^{6.4}$ TCID50/dose Nobivac Solvent (diluent); Intervet International bv/MSD Animal Health, Boxmeer.

Versican Plus P (Zoetis, CPV-2b strain BIO 12/B); 1.0 ml/dose, lyophilised Titre: $10^{4.3}$ to $10^{6.6}$ TCID$_{50}$ per dose Eurican Primo P (Boehringer Ingelheim, CPV-2 strain 115-780916-Cornell Univ.) Titre: $\geq 10^{5.5}$ TCID$_{50}$ per dose Vanguard Plus 5 (Zoetis); 1.0 ml/dose, lyophilized, resuspended in solvent supplied)

Titre CDV:$\geq 10^{3.0}$ TCID50 per dose

Titre CAV-2:$\geq 10^{3.2}$ TCID50 per dose

Titre CPi:$\geq 10^{6.0}$ TCID50 per dose

CPV-2c:$>10^{7.0}$ TCID$_{50}$ per dose

Test System

SPF Beagle Dogs, 4-6 weeks of age (both male and female)

Treatment

Just prior to vaccination, Versican Plus P was resuspended in 1 ml of the diluent supplied. Eurican Primo P was supplied as a 1 ml ready to use liquid. Vanguard Plus 5 was resuspended in ml of the diluent (Vanguard Plus 5 (solvent) supplied.

TABLE 5

Groups used for vaccination

| Group | No. of Pups | Role | Maternal Antibody Status | Vaccination (1.0 ml SC) |
|---|---|---|---|---|
| 1 | 1 | Vaccinate | Low | Single dose CPV 630a/CDV |
|  | 1 | Sentinel | * | — |
| 2 | 1 | Vaccinate | Moderate | Single dose CPV 630a/CDV |
|  | 1 | Sentinel | * | — |
| 3 | 1 | Vaccinate | High | Single dose CPV 630a/CDV |
|  | 1 | Sentinel | * | — |

TABLE 5-continued

Groups used for vaccination

| Group | No. of Pups | Role | Maternal Antibody Status | Vaccination (1.0 ml SC) |
|---|---|---|---|---|
| 4 | 1 | Vaccinate | High | Single dose CPV 630a/CDV |
|  | 1 | Sentinel | * | — |
| 5 | 1 | Vaccinate | High | Single dose CPV 630a/CDV |
|  | 1 | Sentinel | * | — |
| 6 | 1 | Vaccinate | Moderate # | Single dose Versican plus P |
|  | 1 | Sentinel | * | — |
| 7 | 1 | Vaccinate | High # | Single dose Versican plus P |
|  | 1 | Sentinel | * | — |
| 8 | 1 | Vaccinate | Moderate | Single dose Versican plus P |
|  | 1 | Sentinel | * | — |
| 9 | 1 | Vaccinate | Low | Single dose Versican plus P |
|  | 1 | Sentinel | * | — |
| 10 | 1 | Vaccinate | Moderate # | Single dose Eurican Primo P |
|  | 1 | Sentinel | * | — |
| 11 | 1 | Vaccinate | High # | Single dose Eurican Primo P |
|  | 1 | Sentinel | * | — |
| 12 | 1 | Vaccinate | Moderate | Single dose Eurican Primo P |
|  | 1 | Sentinel | * | — |
| 13 | 1 | Vaccinate | Low | Single dose Eurican Primo P |
|  | 1 | Sentinel | * | — |
| 14 | 1 | Vaccinate | Moderate | Single dose Vanguard Plus 5 |
|  | 1 | Sentinel | * | — |
| 15 | 1 | Vaccinate | Moderate | Single dose Vanguard Plus 5 |
|  | 1 | Sentinel | * | — |
| 16 | 1 | Vaccinate | Moderate | Single dose Vanguard Plus 5 |
|  | 1 | Sentinel | * | — |
| 17 | 1 | Vaccinate | Low | Single dose Vanguard Plus 5 |
|  | 1 | Sentinel | * | — |

SC: Subcutaneous

* MDA level equal or lower than paired vaccinate.

The day 0 serological data showed that the pups with high and moderate MDA levels were in a different order than had been predicted by the pre-screening.

Results

The serological response of the pups by HAI and SN assay is detailed in the following Tables 6 and 7. The results shown are those measured against CPV-2c antigen.

TABLE 6

HAI response values

Vaccine: CPV 630a/CDV

| | | | | Study Day | | | | | | | | | |
|---|---|---|---|---|---|---|---|---|---|---|---|---|---|---|
| G | ID | A | St | 0 | 3 | 5 | 7 | 9 | 11 | 14 | 18 | 21 | 28 | Sh |
| 1 | 1 | 6; 5 | V | 72 | 72 | 26 | 2304§ | 9216§ | 1664§ | 10,752§ | 18,432§ | 14,336§ | 13,312§ | 6, 7 |
|  | 2 | 6; 5 | S | 36 | 36 | 36 | 36 | <16 | 3328§ | 13,312§ | 18,432§ | 14,336§ | 9216§ | 6, 10-12 |
| 2 | 3 | 6; 5 | V | 144 | 72 | 36 | 1152§ | 7168§ | 72§ | 18,432§ | 18,432§ | 14,336§ | 13,312§ | 6, 7 |
|  | 4 | 6; 5 | S | 104 | 52 | 52 | 52 | 36 | 4608§ | 9216§ | >32,768§ | 18,432§ | 13,312§ | 11-14 |
| 3 | 5 | 6; 2 | V | 416 | 416 | 208 | 104 | 832§ | 208§ | 13,312§ | 13,312§ | 14,336§ | 18,432§ | 8-10 |
|  | 6 | 6; 2 | S | 416 | 416 | 288 | 288 | 288 | 8432 | 16* | 13,312§ | 28,672§ | 13,312§ | 11, 15-17 |
| 4 | 7 | 5; 1 | V | 576 | 298 | 288 | 144 | 144 | <16§ | >40,960§ | <40,960§ | >81,920§ | ≥40,960§ | 9-11 |
|  | 8 | 6; 5 | S | 144 | 104 | 72 | 36 | 36 | 13,312 | 112§ | 13,312§ | 9216§ | 6656§ | 13-15 |
| 5 | 9 | 5; 2 | V | 576 | 416 | 288 | 72 | 9216§ | 144§ | 20,480§ | <32,768§ | 18,432§ | 13,312§ | 6-9 |
|  | 10 | 5; 1 | S | 416 | 416 | 288 | 144 | 208 | 1664 | 144 | 104 | 144 | 72 | None |

TABLE 6-continued

HAI response values

Vaccine: Versican Plus P

| | | | | | | | | Study Day | | | | | |
|---|---|---|---|---|---|---|---|---|---|---|---|---|---|
| G | ID | Age | St | 0 | 3 | 5 | 7 | 9 | 11 | 14 | 18 | 21 | 28 | Sh |
| 6 | 11 | 5; 0 | V | 288 | 288 | 288 | 224 | 72 | 576§ | 9216§ | 13312§ | 14336§ | 9216§ | None |
| | 12 | 5; 0 | S | 288 | 288 | 288 | 144 | 208 | 144 | 144 | 72 | 144 | 52 | None |
| 7 | 13 | 4; 3 | V | 576 | 288 | 144 | 144 | 144 | 144 | 144 | 104 | 144 | 52 | None |
| | 14 | 5; 0 | S | 288 | 144 | 144 | 144 | 144 | 144 | 104 | 72 | 112 | 52 | None |
| 8 | 15 | 4; 3 | V | 448 | 208 | 144 | 144 | 144 | 144 | 72 | 72 | 72 | 36 | 9, 10 |
| | 16 | 5; 1 | S | 144 | 72 | 72 | 72 | 72 | 52 | 52 | 36 | 36 | 18 | None |
| 9 | 17 | 5; 0 | V | 144 | 72 | 72 | 72 | 288§ | 7168§ | 26624§ | 26624§ | 36864§ | 18432§ | 7-10 |
| | 18 | 5; 0 | S | 144 | 72 | 52 | 52 | 72 | 52 | 52 | 36 | 36 | 18 | None |

Vaccine: Eurican Primo P

| | | | | | | | | Study Day | | | | | |
|---|---|---|---|---|---|---|---|---|---|---|---|---|---|
| G | ID | A | St | 0 | 3 | 5 | 7 | 9 | 11 | 14 | 18 | 21 | 28 | Sh |
| 10 | 19 | 5; 0 | V | 416 | 288 | 288 | 104 | 224 | 144 | 144 | 104 | 104 | 72 | None |
| | 20 | 5; 1 | S | 288 | 144 | 144 | 104 | 144 | 104 | 72 | 72 | 72 | 36 | None |
| 11 | 21 | 4; 3 | V | 576 | 288 | 192 | 168 | 224 | 144 | 144 | 104 | 104 | 72 | None |
| | 22 | 5; 1 | S | 288 | 144 | 112 | 104 | 144 | 72 | 72 | 52 | 52 | 36 | None |
| 12 | 23 | 5; 0 | V | 288 | 208 | 144 | 144 | 144 | 144 | 832§ | 2304§ | 3328§ | 1152§ | None |
| | 24 | 5; 0 | S | 144 | 72 | 72 | 72 | 52 | 52 | 36 | 36 | 36 | 18 | None |
| 13 | 25 | 5; 0 | V | 144 | 72 | 72 | 72 | 72 | 1152§ | 9216§ | 9216§ | 9216§ | 4608§ | 10, 11 |
| | 26 | 5; 1 | S | 104 | 72 | 52 | 72 | 36 | 36 | 36 | 36 | 36 | 18 | None |

Vaccine: Vanguard Plus 5

| | | | | | | | | Study Day | | | | | |
|---|---|---|---|---|---|---|---|---|---|---|---|---|---|
| G | ID | A | St | 0 | 3 | 5 | 7 | 9 | 11 | 14 | 18 | 21 | 28 | Sh |
| 14 | 27 | 6; 2 | V | 208 | 144 | 144 | 144 | 104 | 144 | 104 | 72 | 36 | 36 | None |
| | 28 | 5; 6 | S | 144 | 104 | 104 | 72 | 52 | 72 | 52 | 36 | 36 | 18 | None |
| 15 | 29 | 6; 2 | V | 208 | 144 | 144 | 104 | 144 | 288 | 144 | 72 | 52 | 36 | None |
| | 30 | 5; 6 | S | 104 | 72 | 72 | 52 | 36 | 36 | 36 | 36 | 26 | 16 | None |
| 16 | 31 | 6; 2 | V | 208 | 104 | 104 | 288§ | 2304§ | 3328§ | 2304§ | 1152§ | 1152§ | 832§ | None |
| | 32 | 5; 6 | S | 104 | 72 | 72 | 72 | 36 | 36 | 36 | 36 | 26 | 18 | None |
| 17 | 33 | 6; 2 | V | 72 | 52 | 72 | 288§ | 1152§ | 4608§ | 3328§ | 3328§ | 2304§ | 3328§ | None |
| | 34 | 6; 2 | S | 72 | 52 | 36 | 26 | 28 | 36 | 18 | 18 | 18 | <16 | None |

§indicates active seroconversion

Values of <16 are considered to be seronegative

G = group#;

ID = pup ID #;

A = age on day 0 (5; 0 means 5 weeks 0 days);

St = status (vaccinated (V) or sentinel (S);

Sh = Days of virus shedding

TABLE 7

SN response values

Vaccine: CPV 630

| | | | | | | | | | Study Day | | | | | |
|---|---|---|---|---|---|---|---|---|---|---|---|---|---|---|
| G | ID | A | St | 0 | 3 | 5 | 7 | 9 | 11 | 14 | 18 | 21 | 28 | Sh |
| 1 | 1 | 6; 5 | V | 160 | 127 | ≤16 | 1131§ | 7184§ | 32,254§ | 25,600§ | 40,637§ | 51,200§ | 72,408§ | 6, 7 |
| | 2 | 6; 5 | S | 113 | 80 | 63 | 57 | ≤14 | 1600§ | 18,102§ | 32,254§ | 21,816§ | 32,254§ | 6, 10-12 |
| 2 | 3 | 6; 5 | V | 188 | 202 | ≤14 | 283§ | 8063§ | 25,600§ | 51,200§ | 40,637§ | 25,600§ | 72,408§ | 6, 7 |
| | 4 | 6; 5 | S | 160 | 113 | 101 | 94 | 80 | ≤20§ | 6400§ | 30,041§ | 25,600§ | 25,600§ | 11-14 |
| 3 | 5 | 6; 2 | V | 1131 | 905 | 806 | 202 | 718§ | 16,127§ | 9051§ | 15,020§ | 36,204§ | 64,508§ | 8-10 |
| | 6 | 6; 2 | S | 1131 | 1016 | 905 | 905 | 806 | 453 | 50 | 10,159§ | 10,908§ | 16,127§ | 11, 15-17 |
| 4 | 7 | 5; 1 | V | 1280 | 1280 | 1016 | 320 | 113 | 64,508§ | 40,637§ | <144,815§ | ≥129,016§ | ≥129,016§ | 9-11 |
| | 8 | 6; 2 | S | 226 | 101 | 113 | 101 | 80 | ≤14 | 28§ | 10,908§ | 16127§ | 18,102§ | 13-15 |
| 5 | 9 | 5; 2 | V | 1008 | 1091 | 453 | ≤14 | 8063§ | 18,102§ | 36,204§ | 43,632§ | 20,319§ | 64,508§ | 6-9 |
| | 10 | 5; 1 | S | 1131 | 806 | 905 | 806 | 751 | 640 | 508 | 320 | 403 | 254 | None |

TABLE 7-continued

SN response values

Vaccine: Versican Plus P

| | | | | Study Day | | | | | | | | | | |
| G | ID | A | St | 0 | 3 | 5 | 7 | 9 | 11 | 14 | 18 | 21 | 28 | Sh |
|---|----|-----|---|-----|-----|-----|-----|-----|------|---------|---------|---------|---------|------|
| 6 | 11 | 5; 0 | V | 806 | 640 | 806 | 403 | 127 | 403§ | 36204§ | 25600§ | 36204§ | 36204§ | None |
| | 12 | 5; 0 | S | 751 | 508 | 640 | 403 | 403 | 320 | 403 | 403 | 226 | 127 | None |
| 7 | 13 | 4; 3 | V | 806 | — | — | — | — | — | — | — | — | — | None |
| | 14 | 5; 0 | S | 403 | — | — | — | — | — | — | — | — | — | None |
| 8 | 15 | 4; 3 | V | 508 | — | — | — | — | — | — | — | — | — | 9, 10 |
| | 16 | 5; 1 | S | 160 | — | — | — | — | — | — | — | — | — | None |
| 9 | 17 | 5; 0 | V | 188 | 160 | 160 | 113 | 948 | 5454§ | 102400§ | 81275§ | 87263§ | 72408§ | 7-10 |
| | 18 | 5; 1 | S | 160 | 113 | 94 | 63 | 80 | 57 | 80 | 40 | 57 | <14 | None |

Vaccine: Eurican Primo P

| | | | | Study Day | | | | | | | | | | |
| G | ID | A | St | 0 | 3 | 5 | 7 | 9 | 11 | 14 | 18 | 21 | 28 | Sh |
|----|----|-----|---|-----|-----|-----|-----|-----|------|--------|--------|--------|--------|--------|
| 10 | 19 | 5; 0 | V | 806 | — | — | — | — | — | — | — | — | — | None |
| | 20 | 5; 1 | S | 403 | — | — | — | — | — | — | — | — | — | None |
| 11 | 21 | 4; 3 | V | 640 | — | — | — | — | — | — | — | — | — | None |
| | 22 | 5; 1 | S | 453 | — | — | — | — | — | — | — | — | — | None |
| 12 | 23 | 5; 0 | V | 453 | 508 | 453 | 320 | 226 | 202 | 1131§ | 4525§ | 4032§ | 2263§ | None |
| | 24 | 5; 0 | S | 113 | 127 | 113 | 101 | 101 | 101 | 80 | 63 | 57 | 32 | None |
| 13 | 25 | 5; 0 | V | 226 | 160 | 127 | 160 | 113 | 252§ | 16127§ | 16127§ | 12800§ | 10159§ | 10, 11 |
| | 26 | 5; 1 | S | 101 | 113 | 101 | 101 | 80 | 57 | 50 | 34 | 34 | 25 | None |

Vaccine: Vanguard Plus 5

| | | | | Study Day | | | | | | | | | | |
| G | ID | A | St | 0 | 3 | 5 | 7 | 9 | 11 | 14 | 18 | 21 | 28 | Sh |
|----|----|-----|---|-----|-----|-----|------|------|-------|-------|-------|-------|-------|------|
| 14 | 27 | 6; 2 | V | 403 | — | — | — | — | — | — | — | — | — | None |
| | 28 | 5; 6 | S | 320 | — | — | — | — | — | — | — | — | — | None |
| 15 | 29 | 6; 2 | V | 403 | — | — | — | — | — | — | — | — | — | None |
| | 30 | 5; 6 | S | 160 | — | — | — | — | — | — | — | — | — | None |
| 16 | 31 | 6; 2 | V | 226 | 180 | 202 | 113§ | 504§ | 1008§ | 635§ | 449§ | 341§ | 1008§ | None |
| | 32 | 5; 6 | S | 127 | 172 | 127 | 80 | 80 | 80 | 47 | 57 | 32 | ≤20 | None |
| 17 | 33 | 6; 2 | V | 113 | 80 | 80 | 202§ | 400§ | 1363§ | 2016§ | 1878§ | 5080§ | 5080§ | None |
| | 34 | 6; 2 | S | 101 | 63 | 57 | 50 | 32 | 50 | 28 | ≤20 | ≤20 | ≤14 | None |

— not tested
§indicates active seroconversion
Values of <14 are considered to be seronegative
G = group#;
ID = pup ID #;
A = age on day 0 (5; 0 means 5 weeks 0 days);
St = status (vaccinated (V) or sentinel (S));
Sh = Days of virus shedding

Conclusions

CPV 630a Vaccine:

Protective immunity to canine parvovirus can be measured by the neutralising antibody response mounted in response to vaccination. Given that morbidity and mortality are highest in young pups, the ability to mount a protective immune response in the presence of maternally derived antibody is particularly important for an efficacious vaccine.

The serological data in Tables 6 and 7 indicates that the CPV 630a vaccine of the present invention is able to induce protective immunity to canine parvovirus in 5-6-week-old pups with low to high levels of maternally derived antibody. As each vaccinated pup was housed as a pair with only one other unvaccinated sentinel pup, seroconversion can be attributed solely to the efficacy of vaccination. This method of housing reflects the biologically isolated accommodation that most pups encounter after being separated from their litter group and moving to a permanent home. In the majority of cases, newly homed pups enter into a single dog household or a multi-dog household where any existing dog(s) have completed their primary vaccination some time previously.

Vaccinates:

All vaccinated pups seroconverted following vaccination. The serological HAI data in Table 6 indicates that the temporal response of each dog was dependent on the level of maternal antibody present on the day of vaccination. Two pups with maternal antibody titres of 72 and 144 HAI units mounted a serological response by day 7. Subsequently, a further two pups with antibody titres of 416 and 576 HAI units seroconverted by day 9. The fifth pup with an antibody titre of 576 HAI units had strongly seroconverted by day 11. After seroconversion, all antibody titres remained high throughout the remainder of the study. There were no observable differences in the antibody titres obtained against each of the different CPV 2a, 2b or 2c biotypes.

The serum neutralisation (Table 7) results broadly mirrored the HAI results, with an identical pattern of MDA decline and seroconversion.

Vaccine virus was shed from each vaccinated pup over a 2-4-day period, the onset of shedding occurring just prior to seroconversion (Tables 6 and 7).

Sentinels:

Individually housing an unvaccinated, age matched, sentinel pup with each vaccinate highlighted the shed and spread of vaccine virus. As each sentinel was selected to have an equal, or slightly lower, level of maternal antibody than its paired vaccinate, the kinetics of shed and spread represent a worst-case scenario.

Four of the sentinel pups seroconverted following the shedding of virus in the faeces of the paired vaccinate. Given that dogs have a naturally inquisitive disposition, shed vaccine virus was picked up from faecal material on the floor of the room and the dog became vaccinated via the oronasal route.

In two of the sentinel pups, a transient, low level of vaccine virus was isolated on one day that coincided with the period of shedding in the paired vaccinate. This is believed to be the stochastic transfer of infected faecal matter through the dog and does not represent active shedding of replicating virus from the gut. Four days after ingestion of this material, active replication and shedding could be observed.

The sentinel pup in Group 5 did not seroconvert during the course of the study, despite a similar shedding profile in its paired vaccinate. As the pup had a high level of maternal antibody, it is likely that the amount of vaccine virus that the pup came into contact with was not sufficient to overcome the maternal antibody present. This reflects the variable nature of shed and spread kinetics between animals and is likely to be reflective of a field situation.

Commercial Vaccines:

Haemagglutination Inhibition (Table 6):

The commercial vaccines, Versican Plus P, Eurican Primo P and Vanguard Plus 5, were able to induce active seroconversion to canine parvovirus in pups with low to moderate MDA levels. Contrary to the inventive CPV 630a vaccine, the commercial vaccines could not break through MDA levels of 416/448 to 576 HAI units. Vanguard Plus 5 was not able to consistently break through the moderate MDA level of 208 HAI. For the commercial vaccines, two out of four vaccinated puppies seroconverted following vaccination and none of the co-housed sentinels seroconverted.

The data in this study indicates that the (temporal) response of each dog was dependent on the level of MDA present on the day of vaccination. For two pups with MDA titres of 144 HAI units seroconversion was detected on day 9 and 11 (Versican Plus P and Eurican Primo P respectively).

Subsequently, two pups with antibody titres of 288 HAI units, mounted a serological response which was detected on day 11 and 14 (Versican Plus P and Eurican Primo P respectively). Vanguard Plus 5 vaccinated pups seroconverted by day 7 and active seroconversion was evident throughout the remainder of the study, although the titres were lower than would be predicted.

After seroconversion, all antibody titres remained stable throughout the remainder of the study.

However, for commercial vaccines, the pups with lower MDA and earlier seroconversion mounted higher antibody titres than the pups with higher MDA that seroconverted later. In addition, pups vaccinated with Versican Plus P mounted higher antibody titres than the pups vaccinated with Eurican Primo P. On day 21, the Group 6 (288) and Group 9 (144) Versican Plus P pups raised peak antibody titres of 14,336 and 36,864 HAI units respectively, whilst the Group 12 (288) and Group 13 (144) Eurican Primo P pups raised peak antibody titres of 3328 and 9216 HAI units respectively. The peak antibody titre measured in the Group 12 (288) pup was notably lower than that of the other pups, levelling out at 1152 HAI units/2263 SN units by the end of the study.

Serum Neutralisation (Table 7):

The serum neutralisation results broadly mirrored the HAI results, with an identical pattern of MDA decline and seroconversion.

Virus Isolation from Rectal Swabs:

As demonstrated with the inventive CPV strain 630a, vaccine virus was shed from each vaccinated pup over a 2-4-day period, the onset of shedding occurring just prior to seroconversion. Subsequently, four of the five sentinel pups seroconverted following the shedding of virus in the faeces of the paired vaccinate.

Versican Plus P and Eurican Primo P vaccine viruses seem to shed to a lesser extent than CPV strain 630a and shed virus did not spread to the sentinels. Vaccine virus was isolated from the rectal swabs of three out of the four seroconverted, vaccinated pups; two Versican Plus P pups and the Eurican Primo P pup with the lowest starting MDA titre of 144 HAI units. Shedding was detected over a 2-4-day period, the onset of shedding occurring just prior to seroconversion. Despite this, the amount of virus shed was not enough to overcome the MDA present in the sentinel pup and induce seroconversion or viral shedding. Virus could not be isolated from the second seroconverted, vaccinated Eurican Primo P pup with the higher starting MDA titre of 288 HAI units. This pup showed a late onset of seroconversion (day 14) and only developed a peak HAI titre of 3328 HAI units/4032 SN units, perhaps indicating limited viral replication in vivo. It is therefore conceivable that an MDA titre of 288 HAI units represents the threshold of efficacy for this vaccine strain. The Vanguard Plus 5 vaccine virus seems not to shed, or to a lesser extent than CPV strain 630a, and shed virus did not spread to the sentinels. No vaccine virus was isolated from the rectal swabs of any of the vaccinated pups, including the seroconverted pups.

SUMMARY

The administration of a single dose of the inventive CPV 630a vaccine with a titre that is representative of batches found in routine production is able to breakthrough low to high levels of maternal antibody in 5-6-week-old pups. Individually housing each vaccinated dog with an unvaccinated sentinel highlights the dynamics of shed and spread following vaccination and underlines the potential problems of studying the serological response to vaccination in group housed animals.

Contrary to the results observed for the inventive CPV 630a vaccine, administration of a single dose of a batch of commercial vaccine Versican Plus P (Zoetis), Eurican Primo P (Boehringer Ingelheim (B.I.) or Vanguard Plus 5 is not able to break through higher MDA levels. In addition, vaccine virus was not shed and spread to the unvaccinated co-housed sentinel pups.

Example 4

Objective

This study was performed to investigate the ability of a vaccine including the CPV 630a strain to overcome maternally derived antibody to canine parvovirus from 4 weeks of age. It is well established that puppies born to vaccinated dams passively acquire maternal antibody against canine parvovirus from the colostrum. As the routine vaccination of dogs against canine parvovirus in the field is now commonplace, the hallmark of an efficacious vaccine is linked to its ability to overcome residual maternal antibody and raise an active immune response.

Study Design

Sixteen pups of 4 weeks of age were split into two groups; one group of eleven vaccinates (Group 1) and a second group of five controls (Group 2).

All pups were born to conventionally vaccinated mothers and therefore had varying levels of maternal antibody against canine parvovirus that were representative of a field situation. All pups were pre-screened for serology and the relative levels of maternal antibody were equally spread across the two groups.

All pups in Group 1 received a single vaccination with one dose of the CPV 630a vaccine at 4 weeks of age. The pups in Group 2 were not vaccinated. The two groups were housed in separate biocontainment rooms.

All pups were bled twice a week for canine parvovirus serology in order to determine the serological status pre- and post-vaccination (Group 1) or the natural decline in maternally derived antibody over time (Group 2). As there is a strong correlation between antibody titre and protection from disease, the ability of the CPV 630a vaccine strain to overcome MDA and cause seroconversion within this timeframe was used as a marker of efficacy.

All pups were observed daily as part of routine daily husbandry. At the end of the study, all pups were euthanised.

Vaccines:

CPV/CDV combination vaccine (Intervet International/ MSD Animal Health, Boxmeer); 1 dose/vial, Lyophilised Titre CPV strain 630a: $10^{5.1}$ $TCID_{50}$/dose Titre CDV: $10^{5.1}$ $TCID_{50}$/dose Nobivac Solvent (diluent); Intervet International bv/MSD Animal Health, Boxmeer.

Test System

SPF Beagle dogs, 4 weeks of age, (male and female)

Results:

The serological response of the pups is detailed in the following Tables 8 and 9. Haemagglutiation Inhibition (HAI) response values are shown in Table 8 below. Serum Neutralisation (SN) values are shown in Table 9 below. The results shown are those measured against CPV-2c antigen

TABLE 8

HAI response values

| | | | | | | | Study Day | | | | | |
|---|---|---|---|---|---|---|---|---|---|---|---|---|
| G | ID | A | 0 | 4 | 7 | 11 | 14 | 21 | 28 | 34 | 41 | 48 | 59 |
| 1 | 1 | 4; 1 | 832 | 576 | 576 | 416 | 416 | 288 | 1152§ | >40,960§ | 18,432§ | 13,312§ | >21,504§ |
| V | 2 | 4; 3 | 288 | 288 | 288 | 288 | 104 | 18,432§ | 13,312§ | 18,432§ | 13,312§ | 13,312§ | 18,432§ |
| | 3 | 4; 4 | 288 | 288 | 288 | 288 | <16§ | 18,432§ | 6656§ | 9216§ | 6656§ | 9216§ | 18,432§ |
| | 4 | 4; 4 | 416 | 288 | 208 | 9216§ | 9216§ | 18,432§ | 6656§ | 18,432§ | 13,312§ | 18,432§ | >28,672§ |
| | 5 | 4; 4 | 416 | 416 | <16§ | 6656§ | † | † | † | † | † | † | † |
| | 6 | 4; 3 | 416 | 208 | 288 | 416 | 9216§ | 18,432§ | 13,312§ | 18,432§ | 13,312§ | 13,312§ | 18,432 |
| | 7 | 4; 4 | 416 | 288 | <16§ | 6656§ | 6656§ | 9216§ | 6656§ | 13,312§ | 9216§ | 18,432§ | 18,432§ |
| | 8 | 4; 1 | 832 | 576 | 576 | 576 | 576 | 288 | 144 | 144 | 52 | 52 | >26,624§ |
| | 9 | 4; 1 | 576 | 576 | 576 | 832 | 9216§ | 9216§ | 6656§ | 9216§ | 6656§ | 9216§ | 13,312§ |
| | 10 | 4; 1 | 832 | 576 | 896 | 576 | 576 | 288 | 144 | 144 | <16§ | 28,672§ | 18,432§ |
| | 11 | 4; 1 | 1664 | 576 | 1152 | 832 | 416 | 288 | 144 | 144 | 72 | 36 | 18,432§ |
| 2 | 12 | 4; 3 | 288 | 144 | 288 | 288 | 104 | 72 | 72 | 56 | 18 | 52 | <8 |
| C | 13 | 4; 4 | 416 | 288 | 288 | 288 | 208 | 144 | 72 | 112 | 36 | 36 | 18 |
| | 14 | 4; 1 | 832 | 576 | 832 | 832 | 416 | 288 | 144 | 144 | 52 | 36 | 28 |
| | 15 | 4; 1 | 832 | 576 | 832 | 832 | 416 | 288 | 144 | 144 | 52 | 36 | 28 |
| | 16 | 4; 1 | 832 | 416 | 832 | 576 | 288 | 288 | 112 | 144 | 36 | 36 | <8 |

† Pup was euthanized for reasons unrelated to vaccination
§ Active seroconversion
NS Not enough serum sample
G = group# (V = vaccinates; C = controls);
ID = pup ID #;
A = age on day 0 (5; 0 means 5 weeks 0 days);

50

TABLE 9

SN response values

| | | | | | | | Study Day | | | | | |
|---|---|---|---|---|---|---|---|---|---|---|---|---|
| G | ID | A | 0 | 4 | 7 | 11 | 14 | 21 | 28 | 34 | 41 | 48 | 59 |
| 1 | 1 | 4; 1 | 2016 | 1131 | 1008 | 905 | 545 | 453 | 317§ | 20,319§ | 12,800§ | 25,600§ | 45,614§ |
| V | 2 | 4; 3 | 806 | 905 | 640 | 320 | NS | 18,102§ | 64,508§ | 51,200§ | 40,637§ | 40,637§ | 40,637§ |
| | 3 | 4; 4 | 905 | 806 | 640 | 508 | <14§ | 20,319§ | 12,800§ | 20,319§ | 51,200§ | 36,204§ | 32,254§ |
| | 4 | 4; 4 | 905 | 806 | 320 | 475§5 | 6400§ | 25,600§ | 36,204§ | 43,632§ | 87,263§ | 87,263§ | 64,508§ |
| | 5 | 4; 4 | 1016 | 806 | ≤14§ | 2263§ | † | † | † | † | † | † | † |
| | 6 | 4; 4 | 905 | 905 | 806 | 254 | 18,102§ | 51,200§ | ≥144,815§ | 64,508§ | 72,408§ | 51,200§ | 51,200§ |
| | 7 | 4; 4 | 1280 | 905 | <14§ | 2263§ | 8063§ | 25,600§ | 40,637§ | 51,200§ | 40,637§ | 64,508§ | 64,508§ |
| | 8 | 4; 4 | 4032 | 1363 | 1600 | 1280 | 640 | 508 | 403 | 320 | 113 | 40 | 16,127§ |
| | 9 | 4; 4 | 2263 | 1600 | 1270 | 403 | 12,800§ | 32,254§ | 32,254§ | 51,200§ | 32,254§ | 40,637§ | 36,204§ |

TABLE 9-continued

| G | ID | A | \multicolumn{11}{c}{SN response values} | | | | | | | | | | |
|---|---|---|---|---|---|---|---|---|---|---|---|---|---|
| | | | \multicolumn{11}{c}{Study Day} | | | | | | | | | | |
| | | | 0 | 4 | 7 | 11 | 14 | 21 | 28 | 34 | 41 | 48 | 59 |
| | 10 | 4; 1 | 1878 | 2540 | 2263 | 1131 | 635 | 905 | 453 | 226 | ≤14§ | 25,600§ | 32,254§ |
| | 11 | 4; 1 | 4525 | 3200 | 2016 | 1600 | 1270 | 806 | 453 | 202 | 226 | 57 | 15,020§ |
| 2- | 12 | 4; 3 | 640 | 751 | 403 | 226 | 376 | 202 | 80 | 50 | 28 | ≤14 | ≤14 |
| C | 13 | 4; 4 | 905 | 806 | 640 | 453 | 320 | 254 | 160 | 101 | 57 | 50 | 25 |
| | 14 | 4; 1 | 4032 | 2540 | 1600 | 1280 | 1613 | 453 | 226 | 127 | 80 | 50 | 50 |
| | 15 | 4; 1 | 4032 | 2016 | 2263 | 1131 | 1270 | 806 | 508 | 127 | 160 | 80 | 57 |
| | 16 | 4; 1 | 2727 | 1600 | 1008 | 1280 | 1613 | 403 | 226 | 160 | 80 | 50 | 25 |

† Pup was euthanized for reasons unrelated to vaccination
§Active seroconversion
NS: Not enough serum sample
G = group# (V = vaccinates; C = controls);
ID = pup ID #;
A = age on day 0 (5; 0 means 5 weeks 0 days);

Conclusions

The serological data indicates that the vaccine of the present invention including the parvovirus strain 630a is able to induce protective immunity to canine parvovirus in 4-week-old pups with moderate to high levels of maternally derived antibody.

Vaccinates:

Each pup in Group 1 was vaccinated with a single dose of the test vaccine, formulated to minimum potency. On the day of vaccination, the range of maternal antibody levels measured in the vaccinates was between 288 and 1664 HAI units and 806 and 4525 $SN_{50}$ units (against CPV-2c). All vaccinated pups seroconverted prior to the decay of maternal derived antibody in the controls. After seroconversion, all antibody titres remained high throughout the remainder of the study.

Controls:

The control pups were not vaccinated. On the day of vaccination, the maternally derived antibody levels present in the control pups were within a similar range as those present in the vaccinated pups; 288 and 832 HAI units and 640 and 4032 $SN_{50}$ units (against CPV-2c). The maternal antibody levels within each pup declined predictably over time, with a half-life of approximately 11 to 14 days.

SUMMARY

In conclusion, the administration of a single dose of the inventive CPV 630a vaccine was able to breakthrough all of the levels of maternally derived antibody present in 4-week-old pups. The data demonstrate that maternally derived antibody does not interfere with the vaccination of pups from 4 weeks of age.

The invention claimed is:

1. A method for protecting an animal against parvovirus infection, comprising administering to the animal a pharmaceutical composition comprising the live attenuated parvovirus comprising a capsid gene coding for an amino acid other than Isoleucine at amino acid position 219 of the VP2 capsid protein and/or an amino acid other than Glutamine at amino acid position 386 of the VP2 capsid protein, wherein the pharmaceutical composition is administered to the animal as a single dose and is administered during weeks 2-20 of age of the animal, and wherein the animal is protected against parvovirus infection even when the animal has maternal derived antibodies (MDA) against parvovirus at the time of administration.

2. The method of claim 1, wherein the pharmaceutical composition is administered to the animal as a single dose during weeks 2-12 of age of the animal.

3. The method of claim 1, wherein the onset of immunity is achieved at day four or earlier following administration of the pharmaceutical composition, where the animal has presence of maternally derived antibodies (MDA).

4. The method of claim 1, wherein administration is performed independent from the animal's pre-vaccination hemagglutinin inhibition (HAI) titre of maternally derived antibody (MDA) measured at time of administration of the pharmaceutical composition.

5. The method of claim 1, wherein the animal's pre-vaccination HAI titre of MDA measured at time of administration of the pharmaceutical composition is higher than 288.

6. The method of claim 1, wherein the live attenuated parvovirus is a canine parvovirus, and wherein the animal is dog.

7. The method of claim 6, wherein the dog is housed as a single vaccinated dog during a period of at least one week after administration of the pharmaceutical composition.

8. The method of claim 1, wherein said virus comprises a capsid gene of CPV2 biotype 2a, 2b or 2c coding for an amino acid other than Isoleucine at amino acid position 219 of the VP2 capsid protein and/or an amino acid other than Glutamine at amino acid position 386 of the VP2 capsid protein, wherein the non-capsid region carries an attenuating mutation.

9. The method of claim 8, wherein said virus comprises a capsid gene coding for an amino acid other than Isoleucine at amino acid position 219 of the VP2 capsid protein and an amino acid other than Glutamine at amino acid position 386 of the VP2 capsid protein.

10. The method of claim 8, wherein said virus comprises a capsid gene coding for a Valine at amino acid position 219 of the VP2 capsid protein and/or a Lysine at amino acid position 386 of the VP2 capsid protein.

11. The method of claim 8, wherein said virus comprises a capsid gene of CPV2 biotype 2c.

12. The method of claim 1 wherein the pharmaceutical composition further comprises a pharmaceutically acceptable carrier.

13. The method of claim 12, wherein the pharmaceutical composition further comprises an antigen of a virus or micro-organism pathogenic to animals or genetic information encoding an immunogenic protein of said virus or micro-organism, the virus or microorganism selected from the group consisting of *Ehrlichia canis, Babesia gibsoni, vogeli, rossi, Leishmania donovani*-complex, Canine adenovirus, Canine coronavirus, Canine distemper virus, *Leptospira interrogans* serovar canicola, *Leptospira interrogans* serovar icterohaemorrhagiae, *Leptospira interrogans* serovar pomona, *Leptospira interrogans* serovar grippotyphosa, *Leptospira interrogans* serovar bratislava, Canine hepatitis-virus, Canine parainfluenzavirus, rabies virus, *Hepatozoon canis, Borrelia burgdorferi, Bordetella bronchiseptica*, feline Herpesvirus, feline calicivirus, feline panleucopenia, *Chlamydophila felis*, and corona virus.

14. A method of manufacture of the pharmaceutical composition of claim 12, the method comprising:

(1) transfection of cells with genetic material from the live attenuated parvovirus and culturing of the cells under conditions that allow the production of a live attenuated parvovirus, wherein the method comprises at most two passages of the virus following transfection, (2) isolation of the live attenuated parvovirus from the cell culture, and (3) mixing the live attenuated parvovirus with a pharmaceutically acceptable carrier, wherein the live attenuated parovirus is a capsid gene coding for an amino acid other than Isoleucine at amino acid position 219 of the VP2 capsid protein and/or an amino acid other than Glutamine at amino acid position 386 of the VP2 capsid protein.

15. A pharmaceutical composition obtainable by the method according to claim 14.

16. The method of claim 1, wherein the animal is not a serum pathogen free (SPF) animal.

17. The method of claim 1, wherein the animal is protected by at least 5 days following administration of the vaccine even when the animal has MDA against parvovirus.

18. A method to induce a protective immune response in an animal against parvovirus even when the animal has maternally derived antibody (MDA), comprising administering to the animal a single dose at age 2-20 weeks, a pharmaceutical composition comprising a live attenuated parvovirus comprising a capsid gene coding for an amino acid other than Isoleucine at amino acid position 219 of the VP2 capsid protein and/or an amino acid other than Glutamine at amino acid position 386 of the VP2 capsid protein.

* * * * *

SEQUENCE LISTING

```
<160> NUMBER OF SEQ ID NOS: 12

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 acgtacgta                                                          9

<210> SEQ ID NO 2
<211> LENGTH: 9
<212> TYPE: DNA
<213> ORGANISM: Canine parvovirus

<400> SEQUENCE: 2 taactcctc                                                          9

<210> SEQ ID NO 3
<211> LENGTH: 17
<212> TYPE: PRT
<213> ORGANISM: Canine parvovirus

<400> SEQUENCE: 3
```

-continued

```
Tyr Phe Gln Trp Asp Arg Thr Leu Ile Pro Ser His Thr Gly Thr Ser
1               5                   10                  15

Gly

<210> SEQ ID NO 4
<211> LENGTH: 17
<212> TYPE: PRT
<213> ORGANISM: Canine parvovirus

<400> SEQUENCE: 4

Tyr Ala Phe Gly Arg Gln His Gly Gln Lys Thr Thr Thr Thr Gly Glu
1               5                   10                  15

Thr

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Phe Gln Trp Asp Arg Thr Leu Val Pro Ser His Thr Gly Thr Ser
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ala Phe Gly Arg Gln His Gly Lys Lys Thr Thr Thr Thr Gly Glu
1               5                   10                  15

Thr

<210> SEQ ID NO 7
<211> LENGTH: 2007
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgtctggca accagtatac tgaggaagtt atggagggag taaattggtt aaagaaacat        60
gcagaaaatg aagcattttc gtttgttttt aaatgtgaca acgtccaact aaatggaaag       120
gatgttcgct ggaacaacta taccaaacca attcaaaatg aagagctaac atctttaatt       180
agaggagcac aaacagcaat ggatcaaacc gaagaagaag aaatggactg ggaatcggaa       240
gttgatagtc tcgccaaaaa gcaagtacaa acttttgatg cattaattaa aaaatgtctt       300
tttgaagtct ttgtttctaa aaatatagaa ccaaatgaat gtgtttggtt tattcaacat       360
gaatggggaa aagatcaagg ctggcattgt catgttttac ttcatagtaa gaacttacaa       420
caagcaactg gtaaatggct acgcagacaa atgaatatgt attggagtag atggttggtg       480
actctttgtt cggtaaactt aacaccaact gaaaagatta agctcagaga aattgcagaa       540
```

-continued

```
gatagtgaat gggtgactat attaacatac agacataagc aaacaaaaaa agactatgtt    600
aaaatggttc attttggaaa tatgatagca tattactttt taacaaagaa aaaaattgtc    660
cacatgacaa aagaaagtgg ctatttttta agtactgatt ctggttggaa atttaacttt    720
atgaagtatc aagacagaca aattgtcagc acactttaca ctgaacaaat gaaaccagaa    780
accgttgaaa ccacagtgac gacagcacag gaaacaaagc gcgggagaat tcaaactaaa    840
aaggaagtgt caatcaaatg tactttgcgg gacttggtta gtaaaagagt aacatcacct    900
gaagactgga tgatgttaca accagatagt tatattgaaa tgatggcaca accaggaggt    960
gaaaatcttt taaaaaatac acttgaaatt tgtactttga ctttagcaag aacaaaaaca   1020
gcatttgaat taatacttga aaaagcagat aatactaaac taactaactt tgatcttgca   1080
aattctagaa catgtcaaat ttttagaatg cacggatgga attggattaa agtttgtcac   1140
gctatagcat gtgtttttaaa tagacaaggt ggtaaaagaa atacagttct ttttcatgga   1200
ccagcaagta caggaaaatc tatcattgct caagccatag cacaagctgt gggtaatgtt   1260
ggttgttata atgcagcaaa tgtaaatttt ccatttaatg actgtaccaa taaaaattta   1320
atttggattg aagaagctgg taactttggt caacaagtta atcaatttaa agcaatttgt   1380
tctggacaaa caattagaat tgatcaaaaa ggtaaaggaa gtaagcaaat tgaaccaact   1440
ccagtaatta tgacaactaa tgaaaatata acaattgtga ggattggatg tgaagaaaga   1500
cctgaacata cacaaccaat aagagacaga atgttgaaca ttaagttagt atgtaagctt   1560
ccaggagact ttggtttggt tgataaagaa gaatggcctt taatatgtgc atggttagtt   1620
aaacatggtt atgaatcaac catggctaac tatacacatc attggggaaa agtaccagaa   1680
tgggatgaaa actgggcgga gcctaaaata caagaaggta taaattcacc aggttgcaaa   1740
gacttagaga cacaagcggc aagcaatcct cagagtcaag accaagttca cgtacgtatg   1800
actccggacg tagtggacct tgcactggaa ccgtggagta ctccagatac gcctattgca   1860
gaaactgcaa atcaacaatc aaaccaactt ggcgttactc acaaagacgt gcaagcgagt   1920
ccgacgtggt ccgaaataga ggcagacctg agagccatct ttacttctga acaattggaa   1980
gaagattttc gagacgactt ggattaa                                       2007
```

<210> SEQ ID NO 8
<211> LENGTH: 668
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Ser Gly Asn Gln Tyr Thr Glu Glu Val Met Glu Gly Val Asn Trp
1               5                   10                  15

Leu Lys Lys His Ala Glu Asn Glu Ala Phe Ser Phe Val Phe Lys Cys
            20                  25                  30

Asp Asn Val Gln Leu Asn Gly Lys Asp Val Arg Trp Asn Asn Tyr Thr
        35                  40                  45

Lys Pro Ile Gln Asn Glu Glu Leu Thr Ser Leu Ile Arg Gly Ala Gln
    50                  55                  60

Thr Ala Met Asp Gln Thr Glu Glu Glu Met Asp Trp Glu Ser Glu
65                  70                  75                  80

Val Asp Ser Leu Ala Lys Lys Gln Val Gln Thr Phe Asp Ala Leu Ile
                85                  90                  95
```

```
Lys Lys Cys Leu Phe Glu Val Phe Val Ser Lys Asn Ile Glu Pro Asn
            100                 105                 110

Glu Cys Val Trp Phe Ile Gln His Glu Trp Gly Lys Asp Gln Gly Trp
            115                 120                 125

His Cys His Val Leu Leu His Ser Lys Asn Leu Gln Gln Ala Thr Gly
            130                 135                 140

Lys Trp Leu Arg Arg Gln Met Asn Met Tyr Trp Ser Arg Trp Leu Val
145                 150                 155                 160

Thr Leu Cys Ser Val Asn Leu Thr Pro Thr Glu Lys Ile Lys Leu Arg
                165                 170                 175

Glu Ile Ala Glu Asp Ser Glu Trp Val Thr Ile Leu Thr Tyr Arg His
            180                 185                 190

Lys Gln Thr Lys Lys Asp Tyr Val Lys Met Val His Phe Gly Asn Met
            195                 200                 205

Ile Ala Tyr Tyr Phe Leu Thr Lys Lys Lys Ile Val His Met Thr Lys
            210                 215                 220

Glu Ser Gly Tyr Phe Leu Ser Thr Asp Ser Gly Trp Lys Phe Asn Phe
225                 230                 235                 240

Met Lys Tyr Gln Asp Arg Gln Ile Val Ser Thr Leu Tyr Thr Glu Gln
                245                 250                 255

Met Lys Pro Glu Thr Val Glu Thr Thr Val Thr Thr Ala Gln Glu Thr
            260                 265                 270

Lys Arg Gly Arg Ile Gln Thr Lys Lys Glu Val Ser Ile Lys Cys Thr
            275                 280                 285

Leu Arg Asp Leu Val Ser Lys Arg Val Thr Ser Pro Glu Asp Trp Met
        290                 295                 300

Met Leu Gln Pro Asp Ser Tyr Ile Glu Met Met Ala Gln Pro Gly Gly
305                 310                 315                 320

Glu Asn Leu Leu Lys Asn Thr Leu Glu Ile Cys Thr Leu Thr Leu Ala
                325                 330                 335

Arg Thr Lys Thr Ala Phe Glu Leu Ile Leu Glu Lys Ala Asp Asn Thr
            340                 345                 350

Lys Leu Thr Asn Phe Asp Leu Ala Asn Ser Arg Thr Cys Gln Ile Phe
            355                 360                 365

Arg Met His Gly Trp Asn Trp Ile Lys Val Cys His Ala Ile Ala Cys
        370                 375                 380

Val Leu Asn Arg Gln Gly Gly Lys Arg Asn Thr Val Leu Phe His Gly
385                 390                 395                 400

Pro Ala Ser Thr Gly Lys Ser Ile Ile Ala Gln Ala Ile Ala Gln Ala
                405                 410                 415

Val Gly Asn Val Gly Cys Tyr Asn Ala Ala Asn Val Asn Phe Pro Phe
                420                 425                 430

Asn Asp Cys Thr Asn Lys Asn Leu Ile Trp Ile Glu Glu Ala Gly Asn
            435                 440                 445

Phe Gly Gln Gln Val Asn Gln Phe Lys Ala Ile Cys Ser Gly Gln Thr
        450                 455                 460

Ile Arg Ile Asp Gln Lys Gly Lys Gly Ser Lys Gln Ile Glu Pro Thr
465                 470                 475                 480

Pro Val Ile Met Thr Thr Asn Glu Asn Ile Thr Ile Val Arg Ile Gly
                485                 490                 495

Cys Glu Glu Arg Pro Glu His Thr Gln Pro Ile Arg Asp Arg Met Leu
            500                 505                 510

Asn Ile Lys Leu Val Cys Lys Leu Pro Gly Asp Phe Gly Leu Val Asp
```

-continued

```
            515                 520                 525

Lys Glu Glu Trp Pro Leu Ile Cys Ala Trp Leu Val Lys His Gly Tyr
    530                 535                 540

Glu Ser Thr Met Ala Asn Tyr Thr His His Trp Gly Lys Val Pro Glu
545                 550                 555                 560

Trp Asp Glu Asn Trp Ala Glu Pro Lys Ile Gln Glu Gly Ile Asn Ser
                565                 570                 575

Pro Gly Cys Lys Asp Leu Glu Thr Gln Ala Ala Ser Asn Pro Gln Ser
            580                 585                 590

Gln Asp Gln Val His Val Arg Met Thr Pro Asp Val Val Asp Leu Ala
        595                 600                 605

Leu Glu Pro Trp Ser Thr Pro Asp Thr Pro Ile Ala Glu Thr Ala Asn
    610                 615                 620

Gln Gln Ser Asn Gln Leu Gly Val Thr His Lys Asp Val Gln Ala Ser
625                 630                 635                 640

Pro Thr Trp Ser Glu Ile Glu Ala Asp Leu Arg Ala Ile Phe Thr Ser
                645                 650                 655

Glu Gln Leu Glu Glu Asp Phe Arg Asp Asp Leu Asp
            660                 665
```

```
<210> SEQ ID NO 9
<211> LENGTH: 2169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgtgttttt ttataggact tgtgcctcca ggttataaat atcttgggcc tgggaacagt       60
cttgaccaag gagaaccaac taaccttct gacgccgctg caaaagaaca cgacgaagct      120
tacgctgctt atcttcgctc tggtaaaaac ccatacttat atttctcgcc agcagatcaa      180
cgctttatag atcaaactaa ggacgctaaa gattgggggg ggaaaatagg acattatttt      240
tttagagcta aaaaggcaat tgctccagta ttaactgata caccagatca tccatcaaca      300
tcaagaccaa caaaaccaac taaaagaagt aaaccaccac ctcatatttt cattaatctt      360
gcaaaaaaaa aaaaagccgg tgcaggacaa gtaaaaagag acaatcttgc accaatgagt      420
gatggagcag ttcaaccaga cggtggtcaa cctgctgtca gaaatgaaag agcaacagga      480
tctgggaacg ggtctggagg cggggggtggt ggtggttctg ggggtgtggg gatttctacg      540
ggtactttca ataatcagac ggaatttaaa tttttggaaa acggatgggt ggaaatcaca      600
gcaaactcaa gcagacttgt acatttaaat atgccagaaa gtgaaaatta tagaagagtg      660
gttgtaaata atttggataa aactgcagtt aacggaaaca tggctttaga tgatactcat      720
gcacaaattg taacaccttg gtcattggtt gatgcaaatg cttggggagt ttggtttaat      780
ccaggagatt ggcaactaat tgttaatact atgagtgagt tgcatttagt tagttttgaa      840
caagaaattt ttaatgttgt tttaaagact gtttcagaat ctgctactca gccaccaact      900
aaagtttata ataatgattt aactgcatca ttgatggttg cattagatag taataatact      960
atgccattta ctccagcagc tatgagatct gagacattgg gttttttatcc atggaaacca     1020 accataccaa ctccatggag atattatttt caatgggata gaacattagt accatctcat     1080
actggaacta gtggcacacc aacaaatata taccatggta cagatccaga tgatgttcaa     1140
ttttatacta ttgaaaattc tgtgccagta cacttactaa gaacaggtga tgaatttgct     1200
```

-continued

```
acaggaacat ttttttttga ttgtaaacca tgtagactaa cacatacatg gcaaacaaat    1260
agagcattgg gcttaccacc atttctaaat tctttgcctc aagctgaagg aggtactaac    1320
tttggttata taggagttca acaagataaa agacgtggtg taactcaaat gggaaataca    1380
aactatatta ctgaagctac tattatgaga ccagctgagg ttggttatag tgcaccatat    1440
tattcttttg aggcgtctac acaagggcca tttaaaacac ctattgcagc aggacggggg    1500
ggagcgcaaa cagatgaaaa tcaagcagca gatggtgatc caagatatgc atttggtaga    1560
caacatggta aaaaaactac cacaacagga gaaacacctg agagatttac atatatagca    1620
catcaagata caggaagata tccagaagga gattggattc aaaatattaa ctttaacctt    1680
cctgtaacag aagataatgt attgctacca acagatccaa ttggaggtaa aacaggaatt    1740
aactatacta atatatttaa tacttatggt cctttaactg cattaaataa tgtaccacca    1800
gtttatccaa atggtcaaat ttgggataaa gaatttgata ctgacttaaa accaagactt    1860
catgtaaatg caccatttgt ttgtcaaaat aattgtcctg gtcaattatt tgtaaaagtt    1920
gcgcctaatt taacaaatga atatgatcct gatgcatctg ctaatatgtc aagaattgta    1980
acttactcag attttttggtg gaaaggtaaa ttagtattta aagctaaact aagagcctct    2040
catacttgga atccaattca acaaatgagt attaatgtag ataaccaatt taactatgta    2100
ccaagtaata ttggaggtat gaaaattgta tatgaaaaat ctcaactagc acctagaaaa    2160
ttatattaa                                                             2169
```

<210> SEQ ID NO 10
<211> LENGTH: 722
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Cys Phe Phe Ile Gly Leu Val Pro Pro Gly Tyr Lys Tyr Leu Gly
1               5                   10                  15

Pro Gly Asn Ser Leu Asp Gln Gly Glu Pro Thr Asn Pro Ser Asp Ala
            20                  25                  30

Ala Ala Lys Glu His Asp Glu Ala Tyr Ala Ala Tyr Leu Arg Ser Gly
        35                  40                  45

Lys Asn Pro Tyr Leu Tyr Phe Ser Pro Ala Asp Gln Arg Phe Ile Asp
    50                  55                  60

Gln Thr Lys Asp Ala Lys Asp Trp Gly Gly Lys Ile Gly His Tyr Phe
65                  70                  75                  80

Phe Arg Ala Lys Lys Ala Ile Ala Pro Val Leu Thr Asp Thr Pro Asp
                85                  90                  95

His Pro Ser Thr Ser Arg Pro Thr Lys Pro Thr Lys Arg Ser Lys Pro
            100                 105                 110

Pro Pro His Ile Phe Ile Asn Leu Ala Lys Lys Lys Ala Gly Ala
            115                 120                 125

Gly Gln Val Lys Arg Asp Asn Leu Ala Pro Met Ser Asp Gly Ala Val
        130                 135                 140

Gln Pro Asp Gly Gly Gln Pro Ala Val Arg Asn Glu Arg Ala Thr Gly
145                 150                 155                 160

Ser Gly Asn Gly Ser Gly Gly Gly Gly Gly Gly Ser Gly Gly Val
                165                 170                 175
```

```
Gly Ile Ser Thr Gly Thr Phe Asn Asn Gln Thr Glu Phe Lys Phe Leu
        180                 185                 190

Glu Asn Gly Trp Val Glu Ile Thr Ala Asn Ser Ser Arg Leu Val His
        195                 200                 205

Leu Asn Met Pro Glu Ser Glu Asn Tyr Arg Arg Val Val Val Asn Asn
    210                 215                 220

Leu Asp Lys Thr Ala Val Asn Gly Asn Met Ala Leu Asp Asp Thr His
225                 230                 235                 240

Ala Gln Ile Val Thr Pro Trp Ser Leu Val Asp Ala Asn Ala Trp Gly
                245                 250                 255

Val Trp Phe Asn Pro Gly Asp Trp Gln Leu Ile Val Asn Thr Met Ser
            260                 265                 270

Glu Leu His Leu Val Ser Phe Glu Gln Glu Ile Phe Asn Val Val Leu
        275                 280                 285

Lys Thr Val Ser Glu Ser Ala Thr Gln Pro Pro Thr Lys Val Tyr Asn
    290                 295                 300

Asn Asp Leu Thr Ala Ser Leu Met Val Ala Leu Asp Ser Asn Asn Thr
305                 310                 315                 320

Met Pro Phe Thr Pro Ala Ala Met Arg Ser Glu Thr Leu Gly Phe Tyr
                325                 330                 335

Pro Trp Lys Pro Thr Ile Pro Thr Pro Trp Arg Tyr Tyr Phe Gln Trp
            340                 345                 350

Asp Arg Thr Leu Val Pro Ser His Thr Gly Thr Ser Gly Thr Pro Thr
            355                 360                 365

Asn Ile Tyr His Gly Thr Asp Pro Asp Val Gln Phe Tyr Thr Ile
    370                 375                 380

Glu Asn Ser Val Pro Val His Leu Leu Arg Thr Gly Asp Glu Phe Ala
385                 390                 395                 400

Thr Gly Thr Phe Phe Phe Asp Cys Lys Pro Cys Arg Leu Thr His Thr
                405                 410                 415

Trp Gln Thr Asn Arg Ala Leu Gly Leu Pro Pro Phe Leu Asn Ser Leu
            420                 425                 430

Pro Gln Ala Glu Gly Gly Thr Asn Phe Gly Tyr Ile Gly Val Gln Gln
        435                 440                 445

Asp Lys Arg Arg Gly Val Thr Gln Met Gly Asn Thr Asn Tyr Ile Thr
    450                 455                 460

Glu Ala Thr Ile Met Arg Pro Ala Glu Val Gly Tyr Ser Ala Pro Tyr
465                 470                 475                 480

Tyr Ser Phe Glu Ala Ser Thr Gln Gly Pro Phe Lys Thr Pro Ile Ala
                485                 490                 495

Ala Gly Arg Gly Gly Ala Gln Thr Asp Glu Asn Gln Ala Ala Asp Gly
            500                 505                 510

Asp Pro Arg Tyr Ala Phe Gly Arg Gln His Gly Lys Lys Thr Thr Thr
        515                 520                 525

Thr Gly Glu Thr Pro Glu Arg Phe Thr Tyr Ile Ala His Gln Asp Thr
    530                 535                 540

Gly Arg Tyr Pro Glu Gly Asp Trp Ile Gln Asn Ile Asn Phe Asn Leu
545                 550                 555                 560

Pro Val Thr Glu Asp Asn Val Leu Leu Pro Thr Asp Pro Ile Gly Gly
                565                 570                 575

Lys Thr Gly Ile Asn Tyr Thr Asn Ile Phe Asn Thr Tyr Gly Pro Leu
            580                 585                 590

Thr Ala Leu Asn Asn Val Pro Pro Val Tyr Pro Asn Gly Gln Ile Trp
```

```
              595                  600                  605
Asp Lys Glu Phe Asp Thr Asp Leu Lys Pro Arg Leu His Val Asn Ala
    610                  615                  620

Pro Phe Val Cys Gln Asn Asn Cys Pro Gly Gln Leu Phe Val Lys Val
625                  630                  635                  640

Ala Pro Asn Leu Thr Asn Glu Tyr Asp Pro Asp Ala Ser Ala Asn Met
              645                  650                  655

Ser Arg Ile Val Thr Tyr Ser Asp Phe Trp Trp Lys Gly Lys Leu Val
              660                  665                  670

Phe Lys Ala Lys Leu Arg Ala Ser His Thr Trp Asn Pro Ile Gln Gln
    675                  680                  685

Met Ser Ile Asn Val Asp Asn Gln Phe Asn Tyr Val Pro Ser Asn Ile
    690                  695                  700

Gly Gly Met Lys Ile Val Tyr Glu Lys Ser Gln Leu Ala Pro Arg Lys
705                  710                  715                  720

Leu Tyr
```

```
<210> SEQ ID NO 11
<211> LENGTH: 4920
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4904)..(4920)
<223> OTHER INFORMATION: a, c, t, or g

<400> SEQUENCE: 11
atcattcttt agaaccaact gaccaagttc acgtacgtat gacgtgatga cgcgcgctgc      60
gcgcgctgcc tacggcagtc acacgtcata cgtacgctcc ttggtcagtt ggttctaaag     120
aatgataggc ggtttgtgtg tttaaacttg ggcgggaaaa ggtggcgggc taattgtggg     180
cgtggttaaa ggtataaaag acaaaccata gaccgttact gacattcgct tcttgtcttt     240
gacagagtga acctctctta ctttgactaa ccatgtctgg caaccagtat actgaggaag     300
ttatggaggg agtaaattgg ttaaagaaac atgcagaaaa tgaagcattt tcgtttgttt     360
ttaaatgtga caacgtccaa ctaaatggaa aggatgttcg ctggaacaac tataccaaac     420
caattcaaaa tgaagagcta acatctttaa ttagaggagc acaaacagca atggatcaaa     480
ccgaagaaga agaaatggac tgggaatcgg aagttgatag tctcgccaaa aagcaagtac     540
aaacttttga tgcattaatt aaaaaatgtc tttttgaagt ctttgtttct aaaaatatag     600
aaccaaatga atgtgtttgg tttattcaac atgaatgggg aaaagatcaa ggctggcatt     660
gtcatgtttt acttcatagt aagaacttac aacaagcaac tggtaaatgg ctacgcagac     720
aaatgaatat gtattggagt agatggttgg tgactctttg ttcggtaaac ttaacaccaa     780
ctgaaaagat taagctcaga gaaattgcag aagatagtga atgggtgact atattaacat     840
acagacataa gcaaacaaaa aaagactatg ttaaaatggt tcattttgga aatatgatag     900
catattactt tttaacaaag aaaaaaattg tccacatgac aaaagaaagt ggctatttt     960 taagtactga ttctggttgg aaatttaact ttatgaagta tcaagacaga caaattgtca    1020
gcacacttta cactgaacaa atgaaaccag aaaccgttga aaccacagtg acgacagcac    1080
aggaaacaaa gcgcgggaga attcaaacta aaaaggaagt gtcaatcaaa tgtactttgc    1140
gggacttggt tagtaaaaga gtaacatcac ctgaagactg gatgatgtta caaccagata   1200
```

-continued

```
gttatattga aatgatggca caaccaggag gtgaaaatct tttaaaaaat acacttgaaa    1260
tttgtacttt gactttagca agaacaaaaa cagcatttga attaatactt gaaaaagcag    1320
ataatactaa actaactaac tttgatcttg caaattctag aacatgtcaa atttttagaa    1380
tgcacggatg gaattggatt aaagtttgtc acgctatagc atgtgtttta aatagacaag    1440
gtggtaaaag aaatacagtt cttttcatg gaccagcaag tacaggaaaa tctatcattg    1500
ctcaagccat agcacaagct gtgggtaatg ttggttgtta taatgcagca aatgtaaatt    1560
ttccatttaa tgactgtacc aataaaaatt taatttggat tgaagaagct ggtaactttg    1620
gtcaacaagt taatcaattt aaagcaattt gttctggaca aacaattaga attgatcaaa    1680
aaggtaaagg aagtaagcaa attgaaccaa ctccagtaat tatgacaact aatgaaaata    1740
taacaattgt gaggattgga tgtgaagaaa gacctgaaca tacacaacca ataagagaca    1800
gaatgttgaa cattaagtta gtatgtaagc ttccaggaga ctttggtttg gttgataaag    1860
aagaatggcc tttaatatgt gcatggttag ttaaacatgg ttatgaatca accatggcta    1920
actatacaca tcattgggga aaagtaccag aatgggatga aaactgggcg gagcctaaaa    1980
tacaagaagg tataaattca ccaggttgca aagacttaga gacacaagcg gcaagcaatc    2040
ctcagagtca agaccaagtt cacgtacgta tgactccgga cgtagtggac cttgcactgg    2100
aaccgtggag tactccagat acgcctattg cagaaactgc aaatcaacaa tcaaaccaac    2160
ttggcgttac tcacaaagac gtgcaagcga gtccgacgtg gtccgaaata gaggcagacc    2220
tgagagccat cttttacttct gaacaattgg aagaagattt tcgagacgac ttggattaag    2280
gtacgatggc acctccggca aagagagcca ggagaggtaa gggtgtgtta gtaaagtggg    2340
gggagaggaa agatttaata acttaactaa gtatgtgttt tttttatagga cttgtgcctc    2400 caggttataa atatcttggg cctgggaaca gtcttgacca aggagaacca actaaccctt    2460
ctgacgccgc tgcaaaagaa cacgacgaag cttacgctgc ttatcttcgc tctggtaaaa    2520
acccatactt atatttctcg ccagcagatc aacgctttat agatcaaact aaggacgcta    2580
aagattgggg gggaaaata ggacattatt tttttagagc taaaaaggca attgctccag    2640
tattaactga tacaccagat catccatcaa catcaagacc aacaaaacca actaaaagaa    2700
gtaaaccacc acctcatatt ttcattaatc ttgcaaaaaa aaaaaaagcc ggtgcaggac    2760
aagtaaaaag agacaatctt gcaccaatga gtgatggagc agttcaacca gacggtggtc    2820
aacctgctgt cagaaatgaa agagcaacag gatctgggaa cgggtctgga ggcggggggtg    2880 gtggtggttc tgggggtgtg gggatttcta cgggtacttt caataatcag acggaattta    2940
aatttttgga aaacggatgg gtggaaatca cagcaaactc aagcagactt gtacatttaa    3000
atatgccaga aagtgaaaat tatagaagag tggttgtaaa taatttggat aaaactgcag    3060
ttaacggaaa catggcttta gatgatactc atgcacaaat tgtaacacct tggtcattgg    3120
ttgatgcaaa tgcttgggga gtttggttta atccaggaga ttggcaacta attgttaata    3180
ctatgagtga gttgcattta gttagttttg aacaagaaat ttttaatgtt gttttaaaga    3240
ctgtttcaga atctgctact cagccaccaa ctaaagttta taataatgat ttaactgcat    3300
cattgatggt tgcattagat agtaataata ctatgccatt tactccagca gctatgagat    3360
ctgagacatt gggttttttat ccatggaaac caaccatacc aactccatgg agatattatt    3420
ttcaatggga tagaacatta gtaccatctc atactggaac tagtggcaca ccaacaaata    3480
tataccatgg tacagatcca gatgatgttc aattttatac tattgaaaat tctgtgccag    3540
```

-continued

```
tacacttact aagaacaggt gatgaatttg ctacaggaac attttttttt gattgtaaac    3600
catgtagact aacacataca tggcaaacaa atagagcatt gggcttacca ccatttctaa    3660
attctttgcc tcaagctgaa ggaggtacta actttggtta tataggagtt caacaagata    3720
aaagacgtgg tgtaactcaa atgggaaata caaactatat tactgaagct actattatga    3780
gaccagctga ggttggttat agtgcaccat attattcttt tgaggcgtct acacaagggc    3840
catttaaaac acctattgca gcaggacggg ggggagcgca aacagatgaa aatcaagcag    3900
cagatggtga tccaagatat gcatttggta dacaacatgg taaaaaaact accacaacag    3960
gagaaacacc tgagagattt acatatatag cacatcaaga tacaggaaga tatccagaag    4020
gagattggat tcaaaatatt aactttaacc ttcctgtaac agaagataat gtattgctac    4080
caacagatcc aattggaggt aaaacaggaa ttaactatac taatatattt aatacttatg    4140
gtcctttaac tgcattaaat aatgtaccac cagtttatcc aaatggtcaa atttgggata    4200
aagaatttga tactgactta aaaccaagac ttcatgtaaa tgcaccattt gtttgtcaaa    4260
ataattgtcc tggtcaatta tttgtaaaag ttgcgcctaa tttaacaaat gaatatgatc    4320
ctgatgcatc tgctaatatg tcaagaattg taacttactc agatttttgg tggaaaggta    4380
aattagtatt taaagctaaa ctaagagcct ctcatacttg gaatccaatt caacaaatga    4440
gtattaatgt agataaccaa tttaactatg taccaagtaa tattggaggt atgaaaattg    4500
tatatgaaaa atctcaacta gcacctagaa aattatatta acatacttac tatgttttta    4560
tgtttattac atattatttt aagattaatt aaattacagc atagaaatat tgtacttgta    4620
tttgatatag gatttagaag gtttgttata tggtatacaa taactgtaag aaatagaaga    4680
acatttagat catagttagt agtttgtttt ataaaatgta ttgtaaacta ttaatgtatg    4740
ttgttatggt gtgggtggtt ggttggtttg cccttagaat atgttaagga ccaaaaaaaa    4800
tcaataaaag acatttaaaa ctaaatggcc tcgtatactg tctataaggt gaactaacct    4860
taccataagt atcaatctgt ctttaagggg ggggtgggtg ggannnnnnn nnnnnnnnnn    4920
```

```
<210> SEQ ID NO 12
<211> LENGTH: 584
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 12

Met Ser Asp Gly Ala Val Gln Pro Asp Gly Gly Gln Pro Ala Val Arg
1               5                   10                  15

Asn Glu Arg Ala Thr Gly Ser Gly Asn Gly Ser Gly Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Arg
65                  70                  75                  80

Arg Val Val Val Asn Asn Leu Asp Lys Thr Ala Val Asn Gly Asn Met
                85                  90                  95

Ala Leu Asp Asp Thr His Ala Gln Ile Val Thr Pro Trp Ser Leu Val
            100                 105                 110

Asp Ala Asn Ala Trp Gly Val Trp Phe Asn Pro Gly Asp Trp Gln Leu
```

```
                 115                 120                 125
Ile Val Asn Thr Met Ser Glu Leu His Leu Val Ser Phe Glu Gln Glu
    130                 135                 140
Ile Phe Asn Val Val Leu Lys Thr Val Ser Glu Ser Ala Thr Gln Pro
145                 150                 155                 160
Pro Thr Lys Val Tyr Asn Asn Asp Leu Thr Ala Ser Leu Met Val Ala
                165                 170                 175
Leu Asp Ser Asn Asn Thr Met Pro Phe Thr Pro Ala Ala Met Arg Ser
                180                 185                 190
Glu Thr Leu Gly Phe Tyr Pro Trp Lys Pro Thr Ile Pro Thr Pro Trp
                195                 200                 205
Arg Tyr Tyr Phe Gln Trp Asp Arg Thr Leu Val Pro Ser His Thr Gly
    210                 215                 220
Thr Ser Gly Thr Pro Thr Asn Ile Tyr His Gly Thr Asp Pro Asp Asp
225                 230                 235                 240
Val Gln Phe Tyr Thr Ile Glu Asn Ser Val Pro Val His Leu Leu Arg
                245                 250                 255
Thr Gly Asp Glu Phe Ala Thr Gly Thr Phe Phe Phe Asp Cys Lys Pro
                260                 265                 270
Cys Arg Leu Thr His Thr Trp Gln Thr Asn Arg Ala Leu Gly Leu Pro
                275                 280                 285
Pro Phe Leu Asn Ser Leu Pro Gln Ala Glu Gly Gly Thr Asn Phe Gly
    290                 295                 300
Tyr Ile Gly Val Gln Gln Asp Lys Arg Arg Gly Val Thr Gln Met Gly
305                 310                 315                 320
Asn Thr Asn Tyr Ile Thr Glu Ala Thr Ile Met Arg Pro Ala Glu Val
                325                 330                 335
Gly Tyr Ser Ala Pro Tyr Tyr Ser Phe Glu Ala Ser Thr Gln Gly Pro
                340                 345                 350
Phe Lys Thr Pro Ile Ala Ala Gly Arg Gly Gly Ala Gln Thr Asp Glu
                355                 360                 365
Asn Gln Ala Ala Asp Gly Asp Pro Arg Tyr Ala Phe Gly Arg Gln His
    370                 375                 380
Gly Lys Lys Thr Thr Thr Thr Gly Glu Thr Pro Glu Arg Phe Thr Tyr
385                 390                 395                 400
Ile Ala His Gln Asp Thr Gly Arg Tyr Pro Glu Gly Asp Trp Ile Gln
                405                 410                 415
Asn Ile Asn Phe Asn Leu Pro Val Thr Glu Asp Asn Val Leu Leu Pro
                420                 425                 430
Thr Asp Pro Ile Gly Gly Lys Thr Gly Ile Asn Tyr Thr Asn Ile Phe
                435                 440                 445
Asn Thr Tyr Gly Pro Leu Thr Ala Leu Asn Asn Val Pro Pro Val Tyr
    450                 455                 460
Pro Asn Gly Gln Ile Trp Asp Lys Glu Phe Asp Thr Asp Leu Lys Pro
465                 470                 475                 480
Arg Leu His Val Asn Ala Pro Phe Val Cys Gln Asn Asn Cys Pro Gly
                485                 490                 495
Gln Leu Phe Val Lys Val Ala Pro Asn Leu Thr Asn Glu Tyr Asp Pro
                500                 505                 510
Asp Ala Ser Ala Asn Met Ser Arg Ile Val Thr Tyr Ser Asp Phe Trp
                515                 520                 525
Trp Lys Gly Lys Leu Val Phe Lys Ala Lys Leu Arg Ala Ser His Thr
    530                 535                 540
```

-continued

```
Trp Asn Pro Ile Gln Gln Met Ser Ile Asn Val Asp Asn Gln Phe Asn
545             550             555             560

Tyr Val Pro Ser Asn Ile Gly Gly Met Lys Ile Val Tyr Glu Lys Ser
            565             570             575

Gln Leu Ala Pro Arg Lys Leu Tyr
            580
```